United States Patent
Lal et al.

(10) Patent No.: US 10,864,270 B2
(45) Date of Patent: Dec. 15, 2020

(54) NANOSTRUCTURED CARRIERS FOR GUIDED AND TARGETED ON-DEMAND SUBSTANCE DELIVERY

(71) Applicant: The Regents of the University of California, Oakland, CA (US)

(72) Inventors: Ratneshwar Lal, La Jolla, CA (US); Preston B. Landon, San Diego, CA (US); Alexander Mo, La Jolla, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 16/111,090

(22) Filed: Aug. 23, 2018

(65) Prior Publication Data
US 2019/0134198 A1   May 9, 2019

Related U.S. Application Data

(63) Continuation of application No. 15/318,175, filed as application No. PCT/US2015/035898 on Jun. 15, 2015, now Pat. No. 10,245,322.
(Continued)

(51) Int. Cl.
*A61K 9/51* (2006.01)
*A61K 47/69* (2017.01)
(Continued)

(52) U.S. Cl.
CPC ............ *A61K 41/00* (2013.01); *A61K 9/0009* (2013.01); *A61K 9/5115* (2013.01);
(Continued)

(58) Field of Classification Search
None
See application file for complete search history.

(56) References Cited

U.S. PATENT DOCUMENTS 8,097,173 B2 * 1/2012 Sailor ............... B22F 1/0003
216/2
2003/0082237 A1 5/2003 Cha et al.
(Continued)

FOREIGN PATENT DOCUMENTS

WO 1987007150 A1 12/1987
WO 2012142625 A2 10/2012
WO WO-2012142625 A2 * 10/2012 ........ B01J 20/28021

OTHER PUBLICATIONS

Ambrogio et al. "Mechanized Silica Nanoparticles: A New Frontier in Theranostic Nanomedlcine," Accounts of Chemical Research. vol. 44, No. 10. Jun. 15, 2011, 9 pages.
(Continued)

*Primary Examiner* — Melissa S Mercier
(74) *Attorney, Agent, or Firm* — Perkins Coie LLP

(57) ABSTRACT

Methods, systems, and devices are disclosed for fabricating and implementing nanoscale and microscale structured carriers to provide guided, targeted, and on-demand delivery of molecules and biochemical substances for a variety of applications including diagnosis and/or treatment (theranostics) of diseases in humans and animals. In some aspects, a nanostructure carrier can be synthesized in the form of a nanobowl, which may include an actuatable capping particle that can be opened (and in some implementations, closed) on demand. In some aspects, a nanostructure carrier can be synthesized in the form of a hollow porous nanoparticle with a functionalized interior and/or exterior to attach payload substances and substances for magnetically guided delivery and controlled release of substance payloads.

19 Claims, 40 Drawing Sheets

Related U.S. Application Data

(60) Provisional application No. 62/029,373, filed on Jul. 25, 2014, provisional application No. 62/012,136, filed on Jun. 13, 2014.

(51) Int. Cl.
*A61K 41/00* (2020.01)
*A61K 9/00* (2006.01)
*A61K 38/05* (2006.01)

(52) U.S. Cl.
CPC .......... *A61K 9/5138* (2013.01); *A61K 9/5192* (2013.01); *A61K 38/05* (2013.01); *A61K 41/0028* (2013.01); *A61K 47/6923* (2017.08); *A61K 47/6925* (2017.08); *A61K 47/6941* (2017.08)

(56) References Cited

U.S. PATENT DOCUMENTS

| | | | |
|---|---|---|---|
| 2005/0221316 | A1 | 10/2005 | Pedersen et al. |
| 2011/0215277 | A1* | 9/2011 | Khan .................. B01J 8/00 252/408.1 |
| 2014/0080198 | A1 | 3/2014 | Lal et al. |
| 2017/0119891 | A1 | 5/2017 | Lal et al. |

OTHER PUBLICATIONS

Arnal, et al., "High-Temperature-Stable Catalysts by Hollow Sphere Encapsulation", Angewandte Chemie 2006, 118 (48), 8404-8407.
Aznar, et al, "Glucose-triggered release using enzyme-gated mesoporous silica nanoparticles", Chem. Commun., 2013,49, 6391-6393.
Benenson, Y. et al., "Programmable and autonomous computing machine made of biomolecules", Nature 2001, 414, (6862), 430-434.
Binks, "Particles as Surfactants—Similarities and Differences", Curr. Opin. Colloid Interface Sci., 2002, pp. 21-41.
Braasch, D. A.; Corey, D. R., Locked nucleic acid (LNA): fine-tuning the recognition of DNA and RNA. Chemistry & Biology 2001, 8, (1), 1-7.
Caruso, et al., "Nanoengineering of inorganic and hybrid hollow spheres by colloidal templating", Science 1998, 282 (5391), 1111-1114.
Chen, et al., "Preparation and characterization of porous hollow silica nanoparticles for drug delivery application", Biomaterials 2004, 25 (4), 723-727.
Chen et al., "Controlled Assembly of Eccentrically Encapsulated Gold Nanoparticles", J. Am. Chem., 2008, pp. 11858-11859.
Chen et al., "Scalable Routes to Janus Au—Sio2 and Ternary Ag—Au—Sio2 Nanoparticles", Chem. Mater., 2010, pp. 3826-3828.
Chen, Y.; Mao, C., Reprogramming DNA-directed reactions on the basis of a DNA conformational change. Journal of the American Chemical Society 2004, 126, (41), 13240-13241.
Chen, Y., et al. "An autonomous DNA nanomotor powered by a DNA enzyme" Angewandte Chemie—International Edition 2004, 43, (27), 3554-3557.
Climent, et al., (2010), Controlled Delivery Using Oligonucleotide-Capped Mesoporous Silica Nanoparticles. Angew. Chem., 122: 7439-7441.
Elbaz, J. et al."Coherent Activation of DNA Tweezers: A "Set-Reset" Logic System", Angewandte Chemie—International Edition 2009, 48, (21), 3834-3837.
Elbaz, J. et al. "Parallel analysis of two analytes in solutions or on surfaces by using a bifunctional aptamer: Applications for biosensing and logic gate operations" Chembiochem 2008, 9, (2), 232-239.
Fu et al., "Controlled Free Radical Generation against Tumor Cells by Ph-Responsive Mesoporous Silica Nanocomposite", J. Mat. Chem., 2014, pp. 3538-3548.
Ge et al., "The Morphological Control of Anisotropic Polystyrene/Silica Hybrid Particles Prepared by Radiation Miniemulsion Polymerization", Chem. Commun., 2009, pp. 2765-2767.
Gobin, et al., "Near-Infrared Resonant Nanoshells for Combined Optical Imaging and Photothermal Cancer Therapy", Nano Letters 2007, 7 (7), 1929-1934.
Grabar, et al., "Two-Dimensional Arrays of Colloidal Gold Particles: A Flexible Approach to Macroscopic Metal Surfaces", Langmuir 1996, 12 (10), 2353-2361.
Graham, et al., "Nanodetoxification: emerging role of nanomaterials in drug intoxication treatment", Nanomedicine (Lond) 2011, 6 (5), 921-8.
Han, et al., Photothermal therapy of cancer cells using novel hollow gold nanoflowers. International journal of nanomedicine 2014, 9, 517-26.
Han, X., et al. "Catch and Release: DNA Tweezers that Can Capture, Hold, and Release an Object under Control" Journal of the American Chemical Society 2008, 130, (44), 14414-14415.
Hong et al., "Simple Method to Produce Janus Colloidal Particles in Large Quantity" Langmuir 2006, pp. 9495-9499.
Hu et al., "Nanocomposties with Spatially Separated Functionalities for Combined Imaging and Magnetolytic Therapy", J. Am. Chem. Soc. 2010, pp. 7234-7237.
Igor, et al., "Mesoporous silica nanoparticles as controlled release drug delivery and gene transfection carriers", Advanced Drug Delivery Reviews, vol. 60, Issue 11, Aug. 17, 2008, pp. 1278-1288.
Im, et al., Polymer hollow particles with controllable holes in their surfaces. Nat. Mater. 2005, 4 (9), 671-675.
Integrated DNA Technologies Inc., OligoAnalyzer 3.1, http://www.idtdna.com/analyzer/Applications/OligoAnalyzer/. 2011.
Jin, et al., "Spectrally Tunable Leakage-Free Gold Nanocontainers", Journal of the American Chemical Society 2009, 131 (49), 17774-17776.
Kaewsaneha et al., "Janus Colloidal Particles: Preparation, Properties, and Biomedical Applications", ACS Appl. Mater. Interfaces, 2013, pp. 1857-1869.
Kim, et al., Designed Fabrication of Multifunctional Magnetic Gold Nanoshells and Their Application to Magnetic Resonance Imaging and Photothermal Therapy: Angew. Chem., 2006, 118: 7918-7922.
Kokufuta, et al., "Adsorption of Poly(Diallyldimethylammonium Chloride) on Colloid Silica from Water and Salt Solution", Macromolecules 1986, 19 (2), pp. 351-354.
Kong et al., "Magnetic Targeting of Nanoparticles across the Intact Blood-Brain Barrier", J. Controlled Release, 2012, pp. 49-57.
Kong et al., "Magnetically Vectored Nanocapsules for Tumor Penetration and Remotely Switchable on-Demand Drug Release", Nano Lett., 2010, pp. 5088-5092.
Landon, P. B. et al., "DNA zipper-based tweezers", Langmuir, vol. 28(1), Sep. 15, 2011, pp. 534-540.
Landon, et al., "Designing Hollow Nano Gold Golfballs," ACS Appl. Mater. Interfaces, 2014, 6 (13), pp. 9937-9941.
Li, D., et al. "Optical analysis of Hg2+ ions by oligonucleotide-gold-nanoparticle hybrids and DNA-based machines" Angewandte Chemie—International Edition 2008, 47, (21), 3927-3931.
Ling et al., "Janus Particles with Controllable Patchiness and Their Chemical Functionalization and Supramolecular Assembly", Agnew. Chem. Int. Ed., 2009, pp. 7677-7682.
Liang, et al., "Gold Hollow Nanospheres: Tunable Surface Plasmon Resonance Controlled by Interior-Cavity Sizes", the Journal of Physical Chemistry B 2005, 109 (16), 7795-7800.
Lu et al., "Synthesis and Crystallization of Hybrid Spherical Colloids Composed of Polystyrene Cores and Silica Shells", Langmuir, 2004, pp. 3464-3470.
Lu, et al., "Synthesis and self-assembly of Au@SiO2 core-shell colloids", Nano Letters 2002, 2 (7), 785-788.
Mao, C., et al. "A nanomechanical device based on the B-Z transition of DNA" Nature 1999, 397, (6715), 144-146.
Meng et al., "Synthesis of Dissymmetrical Nanoparticles with a New Hybrid Silican Template", J. Colloid Interace Sci., 2011, pp. 429-433.
Mo, et al., "Synthesis of Nano-Bowls with a Janus Template," Nancoscale, Jan. 14, 2015; 7(2), pp. 771-775.
Mock, et al., "Composite plasmon resonant nanowires", Nano Letters 2002, 2 (5), 465-469.

(56) References Cited

OTHER PUBLICATIONS

Muller, B. K. et al., Single-pair FRET characterization of DNA tweezers, Nano Letters, vol. 6(12), pp. 2814-2820 (Dec. 2006).
Nguyen, et al., A Reversible Molecular Valve:, Proc. Natl. Acad. Sci. U.S.A. 2005, 102, pp. 10029-10034.
Nielsen, P. E.; Egholm, M.; Berg, R. H.; Buchardt, O., Sequence-Selective Recognition of DNA by Strand Displacement with a Thymine-Substituted Polyamide. Science 1991, 254, (5037), 1497-1500.
Nikoobakht, et al., "Preparation and Growth Mechanism of Gold Nanorods (NRs) Using Seed-Mediated Growth Method", Chem. Mat. 2003, 15 (10), 1957-1962.
Nisisako et al., "Synthesis of Monodisperse Bicolored Janus Particles with Electrical Anisotropy using a Microfluidic Co-Flow System", Adv. Mater. 2007, pp. 1152-1156.
Nomura, et al., "Synthesis of hollow silica microparticles from bacterial templates", Adv. Powder Technol. 2010, 21 (2), pp. 218-222.
Nutiu, R.; Li, Y. F., A DNA-protein nanoengine for "On-Demand" release and precise delivery of molecules. Angewandte Chemie—International Edition 2005, 44, (34), 5464-5467.
Oldenburg, et al., "Nanoengineering of optical resonances", Chemical Physics Letters 1998, 288 (2), pp. 243-247.
Oldenburg, et al., "Surface enhanced Raman scattering in the near infrared using metal nanoshell substrates", the Journal of chemical physics 1999, 111 (10), pp. 4729-4735.
Ortac et al. "Dual-Porosity Hollow Nanoparticles for the Immunoprotection and Delivery of Nonhuman Enzymes," Nano Letters, vol. 14, No. 6., Jan. 28, 2014, 9 pages.
Pan et al., "PEGylated liposome coated QDs/mesoporous silica core-shell nanoparticles for molecular imaging", Chem. Commun., 2011, pp. 3442-3444.
Park, et al., "The effect of pH-adjusted gold colloids on the formation of gold clusters over APTMS-coated silica cores", B Kor Chem Soc 2006, 27 (9), pp. 1341-1345.
Peng, et al., "ZnSe Semiconductor Hollow Microspheres", Angewandte Chemie International Edition 2003, 42 (26), pp. 3027-3030.
Pham, et al., "Preparation and characterization of gold nanoshells coated with self-assembled monolayers", Langmuir 2002, 18 (12), pp. 4915-4920.
Ramachandran et al., "Cisplatin Nanoliposomes for Cancer Therapy: Afm and Flourescence Imagin of Cisplatin Encapsulation, Stability, Cellular Uptake, and Toxicity", Langmuire, 2006, pp. 8156-8162.
Ratneshwar, "Distinguished Lecture by Prof. Ratnesh Lal", You Tube, 2013, pp. 1-7.
Sadowska, et al., "Mechanism of Nanoparticle Deposition on Polystyrene Latex Particles", Langmuir 2014, 30 (3), pp. 692-699.
Sanchez-Gaytan, et al., "Spiky Gold Nanoshells", Langmuir 2010, 26 (24), pp. 19170-19174.
Shchukin, et al., "Template synthesis of porous gold microspheres", Chemical Communications 2003, (13), pp. 1478-1479.
Shin, J. S.; Pierce, N. A., A synthetic DNA walker for molecular transport. Journal of the American Chemical Society 2004, 126, (35), 10834-10835.
Simmel, F.C., "Towards biomedical applications for nucleic acid nanodevices," Nanomedicine, 2007, vol. 2, pp. 817-830.
Simmel, F. C., Processive Motion of Bipedal DNA Walkers. Chemphyschem 2009, 10, (15), 2593-2597.
Song, et al., "Plasmonic Vesicles of Amphiphilic Gold Nanocrystals: Self-Assembly and External-Stimuli-Triggered Destruction", Journal of the American Chemical Society 2011, 133 (28), pp. 10760-10763.
Stober et al., "Controlled Growth of Monodisperse Silica Spheres in the Micron Size Range", J. Colloid Interace Sci., 1968, pp. 62-69.
Stoeva, et al., "Three-Layer Composite Magnetic Nanoparticle Probes for DNA", J. Am. Chem. Soc., 2005, 127 (44), pp. 15362-15363.
Su, et al., "A Novel Shell-Structure Cell Microcarrier (SSCM) for Cell Transplantation and Bone Regeneration Medicine", Pharm. Res. 2011, 28 (6), pp. 1431-1441.

Sun, et al., "Shape-controlled synthesis of gold and silver nanoparticles", Science 2002, 298 (5601), pp. 2176-2179.
Sun, etal., "Alloying and dealloying processes involved in the preparation of metal nanoshells through a galvanic replacement reaction", Nano Letters 2003, 3 (11), pp. 1569-1572.
Tan et al., "Fabrication of Polymer Nanocavities with Tailored Openings", ACS Nano, 2009, pp. 3469-3474.
Tang et al., "Large Scale Synthesis of Janus Submicrometer Sized Colloids by Seeded Emulsion Polymerization", 2010, pp. 5114-5120.
Teller, C. et al., "Functional nucleic acid nanostructures and DNA machines", Current Opinion in Biotechnology, vol. 21(4), Aug. 19, 2010, pp. 376-391.
Torney, et al., "Mesoporous silica nanoparticles deliver DNA and chemicals into plants", Nature Nanotechnology 2, 2007, pp. 295-300.
Walther et al., "Janus Particles: Synthesis, Self-Assembly, Physical Properties and Appplication", Chem. Rev., 2013, pp. 5194-5261.
Wan, et al., "New Strategy to Prepare Hollow Silica Microspheres with Tunable Holes on the Shell Wall", Langmuir 2014, 30 (3), pp. 683-686.
Wang et al., "Facile One-Pot Synthesis and Morphological Control of Asymmetric Superparamagnetic Composite Nanoparticles", Chem. Commun., 2011, pp. 10350-10352.
Wang, et al. "Facile one-pot synthesis of yolk-shell superparamagnetic nanocomposites via ternary phase separations" Chem. Commun., 2011, 47, pp. 10350-10352.
Wang et al., "Dumbbell-like Pt—Fe304 Nanoparticles and Their Enhanced Catalysis for Oxygen Reduxction Reaction", Nano Lett. 2009, pp. 1493-1496.
Wang, et al., "Dual Surface-Functionalized Janus Nanocomposites of Polystyrene/Fe3O4@SiO2 for Simultaneous Tumor Cell Targeting and Stimulus-Induced Drug Release", Adv. Mater., 25, 2013, pp. 3485-3489.
Wang, et al., "Iron oxide-gold core-shell nanoparticles and thin film assembly", J. Mater. Chem. 2005, 15 (18), pp. 1821-1832.
Wang, J.; Kawde, A. N., Pencil-based renewable biosensor for label-free electrochemical detection of DNA hybridization. Analytica Chimica Acta 2001, 431, (2), 219-224.
Woo, J. S.; Meyer, R. B.; Gamper, H. B., G/C-modified oligodeoxynucleotides with selective complementarity: Synthesis and hybridization properties. Nucleic Acids Research 1996, 24, (13), 2470-2475.
Xia et al. "Engineering sub-100 nm multi-layer nanoshells," Nanotechnology 17, Oct. 20, 2006. pp. 5435-5440.
Xu et al., "Dumbbell-Like Au—Fe3o4 Nanoparticles for Target Specific Platin Delivery", J. Am. Chem. Soc. 2009, pp. 4216-4217.
Xue et al., "PLGA/Mesoporous Silica Hybrid Structure for Controlled Drug Release", J. Controlled Release, 2004, pp. 209-217.
Yi et al., Molecular Zipper: a fluorescent probe for real-time isothermal DNA amplification, Nucleic Acids Research, 2006, vol. 34, No. 11, e81, pp. 1-5.
Yurke, B.; Turberfield, A. J.; Mills, A. P.; Simmel, F. C.; Neumann, J. L., A DNA-fuelled molecular machine made of DNA. Nature 2000, 406, (6796), 605-608.
Zhang et al. "Mesoporous Multifunctional Upconversion Luminescent and Magnetic "Nanoratte" Materials for Targeted Chemotherapy," Nano Letters, Dec. 1, 2011. pp. 61-67.
Zhang, et al., "Emulsion-Templated Gold Beads Using Gold Nanoparticles as Building Blocks", Advanced Materials 2004, 16 (1), pp. 27-30.
Extended European Search Report for European Patent Application No. 15806704.1, dated Jan. 12, 2018, 11 pages.
International Search Report and Written Opinion for International Application No. PCT/US2015/035898, dated Nov. 27, 2015, 15 pages.
International Search Report and Written Opinion of International Application No. PCT/US2012/028383; dated Oct. 23, 2012, 9 pages.
Office Action for European Patent Application No. 15806704.1, dated May 2, 2019, 7 pages.

\* cited by examiner

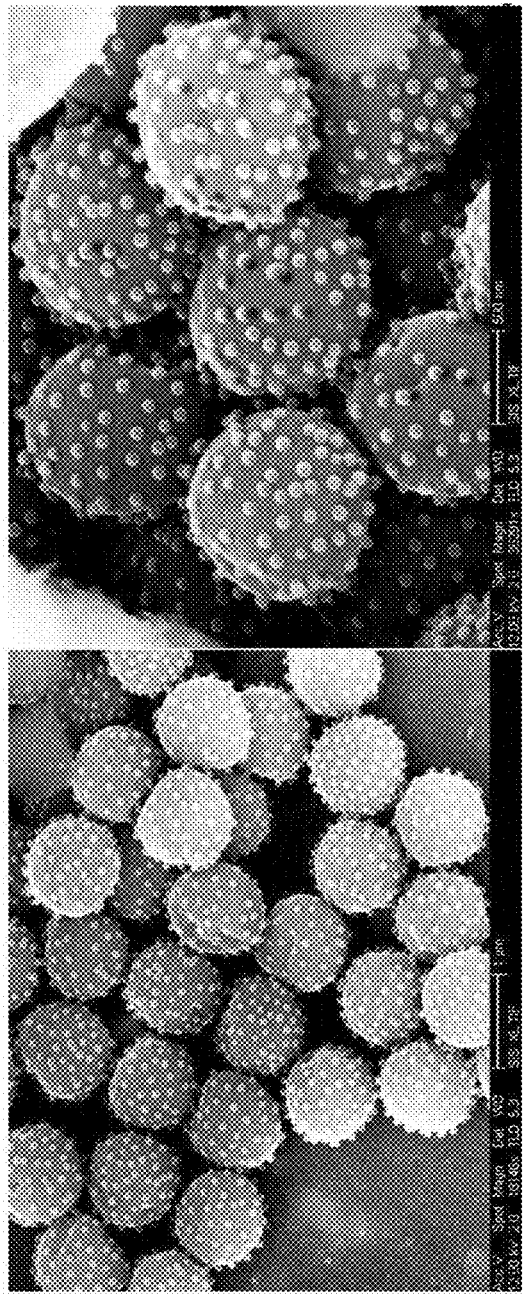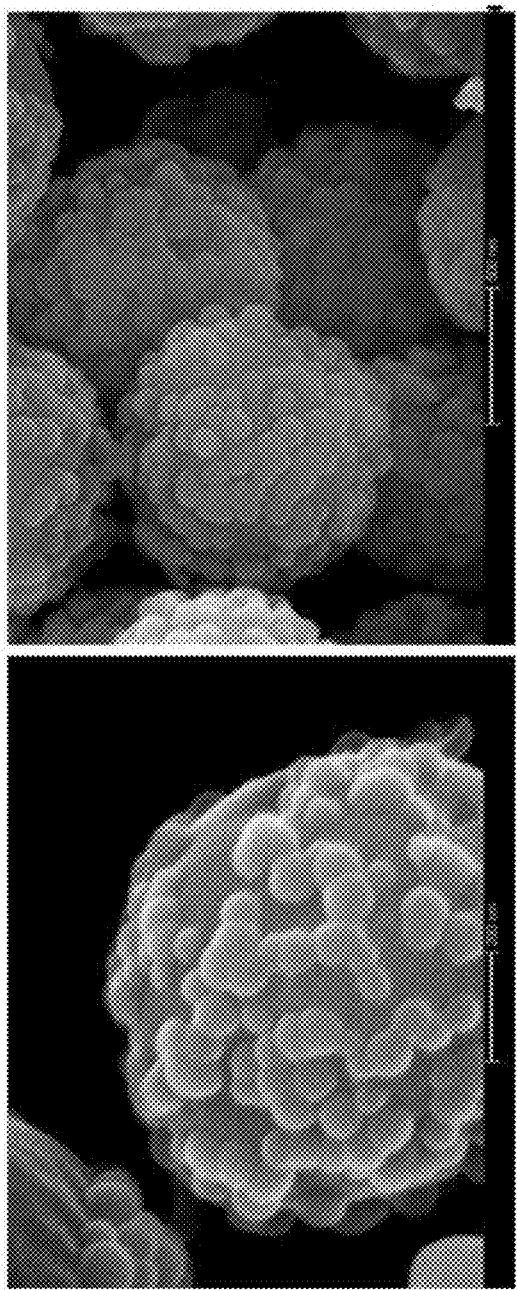
FIG. 9A
FIG. 9B
FIG. 10

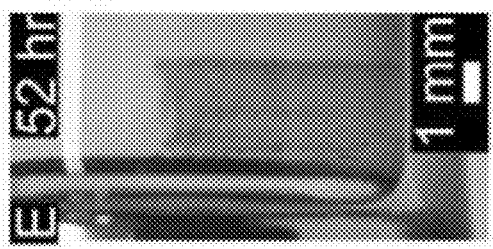
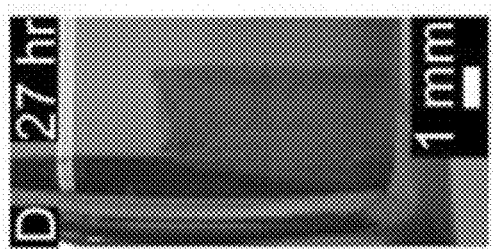
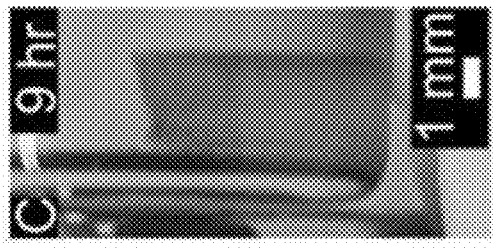
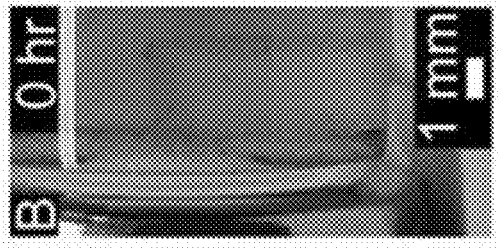
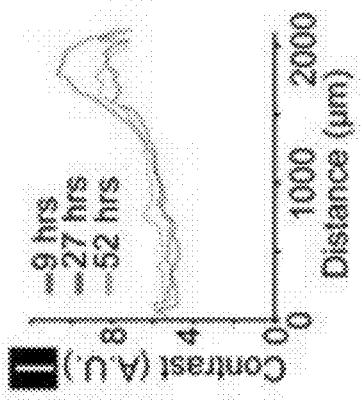
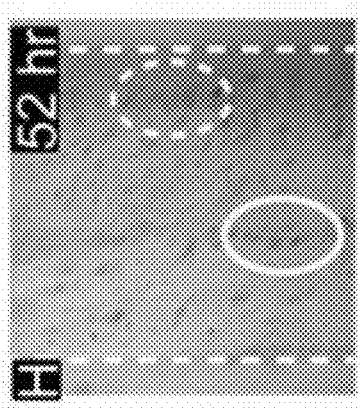
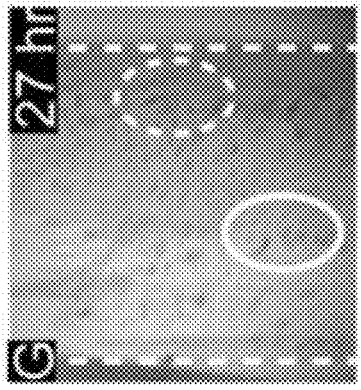
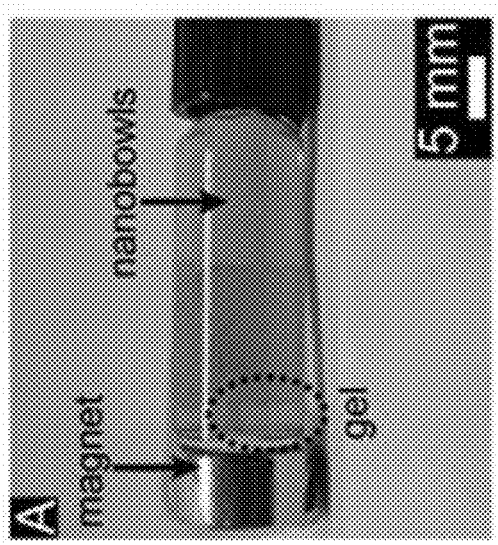
FIG. 32A  FIG. 32B  FIG. 32C  FIG. 32D  FIG. 32E
FIG. 32F  FIG. 32G  FIG. 32H  FIG. 32I

NANOSTRUCTURED CARRIERS FOR GUIDED AND TARGETED ON-DEMAND SUBSTANCE DELIVERY

CROSS-REFERENCE TO RELATED APPLICATIONS

This patent document is a continuation of U.S. patent application Ser. No. 15/318,175 entitled "NANOSTRUCTURED CARRIERS FOR GUIDED AND TARGETED ON-DEMAND SUBSTANCE DELIVERY" filed on Dec. 12, 2016, which is a 371 National Phase Application of PCT Application No. PCT/US2015/035898 entitled "NANOSTRUCTURED CARRIERS FOR GUIDED AND TARGETED ON-DEMAND SUBSTANCE DELIVERY" filed on Jun. 15, 2015, which claims priorities to and benefits of U.S. Provisional Patent Application No. 62/012,136 entitled "NANOSCALE STRUCTURES FOR MAGNETICALLY-GUIDED THERANOSTICS" filed on Jun. 13, 2014, and U.S. Provisional Patent Application No. 62/029,373 entitled "NANOSTRUCTURED CARRIERS FOR TARGETED AND ON-DEMAND DELIVERY OF MOLECULAR SUBSTANCES" filed on Jul. 25, 2014. The entire contents of the above patent applications are incorporated by reference as part of the disclosure of this patent document.

STATEMENT REGARDING FEDERALLY SPONSORED RESEARCH OR DEVELOPMENT

This invention was made with government support under DA024871 and DA025296 awarded by the National Institute on Health. The government has certain rights in the invention.

TECHNICAL FIELD

This patent document relates to systems, devices, and processes that use nanoscale material technologies.

BACKGROUND

Nanotechnology provides techniques or processes for fabricating structures, devices, and systems with features at a molecular or atomic scale, e.g., structures in a range of one to hundreds of nanometers in some applications. For example, nano-scale devices can be configured to sizes similar to some large molecules, e.g., biomolecules such as enzymes. Nano-sized materials used to create a nanostructure, nanodevice, or a nanosystem can exhibit various unique properties, e.g., including optical properties, that are not present in the same materials at larger dimensions and such unique properties can be exploited for a wide range of applications.

SUMMARY

Techniques, systems, and devices are disclosed for fabricating and implementing engineered nanoscale structures for carrying substances and providing directed, targeted, and controlled delivery and release of the substances in biological systems.

In one aspect, a nanostructure device for carrying a payload includes an interior particle structure that includes an opening to an internal cavity of the interior particle structure; an exterior shell structure at least partially formed on an exterior surface of the interior particle structure; a plurality of magnetic nanoparticles within the exterior shell structure; and a functionalization layer on a surface of the internal cavity capable of chemically attaching a molecular payload to the interior particle structure, in which the magnetic nanoparticles are structured to interact with an external magnetic field to magnetically steer the nanostructure device.

In one aspect, a method to produce a nanostructure includes forming an interior particle structure on a core particle, in which the core particle is partially encased by the interior particle structure; attaching nanoparticles to the exterior surface of the interior particle structure; forming a coating on the exterior surface of the interior particle structure that covers at least some of the attached nanoparticles; and removing the core particle from the interior particle structure, in which the removed core particle forms an internal cavity within and an opening from an external surface of the interior particle structure.

In one aspect, a method to fabricate a carrier structure includes forming a template by attaching a plurality of mask particles on a core particle, the mask particles forming masked regions on the exterior surface of the core particle where they attach; attaching nanoparticles to unmasked surface of the template, in which the mask particles prevent the nanoparticles to attach to the masked regions of the exterior surface; producing a shell structure over the unmasked surface of the template by forming a coating over the unmasked surface by material growth of the attached nanoparticles; and producing a porous carrier structure by removing the mask particles from the template, in which the removed mask particles form openings extending between an external surface of the shell structure and the exterior surface of the core particle.

In one aspect, a method to fabricate a carrier structure includes forming a template by attaching a plurality of mask particles on a core particle, the mask particles forming masked regions on the exterior surface of the core particle where they attach; attaching nanoparticles to unmasked surface of the template, in which the mask particles prevent the nanoparticles to attach to the masked regions of the exterior surface; generating discontiguous island structures over the unmasked surface of the template by growing the material of the attached nanoparticles on the unmasked surface to form the island structures; producing a shell structure by forming an outer layer over the unmasked surface of the template and over the discontiguous island structures, in which the produced shell structure includes the outer layer having the island structures embedded on an inner surface of the outer layer; and producing a carrier structure by removing the mask particles from the template, in which the removed mask particles form openings extending between an external surface of the shell structure and the exterior surface of the core particle.

In one aspect, a nanoparticle includes a shell structured to include a hollow interior and one or more openings extending between the hollow interior and an exterior surface of the shell; magnetic nanoparticles attached to one or both of the hollow interior or the exterior surface of the shell, in which the magnetic nanoparticles are structured to interact with an external magnetic field to magnetically steer the nanoparticle; and a molecular payload attached to the shell by attachment molecules capable of linking the molecular payload to a surface of the shell.

In one aspect, a method to fabricate a particle includes forming a first functionalization layer on a core particle to produce a functionalized core particle, in which the formed first functionalization layer creates an opposite charge on the surface of the core particle with respect to the surface charge of the core particle; forming a second functionalization layer on the functionalized core particle to produce a dual-functionalized core particle, in which the formed second functionalization layer creates an oppositely charged surface on the surface of the functionalized core particle than that prior to the formation of the second functionalization layer; forming a template by attaching a plurality of mask particles on the dual-functionalized core particle, in which the mask particles include an opposite charge on their surface with respect to that of the dual-functionalized core particle, and in which the mask particles form masked regions on the exterior surface of the dual-functionalized core particle where they attach; producing a shell structure over the unmasked surface of the dual-functionalized core particle by forming a coating on the unmasked surface of the dual-functionalized core particle, in which the mask particles prevent the coating to attach to the masked regions of the exterior surface; and producing a functionalized hollow porous particle by removing the mask particles and the dual-functionalized core particle, in which the removed mask particles form openings extending between a hollow interior and an external surface of the shell structure. In some implementations of the method, for example, the method can further include, prior to the removing the mask particles and the dual-functionalized core particle, forming a layer on the shell structure by coating the layer using a material having an opposite charge to that of the shell structure; and producing a dual-functionalized hollow porous particle by removing the mask particles and the dual-functionalized core particle, in which the removed mask particles form openings extending between a hollow interior of the shell structure and an external surface of the layer.

The subject matter described in this patent document can be implemented in specific ways that provide one or more of the following features. The disclosed technology includes a multi-functional nanoparticle platform that can be utilized for a variety of diagnostic and therapeutic applications in living organisms in vivo and in vitro. In some embodiments, for example, the disclosed nanostructures can be produced as nanoscale bowl-like structures (e.g., nanobowls) having a hollow interior and functionalized interior and/or exterior surfaces capable of carrying and delivering payload substances, and which may optionally be endowed with a cap structure that can be opened and closed to release payloads on demand. In some implementations, for example, the disclosed nanostructure technology can be implemented as drug delivery capsules, as a protected enzymatic carrier, for shielded detection of reactive species in detection assays, and/or as shielded and confined chemical catalysts. In some embodiments, for example, the disclosed nanostructures can be produced as nano/microscale carrier structures, e.g., nanoscale wiffle ball-like structures and nanoscale golf ball-like structures, having a hollow or solid interior and porous shell with functionalized interior and/or exterior surfaces and capable of magnetic guidance that enable controlled release of a payload, improvement of cellular uptake, and other features For example, the disclosed technology can be implemented for applications including, but not limited to, targeted/on-demand delivery of molecules and materials for the diagnosis and/or treatment (theranostics) of diseases in humans and animals.

BRIEF DESCRIPTION OF THE DRAWINGS

FIGS. 9A and 9B show scanning electron microscopy (SEM) images depicting exemplary templates made from a polystyrene core and silica templates.

FIG. 10 shows SEM images of exemplary fabricated structures with increasing thickness of the silica exterior of nanobowls formed on satellite particles of polystyrene templates.

FIGS. 32A-32I show time lapse images and a data plot of the exemplary functionalized magnetic nanobowl guided through a hydrogel medium.

DETAILED DESCRIPTION

Figure 1:
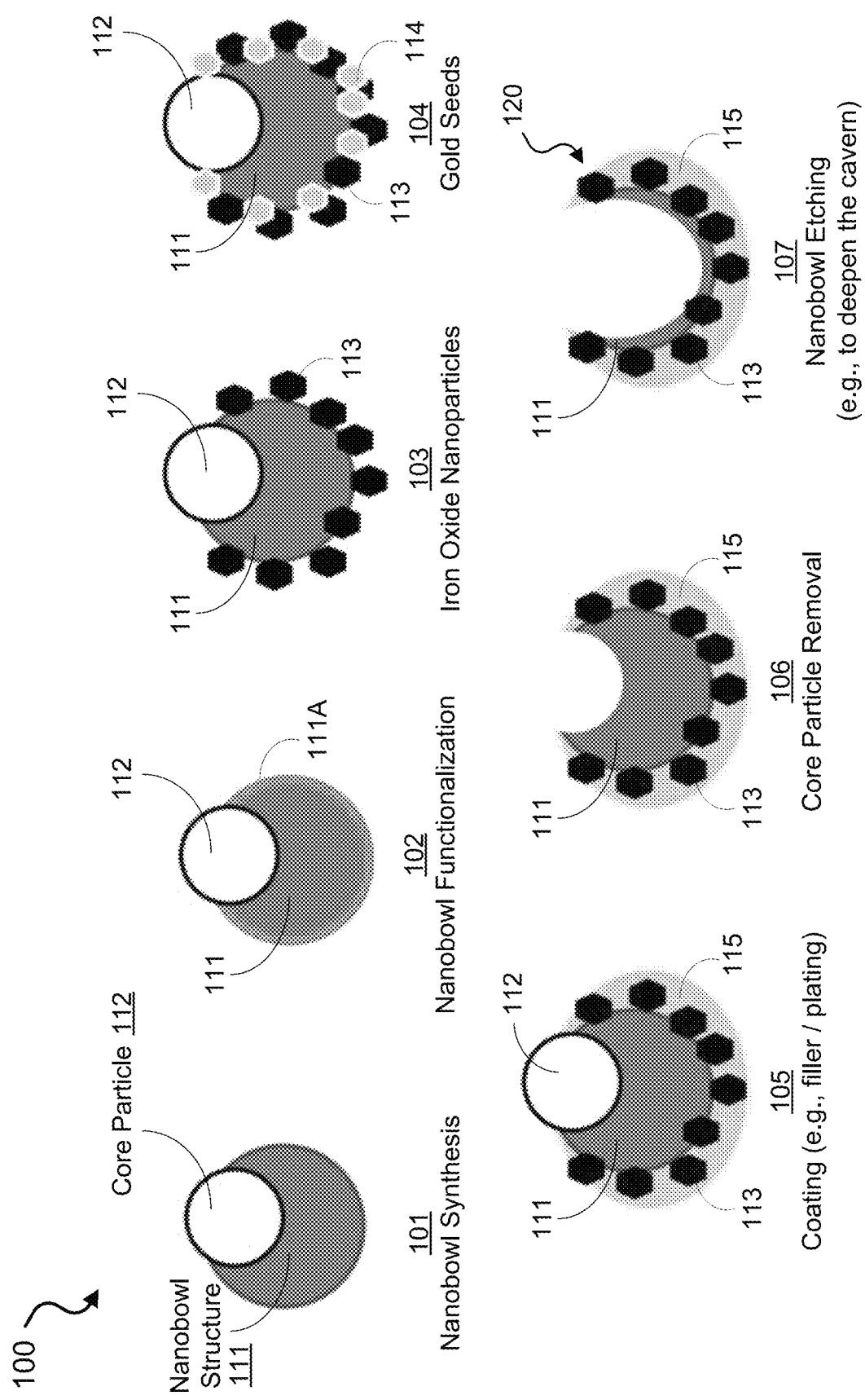
FIG. 1 shows an illustrative schematic of an exemplary fabrication process to synthesize nanobowl carrier structures of the disclosed technology.

Techniques, systems, and devices are disclosed for fabricating and implementing engineered nanoscale structures for carrying substances and providing directed, targeted, and controlled delivery and release of the substances in biological systems. The disclosed technology includes a multifunctional nanoparticle platform that can be utilized for a variety of diagnostic and therapeutic applications in living organisms in vivo and in vitro. The disclosed multi-functional nanoparticle platform provides the capability to controllably direct and guide engineered nanoparticles to specific areas (e.g., tissues, organs, or regions) in a biological system to which the nanoparticles are administered. For example, the disclosed nanoparticles can be structured to move in response to a magnetic field, such that when administered in the bloodstream or ingested through the digestive system of a human subject, the nanoparticles are guided to a tissue or an organ of interest (e.g., the pancreas, breast, prostate, brain, lymph nodes, etc.) by an external applied magnetic field, which can aggregate the administered particles in the targeted area. The disclosed multifunctional nanoparticle platform provides the capability to specifically target and bind to select cells. For example, the disclosed nanoparticles can be structured to include a targeting ligand that interacts with a corresponding receptor on the select cells in the region where the nanoparticles were guided. The disclosed multi-functional nanoparticle platform provides the capability to enclose and protect one or more substances (e.g., payload), and allow for on-demand active or controlled release of the payload by an external stimulus, e.g., when the nanoparticle is uptaken (e.g., endocytosed) by a select cell. In some implementations of the disclosed technology, the multi-functional nanoparticles can be produced to provide one chemical functional group on the interior of the particle, e.g., to be used to attract and/or attach the payload, and provide a uniquely different chemical group on the exterior of the particle, e.g., which can be used to cap or seal the particle. For example, the disclosed nanoparticles can be structured to include a cap that securely seals an opening (e.g., all openings) on the body of the nanoparticle that leads into a hollow interior region where the payload is contained. The cap can be attached to the body of the nanoparticle such that it can be controllably opened and closed by the external stimuli, e.g., on demand.

In some implementations of the nanoscale structures (nanostructures), for example, the nanostructure can be synthesized in the form of a nanoscale bowl-like structure ('nanobowls') endowed with one or more actuatable caps that can be opened and closed on demand. Exemplary applications of the nanobowls can include area-targeted/on-demand delivery and controlled release of molecules and other small materials carried within the nanobowl for the diagnosis and/or treatment (theranostics) of diseases in humans and animals. In some implementations of the engineered material structures, for example, the nanoscale and/or microscale carrier structures having a hollow interior and porous shell with functionalized interior and/or exterior surfaces can be synthesized for magnetically guided delivery and controlled release of substance payloads, which can enhance cellular uptake of the substances by the targeted cells in the desired region while minimizing non-targeted uptake and immune response.

Exemplary Embodiments of the Disclosed Nanobowls

In some aspects of the present technology, the disclosed nanoscale structured carriers can be formed as an asymmetric bowl around a carboxylate containing core particle using chemicals readily soluble in water. Additionally, for this exemplary asymmetric nanoscale bowl structure, adaptations can be made that allow for different modifications to be added to the interior and exterior of the shell. In some implementations, for example, such modifications can include producing the nano-carrier to be magnetically responsive, e.g., by addition of an iron oxide/gold shell of the nanobowl carrier.

Fabrication methods to produce the exemplary nanobowl carriers can include one or more of the following techniques: (i) the synthesis of the nano-carrier by asymmetrical growth of a silica nanobowl formed around a carboxylate-modified core; (ii) modification to the nanobowl carrier structure including by, for example, differential functionalization of interior and exterior surfaces of the nanobowl, modification of the silica surface including by an alkoxysilane, and/or removal of the core; (iii) producing nanoscale cap structures to attach to the body (e.g., shell) of the nanobowl carrier and that can be opened/closed for controlled release of an exemplary cargo (e.g., molecules and materials) from the interior of the nanobowl, in which the opening/closing of the cap of the nano-carrier can be actuated by using physical and/or chemical energy (e.g., from an external source outside the biological system, such as an externally applied magnetic field, or by an internal source at or inside the target cells or tissue, such as a pH condition or interaction with intracellular nucleotides, enzymes, or cellular organelles); (iv) loading of an exemplary molecular payload (e.g., drug, image contrast agent, etc.) into the nanobowl; (v) controlled release of a molecular payload from the nanobowl; (vi) external surface modification of the external surface of the nanobowl with a gold or other metal shell on top of the silica, passivation with an inert or biocompatible material (e.g., polyethylene glycol or similar inert polymer), and/or addition of targeting moieties to improve cellular update (e.g., such as targeting ligands including peptides, oligonucleotides, proteins, or other to interact with integrins or other cellular receptors); and/or (vii) addition of iron oxide nanoparticles into the exterior or interior of the exemplary silica nanobowl structure that can be used for guidance of nano-carriers to a specific location in the biological system (e.g., living organism) under an external magnetic field.

Figure 2:
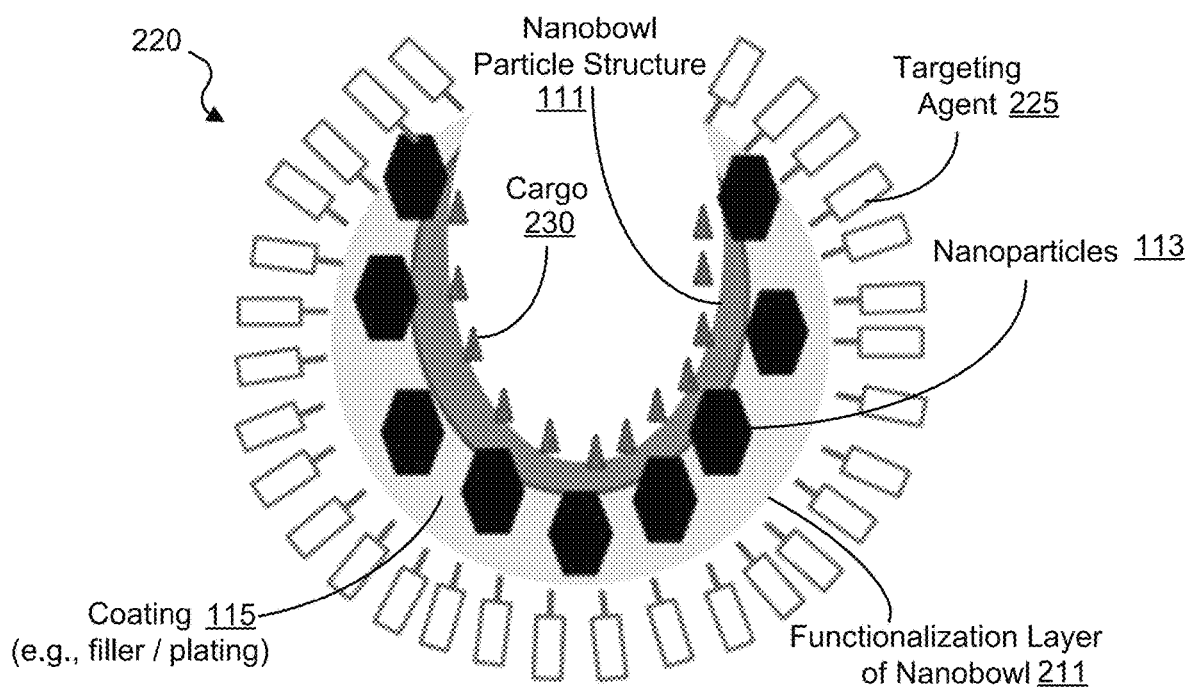
FIG. 2 shows an illustrative diagram of an exemplary nanoparticle carrier loaded with a payload inside and selectively functionalized to include targeting molecules outside.
Figure 3:
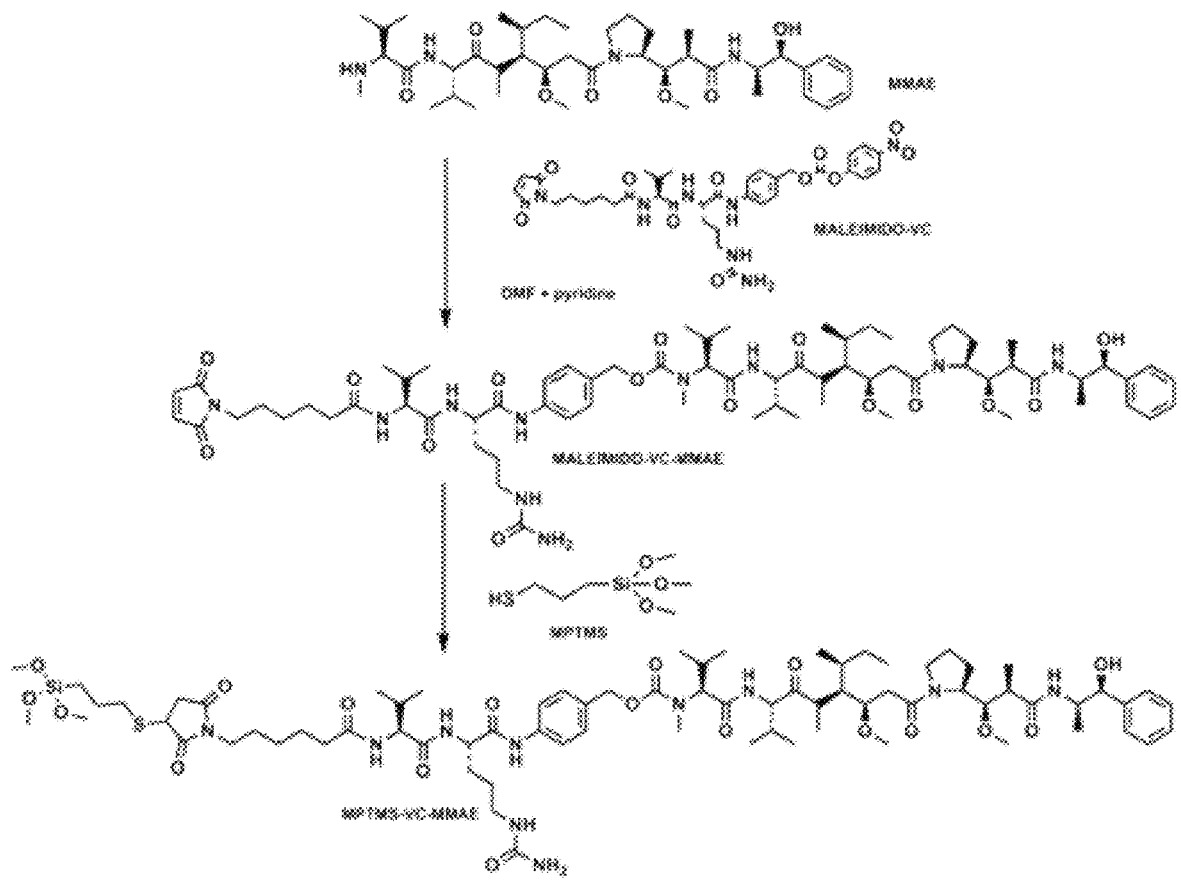
FIG. 3 shows a diagram of an example for maleimide functionalization with thiol containing silane for interfacing with the silica.
Figure 4A:
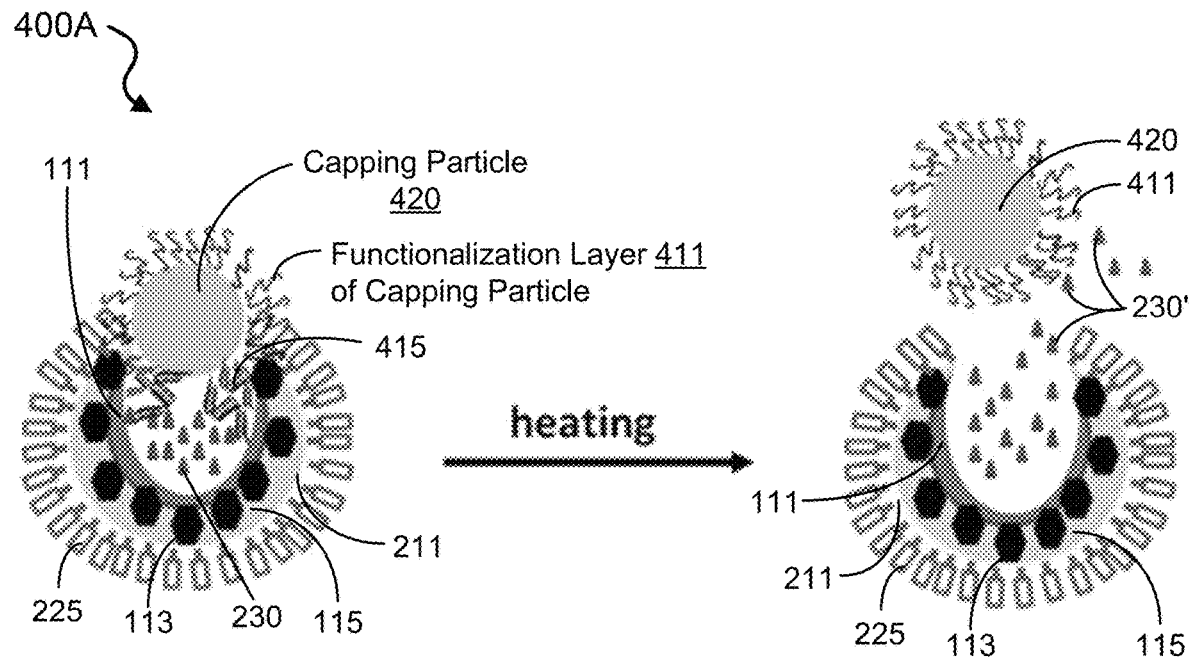
FIGS. 4A and 4B show illustrative diagrams depicting exemplary processes to release or open/close a capping structure of an exemplary nanobowl carrier for controlled release of the payload using laser assisted or RF heating of iron oxide nanoparticles of the nanobowl structure.
Figure 4B:
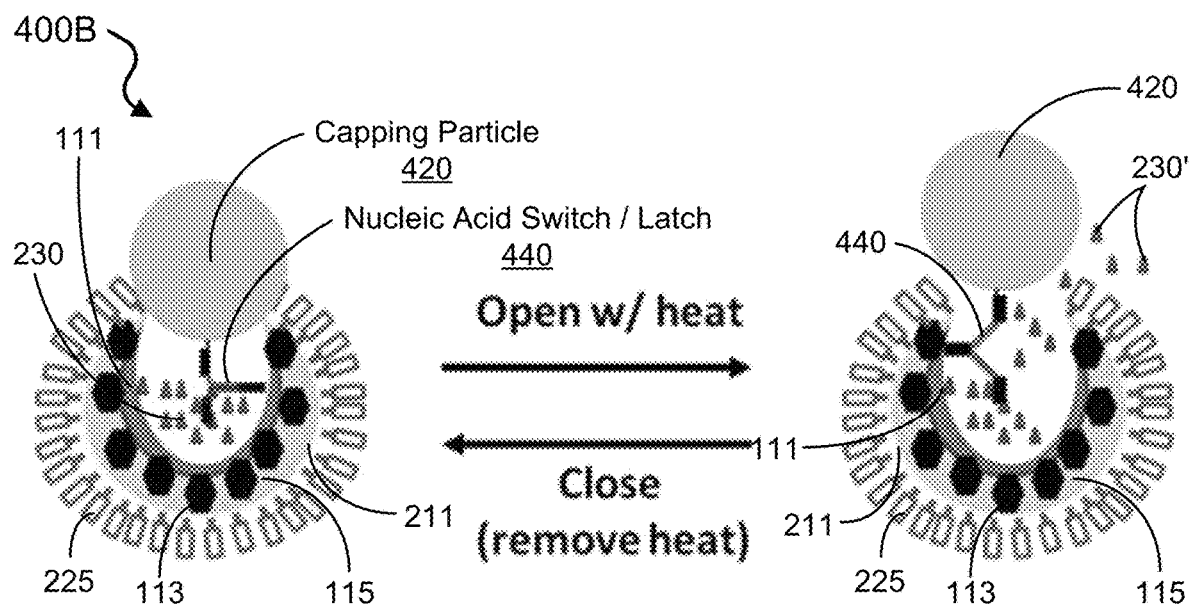
Figure 4C:
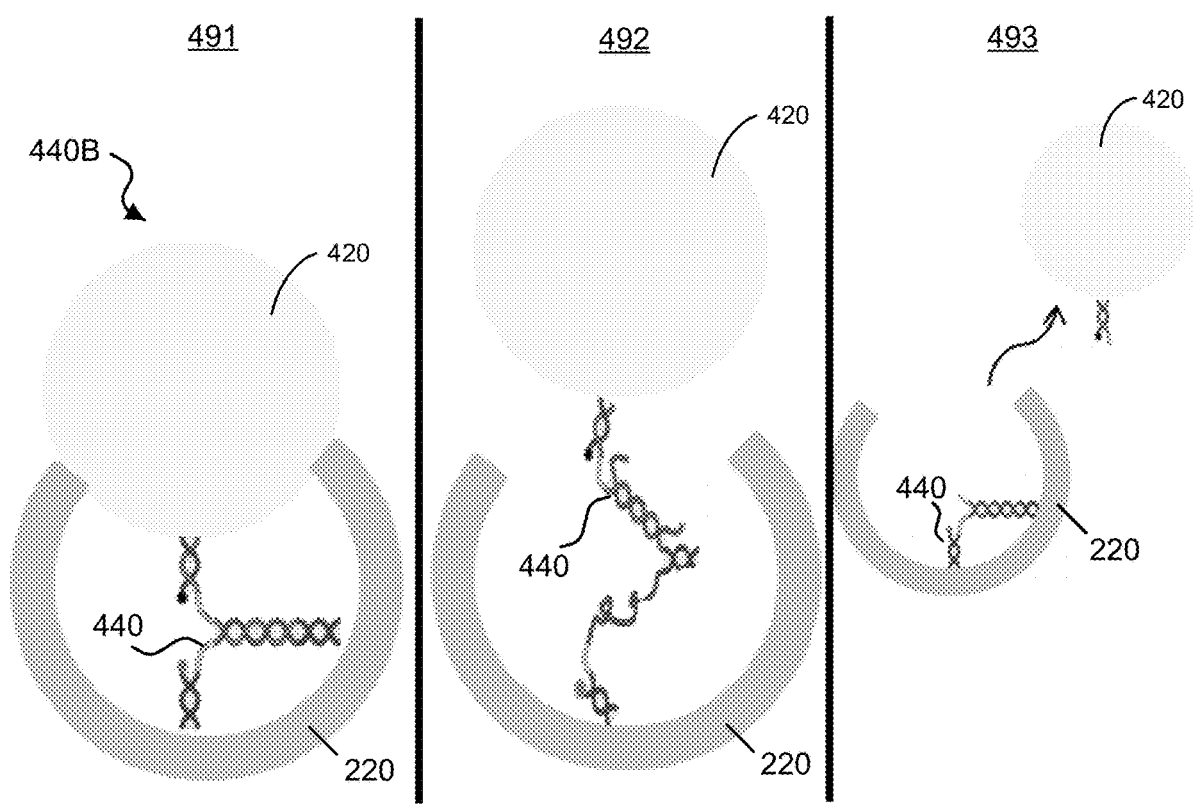
FIG. 4C shows a diagram of an example of the switchable and detachable latch structure of an exemplary nanobowl structure in a closed, opened, and detached state.
Figure 5:
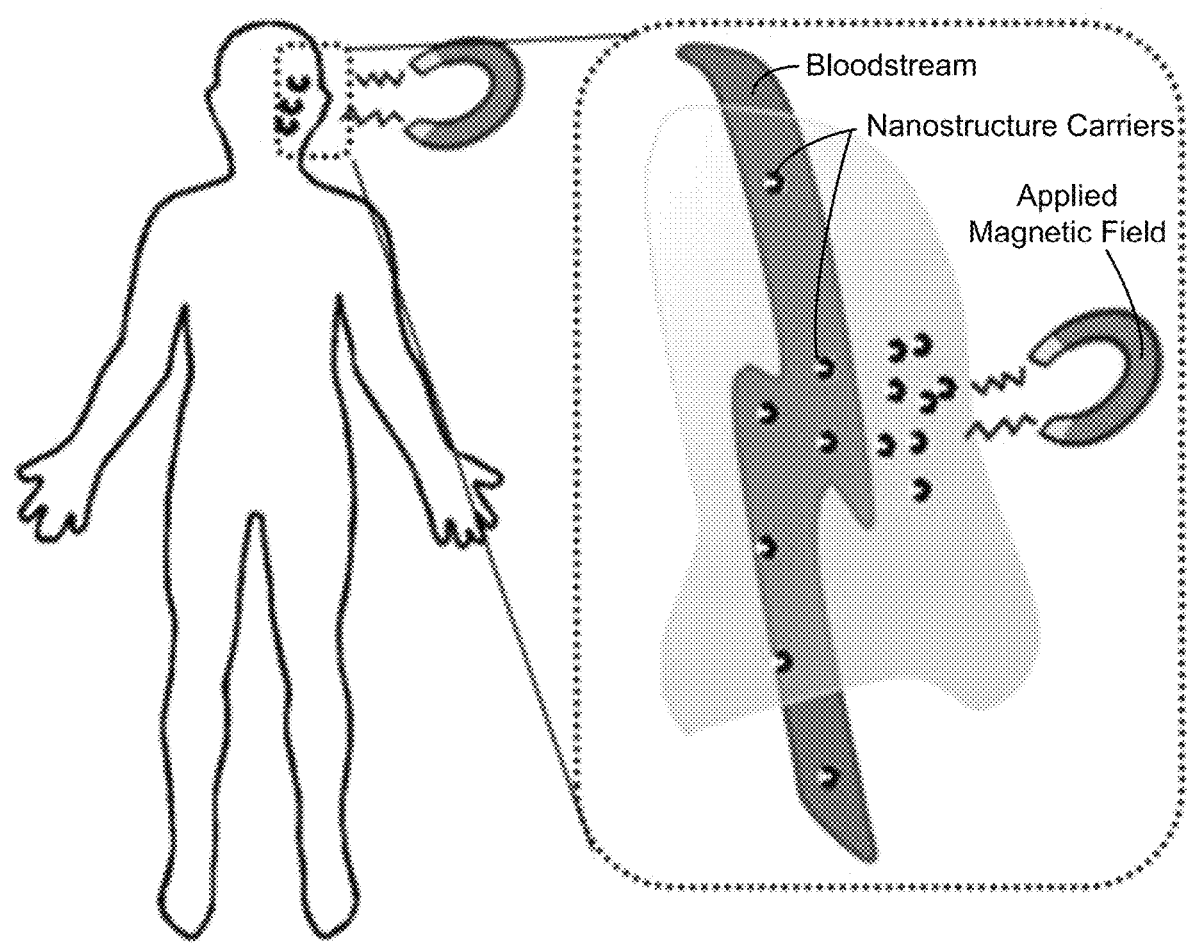
FIG. 5 shows an illustration of an exemplary implementation of the disclosed nano-carriers in which a strong magnet can preferentially pull the exemplary magnetically responsive nanobowls out of the bloodstream and into the tissue of interest.

FIGS. 1-5 show illustrative diagrams of exemplary nanostructures and fabrication techniques to produce and implement the disclosed nanoscale structured carriers. FIG. 1 shows an illustrative schematic of a fabrication process to synthesize an exemplary nanobowl carrier, depicting various reactions to produce the nanobowl structure. FIG. 2 shows an illustrative diagram of an exemplary nanoparticle carrier loaded with a payload (e.g., drugs) inside and selectively functionalized to include targeting molecules outside. FIG. 3 shows a diagram of an example for maleimide functionalization with thiol containing silane for interfacing with the silica. FIGS. 4A and 4B shows illustrative diagrams depicting exemplary processes to release or open/close a capping structure of an exemplary nanobowl carrier for controlled release of the payload using laser assisted or RF heating of iron oxide nanoparticles and/or a gold shell of the nanobowl structure, e.g., which in some embodiments can cause release of the capping structure held in place by DNA. FIG. 5 shows an illustration of an exemplary implementation of the disclosed nano-carriers in which a strong magnet can preferentially pull the exemplary magnetically responsive nanobowls out of the bloodstream and into the tissue of interest.

FIG. 1 shows an exemplary fabrication method 100 of the disclosed technology to synthesize an exemplary nanobowl carrier body. In this example, the synthesis method 100 uses an assymetric formation of a silica nanobowl particle 111 on a functionalized core particle 112, such as a carboxylate functionalized core particle (e.g., polystyrene core particle), as shown in process 101. The synthesis method 100 can include, in some implementations, a process 102 to functionalize the surface of the silica nanobowl particle 111, e.g., amine functionalization of the surface using an amine containing alkosysilane, depicted by surface or layer 111A shown in process 102. Following the surface modification of the silica nanobowl particle 111, the exempalry synthesis method 100 can include adding iron oxide nanoparticles 113 and gold nanoparticle seeds 114 to the exterior of the exemparly silica nanobowl particle 111, which can be electrostatically attached to the surface, as shown in the processes 103 and 104. For example, the iron oxide and gold nanoparticle seeds can be configured to be on the order of 5-15 nm. The exempalry synthesis method 100 can include forming a coating 115, e.g., by producing a filling material between the gold nanoseeds 114, on the external surface of the exemplary seeded nanobowl particle 111, as shown in process 105. For example, the producing the filling material coating 115 can include placing the exempalry seeded silica nanobowl 111/polystyrene core 112 complex in an ionic gold solution and adding a reducing agent that fills in the spaces between the gold nanoseeds 114. In some implementations, for example, the coating 115 can be grown on the silica nanobowl particle 111 as an external shell. In the example shown in FIG. 1, the gold nanoparticle seeds 114 facilitate growth sites to produce an external gold shell over the silica nanobowl particle 111. Finally, the exemplary synthesis method 100 can include removing the exemplary core particle 112, as shown in process 106. In some implementations, for example, the exemplary synthesis method 100 can include etching the exemplary silica material of the nanobowl particle 111 further down, as shown in process 107, e.g., using different, suitable solvents and acids, to enlarge the hollow interior region of the silical nanobowl carrier body 120.

FIG. 2 shows an exemplary functionalization method to modify the external and/or internal surface of the exemplary nanobowl carrier with different molecules, e.g., to provide a nanobowl carrier body 220 loaded with a payload 230 inside and selectively functionalized to include targeting molecules 225 outside. For example, as shown in FIG. 2, for the interior surface of the exemplary silica nanobowl body 120, alkoxysilane chemistry can be used to interface a wide variety of molecular cargo or payloads, e.g., such as molecules including drugs or contrast agents. FIG. 3 shows a diagram of an example for maleimide functionalization with thiol containing silane for interfacing with the silica. Referring to FIG. 2, for example, for the exterior surface of the exemplary silica nanobowl body 120, any molecule with a free sulfhydryl or amine can be used to attach to the surface of the exemplary gold coating spontaneously. This can be used for attachment of passivation agents like polyethylene glycol or targeting moieties, for example. As shown in the example of FIG. 2, the nanobowl carrier body 220 can include a functionalization layer 211 on the external surface of the nanobowl carrier body 220 (e.g., the outer surface of the exemplary gold coating 115) to attach the targeting agents 225 or passivation agents.

The disclosed nanobowl can be structured to include a lid (e.g., cap) to contain the molecular cargo or payloads, which can be controllably opened when needed using external stimuli. In some embodiments, for example, the cap can be created using DNA origami, a liposome or a polymer that completely encapsulates and wraps the particle. In some embodiments, for example, the cap can be selectively placed over the cavity of the nanobowl to seal off the nano-carrier with the exemplary cargo (e.g., any drugs, contrast agents, etc.) trapped inside. FIGS. 4A and 4B illustrate exemplary laser-assisted or RF-assisted heating techniques to controllably open and close the cap. The nanobowl carrier can release the payload in its vicinity. In some implementations, this can involve tethering of the cap (e.g., a capping particle) with DNA. For example, the melting point of DNA is highly adjustable based on nucleotide composition and length. Using an exemplary capping particle of ~50 nm in size, and using complementary strands of DNA linked to the nanobowl structure of the carrier and the capping particle, a plug or seal can be created that is thermally responsive. Alternatively, for example, a liposome can be used to seal off the particle as well.

Examples are shown in FIGS. 3, 4A and 4B of exemplary nanobowls' surfaces (FIG. 3) and exemplary carriers' cap structures and attachment mechanisms (FIGS. 4A and 4B) to the nanobowl structure for controllably opening/closing the carrier to load and release the cargo to and from the nanobowl's interior. For example, a cargo or payload 230 (e.g., a drug, contrast agent, or other type cargo) is shown in FIG. 3 to be functionalized to the nanobowl carrier body's 220 interior region, e.g., functionalized to the interior surface of the exemplary silica nanobowl particle 111. For differential functionalization, the interior of the nanobowl carrier body 220 can be modified using a drug or contrast agent. One such example for linkage is the modification of the drug (monomethylauristatin E, MMAE) with an alkoxysilane, shown in FIG. 3. Also, for example, a capped nanobowl carrier can be implemented to enclose the drug in the interior and controllably open the cap structure to allow release of drug. A payload/cargo can be loaded into the interior cavity of the exemplary nanobowl carrier body 220 and sealed by an exemplary capping particle that can be attached and controllably actuated to open and close by an external stimulus. In some examples, the payload (e.g., drug) can be loaded into the nanobowl carrier body (e.g., incubation of the nanobowl with a high concentration of the desired payload), and the capping particle can attach to the nanobowl and seal the opening (e.g., enclosing the payload within the interior region) by self-assembly of self-assembled monolayer (SAM) or other type functionalization layer of the capping particle to the nanobowl. In other examples, the capping particle can attach to the nanobowl and seal the opening (e.g., enclosing the payload within the interior region) by a DNA switch, in which the DNA is switched "ON" to an OPEN position to allow the payload to diffuse into the cavity, and in which the DNA is switched "OFF" to a CLOSED position to seal the payload inside the nanobowl.

Controllably Releasing a Payload from Nanobowl Carriers

In implementations, for example, the disclosed nanobowl carriers can be operated using any of multiple mechanisms to attach cargo/payloads (e.g., molecules) to the nano-carrier and release the cargo/payloads (e.g., molecules) from the nano-carrier. In the exemplary embodiments of the nanobowl carrier including an internally functionalized cargo/payload molecules (e.g., drugs, contrast agent, etc.), a chemical linker can interface the active molecule to the interior region of the nanobowl structure (e.g., silica, etc.). In the example case of MMAE, it is held to the exemplary silica interior by an enzymatically sensitive dipeptide linker (valine-citruline) found intracellularly. Other chemical linkers can be used that are sensitive to enzymes outside the cell, so that it can release its payload there as well. Additional chemical linkers sensitive to light, pH, and temperature can be used as well, so that the chemical linkers release the payload on demand.

In the exemplary embodiments of the nano-carrier including a cap or lid configuration, the nano-carrier can be structured to functionally respond to an external stimuli such as RF heating of the magnetic nanoparticles or near infrared (NIR) heating of the gold shell, for example, to melt the cap off (as illustrated in FIG. 4A) or actuate a DNA switch/latch to open (as illustrated in FIG. 4B). When the heat is removed, for example, the DNA switch is closed and shutting off diffusion of a therapeutic out of the capsule. Alternative methods for activating the switch can include DNA displacement using another DNA strand, or interactions with other chemical moieties.

FIG. 4A shows an illustrative diagram of an exemplary nanobowl carrier 400A loaded with the payload 230 in the interior region of the nanobowl carrier body 220 in which a capping particle 420 (e.g., gold nanoparticle) is sealed against the opening, such that the payload 230 is encased within the nanobowl carrier 400A and cannot leak out of the nanobowl carrier 400A. In this exemplary embodiment of the nanobowl carrier, the capping particle 420 includes a functionalization layer 411, e.g., such as a nucleic acid having a particular nucleotide sequence, on the external surface of the capping particle 420, which is configured to attach a complementary strand 415, e.g., such as a DNA strand having a complement nucleotide sequence functionalized to the interior region of the nanobowl carrier body 220, e.g., via an alkoxysilane linkage. The functionalization layer 411 including the nucleotide sequence and the complementary strand 415 of the nanobowl carrier 400A can form a molecular hinges (e.g., nucleic acids, such as DNA) attached to the silica interior region of the nanobowl carrier body 220 and to the capping particle 420 to bind the capping particle 420 to the nanobowl carrier body 220, which can be controllably opened based on an external stimulus. As shown in the diagram of FIG. 4A, when an external stimulus (e.g., such as an optical stimulus (e.g. laser), RF stimulus, or other) is applied to the nanobowl carrier 400A to cause excitement of the nanoparticles 113 and/or gold coating 115 that produces heat, such that the molecular hinges 415 melt to thereby release the capping particle 420 and allow for release of the payload 230'.

FIG. 4B shows an illustrative diagram of an exemplary nanobowl carrier 400B loaded with the payload 230 in the interior region of the nanobowl carrier body 220 in which the capping particle 420 (e.g. gold nanoparticle) is sealed against the opening using a switchable latch structure 440, such that the payload 230 is encased within the nanobowl carrier 400B and cannot leak out of the nanobowl carrier 400B. In this exemplary embodiment of the nanobowl carrier, the capping particle 420 includes the switchable latch structure 440 attached to the capping particle 420 the silica interior region of the nanobowl carrier body 220. In some implementations, for example, the switchable latch structure 440 includes a molecular zipper and spring device, e.g., such as a DNA zipper spring actuator device. Examples of the molecular zipper and spring device are described in U.S. Patent Publication No. 2014/0080198 A1, the entire contents of which are incorporated by reference as part of the disclosure of this patent document. For example, the opening can be controllably blocked by an exemplary molecular zipper/spring actuator 440 coupled to the capping particle 420 to provide a nanoparticle gating mechanism that can open and detach, or close to reseal the opening, when a specific stimulus (e.g., a complementary nucleotide sequence) is recognized by the nanobowl carrier 400B. The switchable latch structure 440 is able to unzip such that a portion of it extends to unseal the capping particle 420 from the opening, thereby allowing the payload 230' to release from the nanobowl carrier 400B. In other implementations, for example, the capping particle 420 of the nanobowl carrier 400B can be opened by applying external radiation (e.g., near infrared heating of the gold shell 115, RF heating of the iron oxide nanoparticles 113 and/or the gold shell 115). Such heating can be produced by the applied radiation such that the exemplary molecular zipper/spring actuator 440 can open, and removal of the heating can close the zipper and reseal the particle.

The exemplary molecular zipper/spring actuator 440 is covalently attached on one arm to a nanoparticle (i.e., the capping particle 420) that is large enough to block the opening of the nanobowl carrier body 220. On the other end, the exemplary molecular zipper/spring actuator 440 is covalently attached to the interior of the nanobowl carrier body 220 (e.g., at the bottom of the interior region). The molecular sequence of the zipper structure of the actuator 440 can be designed to be complementary to a certain sequence of a nucleotide or of the RNA or DNA of a virus. Upon recognition of this specific strand, the zipper would unravel and unblock the opening in the capsule. In one application, for example, the payload 230 can include antiviral agents that are loaded into the nanobowl carrier body 220 and would thus be released into the cell to treat the viral infection when the nanobowl carrier 400B encounters a virus having the complementary sequence to the molecular zipper/spring actuator 440.

FIG. 4C shows a diagram of an example of the switchable latch structure 440 when configured as the molecular zipper/spring actuator in a closed, opened, and detached state. The example nanobowl carrier in the closed state 491 includes the exemplary molecular zipper/spring actuator attached by one arm to the capping particle 420 and by the other arm to the interior of the nanobowl carrier body 220, with the complementary sequences of the zipper structure coupled, such that the opening to the interior region is completely blocked and sealed by the capping particle 420. Upon recognition of the complementary nucleotide sequence (e.g., viral or other oligonucleotide) as shown in the open state 492, the zipper unwinds and the nanoparticle unblocks the opening of the capsule allowing interior payload to be released. Alternatively to winding again and causing the nanobowl carrier to be in the closed state, for example, the molecular zipper/spring actuator can be configured to detach the coupled arm to the capping particle 420 when hybridizing with the complementary nucleotide, as shown in the detached state 493, such that the capping particle 420 is completely detached from the nanobowl carrier and the payload is released.

In the example embodiments shown in the illustrative diagrams of FIGS. 4A and 4B, the nanobowl carriers 400A and 400B are structured to include a single opening with a single capping particle 420 to seal against the opening and enclose the payload 230 inside the interior region of the carrier. In other exemplary embodiments, for example, the nanobowl carriers 400A and 400B can include a plurality of openings on the nanobowl carrier body 120 formed by using a plurality of core particles 112 during fabrication, e.g., using the method 100; and the nanobowl carriers 400A and 400B can include a plurality of capping particles 420 and actuatable release mechanisms (e.g., the molecular hinge structure 415 or switchable latch structure 440) to seal against the corresponding openings and enclose the payload 230 inside the interior region of the carrier.

Targeting of Nanobowl Carriers to Specific Cells

The nano-carriers can be targeted to specific cells by attachment of a targeting molecule on the outside of the particle. In some examples using a gold coating (e.g., gold filler and/or plating layer of the exemplary nanobowl structure), this can be accomplished by using any targeting molecule with a free sulfhydryl or amine group. The sulfhydryl and amine groups will spontaneously form a strong bond with the gold surface. The external surface can also be modified with passivation ligands like polyethylene glycol to improve circulation time in the bloodstream.

Magnetic Guidance of Nanobowl Carriers

In some implementations, for example, a strong external magnet can be placed over the bodily region of interest and nanobowl carriers injected intravenously will preferentially collect in the local tissue near the magnet. For example, this is particularly useful in difficult to access regions such as the brain or deep cancer tumors. FIG. 5 shows an illustration of an exemplary implementation of exemplary nanobowl carriers (e.g., such as the nanobowl carriers 400A or 400B), in which a strong magnet can preferentially pull the exemplary magnetically responsive nanobowls out of the bloodstream and into the tissue of interest.

Exemplary Fabrication Methods for Nanobowl Synthesis and Functionalization

Figure 6:
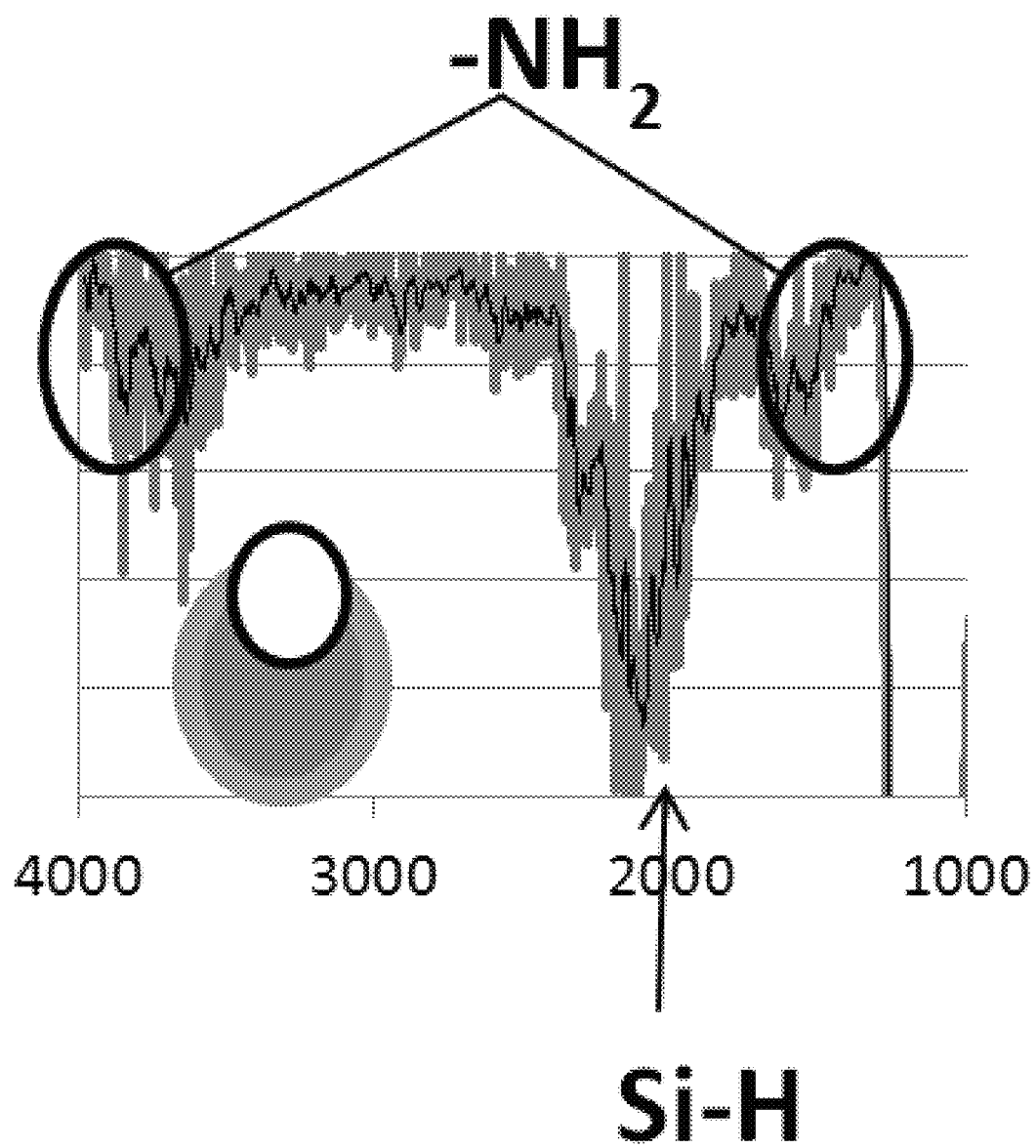
FIG. 6 shows an FTIR spectrum plot of exemplary modified silica nanoparticles.
Figure 7:
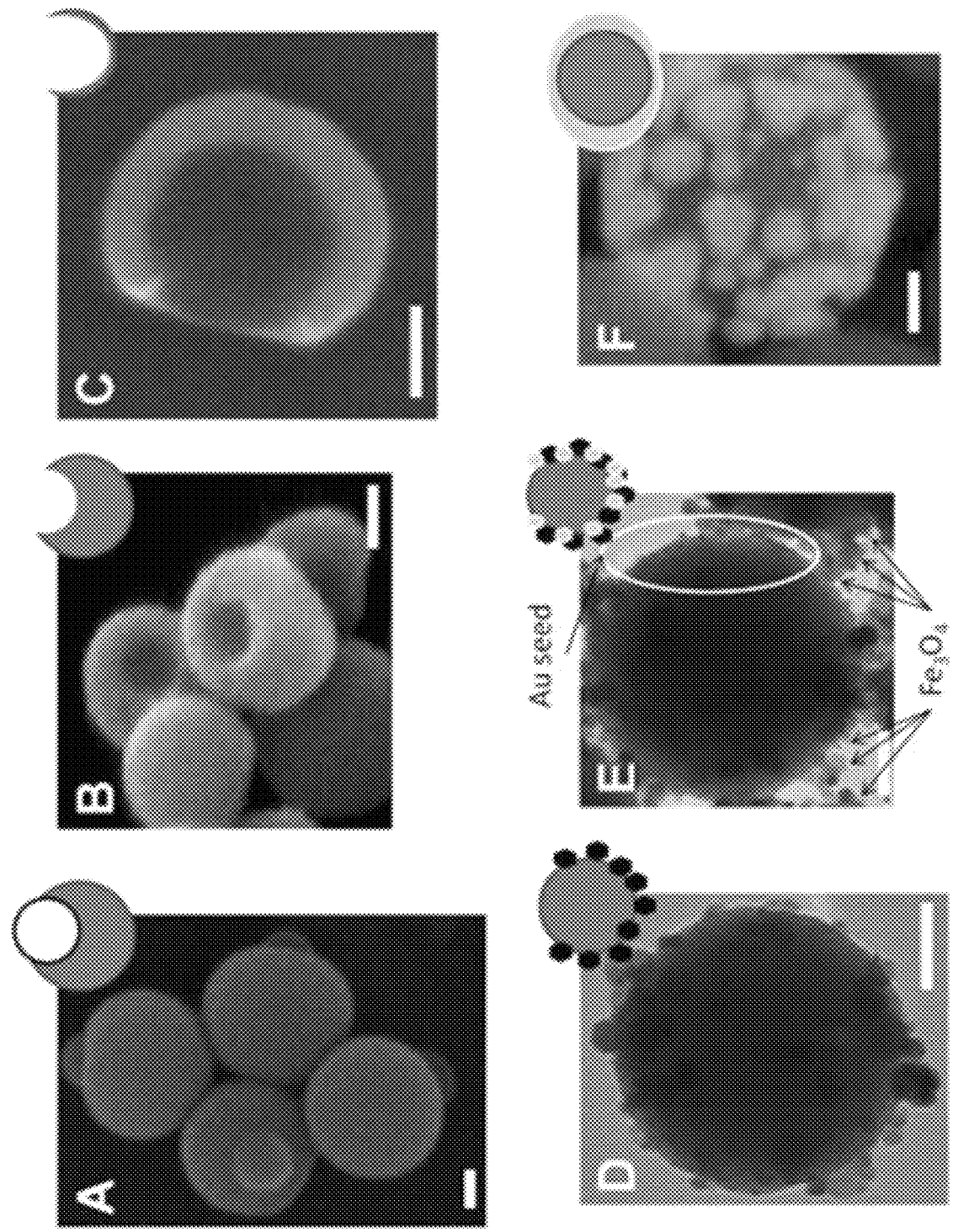
FIG. 7 shows images of exemplary results produced in exemplary implementations of fabrication processes of the disclosed technology.

In some implementations, the disclosed fabrication methods can include synthesis techniques to produce magnetically-sensitive gold nanobowl structures using solution-based processes that can be implemented to create a particle with two chemically distinct surfaces that can be functionalized, as shown in FIG. 1. Exemplary implementations of an exemplary fabrication method were performed, and some exemplary results are shown in FIGS. 6 and 7. FIG. 6 shows an FTIR spectrum plot of exemplary (N-(2-aminoethyl)-3-aminopropyl)trimethoxysilane (AEAPTMS) modified silica nanoparticles. FIG. 7 shows exemplary images depicting the results of implementing exemplary fabrication processes and characterizing the products of such processes individually (e.g., scale bars of FIG. 7 represent 50 nm).

The exemplary implementations of the fabrication method included using a silica/polystyrene template to synthesize the nanobowl structure. For example, in a glass vial with a magnetic stir bar, a solution of deionized (DI) water, anhydrous isopropanol, and ammonium hydroxide was prepared. To this solution, carboxylated polystyrene (PS, 100 nm) and tetraethylorthosilicate (TEOS) was added at the same time in a vigorously stirred solution. The solution was stirred for 2 hrs. The solution was then washed by centrifuge for 7 min at 1000 g and the pellet was re-suspended in isopropanol twice and DI water twice. Final dispersion was performed in 2 mL of water.

The exemplary implementations of the fabrication method included a silica amine surface functionalization technique. For example, (N-(2-aminoethyl)-3-aminopropyl)

trimethoxysilane (AEAPTMS) was added to anhydrous ethanol to form a 1% (v/v) solution. A certain amount of the $SiO_2$/PS template was added to the solution and the functionalization progressed for 2 hrs. Afterwards the particles were washed in anhydrous ethanol and DI water twice. After the final wash, the particles were re-suspended in 2 mL of DI water.

The exemplary implementations of the fabrication method included attaching iron oxide nanoparticles to the carrier. For example, iron oxide synthesis included reacting a mixture of $FeCl_3.6H_2O$ and $FeCl_2.4H_2O$ with ammonium hydroxide under nitrogen gas at 80° C., and then the solution was allowed to react for 1.5 hours after the addition of oleic acid. The magnetite nanoparticles fabricated were washed with deionized water until neutral pH. For example, the iron oxide stabilization (with citrate) included spinning oleic acid coated nanoparticles in water, and the water was decanted. The particles were then suspended mixture of citric acid, chloroform and N,N-dimethyl formamide (DMF). The mixture was then stirred at 90° C. for 12 hours in an oil bath. The particles were pulled from the oil bath and allowed to cool to room temperature. The particles were subsequently precipitated by the addition of ethanol separated using a magnet. The particles were re-dispersed in acetone and again separated by means of a magnet 3 to 4 times to remove all traces of free citric acid. Citrate modified particles were re-suspended in DI water. For example, the iron oxide nanoparticle seeding to the template particle structure included stirring together amine modified template particle solution and citrate modified iron oxide solution at 45° C. for at least 30 min. To remove excess free iron oxide nanoparticles from the mixture, the solution was centrifuged at repeated at least 2 times. An image showing exemplary results of iron oxide attachment on positively charged 200 nm $SiO_2$ is shown in FIG. 7, panel D.

The exemplary implementations of the fabrication method included seeding gold to the carrier. For example, preparation of a gold seed solution included the following. A basic solution of water, sodium hydroxide (NaOH) and chloroauric acid ($HAuCl_4$) were reduced by a concentrated solution of tetrakis(hydroxymethyl)phosphonium chloride (THPC) while stirring. The solution was aged for 24 hours at 4° C. in refrigeration before use to create 5 nm size gold seeds. For example, the gold seeding of the nanobowl template included attaching gold nanoparticles to the template particles, in which the amine-modified template particle solution and colloidal gold solution were stirred at 45° C. for at least 30 min. To remove excess free the solution was centrifuged and washed least 4 times. When successful, for example, a deep red precipitate is typically formed and re-dispersed in DI water.

The exemplary implementations of the fabrication method included forming an external coating to the carrier by gold plating. For example, gold plating solution was prepared by mixing $K_2CO_3$, $HAuCl_4$, DI water, and overnight in the dark at 4° C. This transforms the chloroauric acid into a gold hydroxide solution. A certain amount of gold seeded template particles were added to a similar amount of equivalent chloroauric acid. Formaldehyde was added to the gold plating solution to initiate plating. The plating was allowed to proceed for 30 minutes; during this time the solution went from clear to a deep purple. The particles were then washed 4 times with DI water to remove the excess gold ions and re-dispersed in 2 mL of DI water.

The exemplary implementations of the fabrication method included removal of the core particle from the carrier structure. For example, the template particles were placed in an excess of tetrahydrofuran (THF) at room temperature (RT) for 2 days. The particles were then washed in water to remove traces of THF.

The exemplary implementations of the fabrication method included removal of a portion of the carrier structure. For example, an internal cavity of the carrier was formed by etching. After the polystyrene was dissolved, the carrier can be etched via NaOH to form the nanobowl structures, in which the functionalized silica nanobowl structures were placed in a 1 M NaOH solution for 1 hour, and subsequently, the NaOH was neutralized using HCl.

The images of FIG. 7 demonstrate exemplary results of implementations of the various processes of the exemplary fabrication method employed. The exemplary silica/polystyrene ($SiO_2$/PS) template particle synthesis and its subsequent modification with an amine (e.g., in which exemplary characterization results are shown in FIG. 6) can be readily reproduced. The exemplary $SiO_2$/PS template particles were produced to be 180-200 nm in diameter, as shown in panel A of FIG. 7. As demonstrated by the FTIR spectrum shown in FIG. 6, the silica on the template was successfully modified with signs of both silica and amine. As shown in FIG. 7, panel B, the particles were treated with DMF leaving a cavity behind where the polystyrene particle used to be. The interior cavities can be further etched open using NaOH, as shown in the image of panel C, FIG. 7. Attachment of iron oxide and gold were first tested on an amine modified, commercially bought, 200 nm $SiO_2$ to see if they could be co seeded. The particles previously seeded with iron oxide (FIG. 7, panel D) were than incubated with gold seeds. FIG. 7, panel E shows this dual seeding. In some implementations, the gold plated silica particles can be configured to be uniform, whereas in others, to be patchy, as shown in FIG. 7, panel F.

Exemplary Release of Surface Functionalized Moieties from the Exemplary Nanobowl Once the nanobowl carrier has been synthesized, they can be loaded with any of a variety of molecular payloads such as a drug and functionalized with a targeting moiety onto the chemically distinct surfaces of the nanostructure. In the exemplary case of the targeting molecule CPE and drug MMAE, these molecules can easily be modified. For example, this can be done with a Valine Citruline (VC) dipeptide linker that is enzyme cleavable intracellularly. Alternatively, for example, a linker that is sensitive to extracellular peptides can also be used to release the drug.

Surfaces Linkage: For the internal functionalization of the silica surface, the maleimide-sulfur chemistry for the exemplary Mal-vc-MMAE-CPE linkage is used here as well by substituting for the sulfhydryl containing silane, mercaptopropyltrimethoxysilane (MPTS), as shown in FIG. 3. The MPTS can be added in excess to ensure complete attachment of the MPTS to the vcMMAE. This kind of silane functionalization strategy can be used to functionalize fluorophores before attachment to silica. For the external functionalization, the exemplary targeting agent $CPE_{290-319}$ can be custom synthesized with a cysteine at the C-terminus of the peptide. This sulfhydryl can readily attach to gold in aqueous conditions. Functionalization can first start with $CPE_{290-319}$ in excess of the maximum number of CPE peptides that can be squeezed onto the surface of the particle. After centrifuging and washing, the particles can then be incubated with the MPTS-Mal-vc-MMAE. This linkage can be done in ethanol.

Cell Targeting: Endocytosis of the conjugate can be confirmed with immunohistochemistry of treated cells with anti-CPE antibody. Internalized $CPE_{290-319}$ will show up in the cell's cytosol on a fluorescence microscope. For testing of cytotoxicity, for example, the human ovarian cancer cell lines 2008 and OVCAR-3 overexpress claudin-3 and -4 proteins and different amounts of conjugate can be used to test therapeutic efficacy. Knockdowns of claudin-3 and claudin-4 in 2008 cells can allow for negative controls. In addition, the conjugate can be compared to free MMAE and free $CPE_{290-319}$. At multiple time points up to 96 hours the effects of the $CPE_{290-319}$-vc-MMAE conjugate, free MMAE, and free $CPE_{290-319}$ on the tumor cells in culture can be evaluated using the Cell Counting Kit-8 assay. For example, for knockdown creation, the following can be implemented. 2008 cells can be treated with shRNAi delivered with lentiviral constructs to either knock down claudin-3 or -4. Knockdown of both proteins simultaneously can result in cell death. Verification of knockdown via mRNA expression and protein expression can be accomplished with reverse transcriptase PCR and Western blots. For example, for conjugate stability, the following can be implemented. The conjugate's stability can be tested by incubating the conjugate in PBS and checking for degradation products at different time intervals. In addition linker functionality can be tested by incubating the linker with cathepsin-B and checked for separated MMAE using LC/MS. Cell death mechanisms can include the following. For example, MMAE is a highly potent tubulin binder. A western blot can examine the ratio of free tubulin to microtubule in $CPE_{290-319}$-vc-MMAE treated cells versus untreated cells to confirm MMAE is targeting the intended proteins to induce apoptosis. In some implementations, for example, the localization of particles can be implemented with magnet. For example, a strong magnet will be used to localize particles to a certain location in the petri dish.

Exemplary Capping of the Exemplary Nanobowl Structures

Capping of the exemplary nanobowl body can be implemented using any of multiple strategies. For example, such capping can include irreversible opening of the nanobowl, and reversible opening of the nanobowl, as well as with a liposome.

Exemplary DNA linked Gold Particle as Capping Particle: The nanobowl-capping particle can include a gold particle functionalized with DNA to create densely functionalized DNA particles. In some examples, it involves using ~20 nucleotide, thiol modified DNA for the initial functionalization. The salt concentration can then be raised to lower electrostatic repulsion due to the phosphates on the DNA. A second round of functionalization can be performed to create dense DNA functionalized gold particles. For attachment of DNA to the silica, amine functionalized complimentary DNA can be used. The silica can be functionalized with carboxyl using caroboxyethyl-silantriol monosodium solution. This molecule is reactive to inorganic hydroxyl groups on the silica surface and provides an attachment point for the amine functionalized DNA. EDC/NHS crosslinkers can then be used to link the carboxyl group onto the amine. After these particles are functionalized with DNA, the capping particles and the nanobowls can be incubated together and bind together and form one particle.

Exemplary linkage of the capping particle to the nanobowl body is not limited to DNA or gold particles. Other irreversible linkages may be responsive to chemical or enzymatic degradation. In addition the use of reusable, switchable molecular linkages or motor mechanisms to open and close, a valve can be included as well.

The fabrication techniques can include several points at which characterizations can be performed. One example includes after completion of the DNA linkage, a DNA binding dye like Sybr Green can be used to confirm presence of DNA in the capping particle or nanobowl. Another example includes after the annealing of the capping particle to the nanobowl. This can be demonstrated by comparing annealed cap and nanobowl with the nanobowl and capping particle individually using gel electrophoresis. Additionally individual particles can be imaged with TEM to demonstrate successful combination.

For exemplary payload (e.g., drug) loading, the following can be implemented. For example, before the nanobowl and the cap are being annealed, drugs can be added in high excess and when the nanobowl and cap are annealed, the drug should remain physically trapped in the volume of the nanobowl. Heating of the particles with an RF pulse or NIR laser should heat the particles enough to melt the complementary DNA and thus release the particle. Release can also be accomplished through chemical means, such as interaction with a complementary DNA strand, conformation switching using addition of other peptides, ions, or small molecules.

Exemplary Embodiments of the Disclosed Nanobowls

In some exemplary embodiments of the disclosed technology, the disclosed nanostructure carriers can include asymmetric gold and silica nanobowl structures with magnetic functionality, in which methods for fabricating these exemplary nanostructure carriers can include the following processes. An exemplary fabrication method can include a process to use a core-satellite template to create nanobowls structured to include a single large negatively charged core and many smaller positively charged satellite particles attached to it. Template particles can be used to synthesize porous gold shells. An exemplary fabrication method can include a process to use a positive core and negative satellites to create the nanobowl structures, i.e., a core-satellite template from which the nanobowl structures are synthesized. In the exemplary process, the nanobowl structures can be synthesized specifically around the satellite particles using electrostatic attraction of other materials, e.g., including gold, silica, and/or iron oxide. The exemplary process can include the dissolution of the core-satellite template to release multiple nanobowls from the template.

The disclosed nanostructure carriers can be implemented as delivery systems having a defined enclosure (e.g., a nanoscale bowl-like structure) that can store specific cargo. The disclosed nanostructure carriers can be implemented as delivery systems having pores that prevent passive leakage (e.g., passive diffusion) of the cargo. The disclosed nanostructure carriers can be implemented as delivery systems having a cap that can be opened and closed on-demand. The disclosed nanostructure carriers can be fabricated in a form of an asymmetric bowl nanostructure using a template assisted method of the present technology, in which the exemplary nanobowl structure forms selectively around the satellites of the core-satellite template, e.g., using electrostatic attraction.

FIG. 8 shows a schematic illustration depicting an exemplary fabrication method 800 of disclosed technology to produce exemplary nanobowl structures using a core-satellite template directed process. Various materials can be used to create various nanobowl structures using the exemplary core-satellite template particle-assisted method 800, shown in FIG. 8. Examples of the produced nanobowl structures using the method 800 can include silica nanobowls, gold nanobowls, and a magnetically responsive gold nanobowls. The method 800 includes a process 801 to produce a core-satellite template particle 810 structured to include a larger negatively charged core particle 811 and smaller positively charged satellite particles 812. In some implementations, for example, the process 801 can include mixing the negatively charged core particles and positively charged satellite particles together at a predefined ratio, e.g., less than 1:100 core to satellite particles. For example, 1:100 core to satellite particles provides enough satellites to saturate all core particles. The positively charged satellites 812 can be selectively modified to attract negatively charged molecules or nanoparticles.

The method 800 includes a process 802 to produce silica nanobowl structures 822 based on the produced core-satellite template particle 810. For example, the process 802 can include the growth of an inorganic silica around the positively charged satellite particles 812, and dissolution of the template particles, i.e., the core particle 811 and the satellite particles 812, resulting in multiple synthesized silica nanobowl structures 822. The synthesized silica nanobowl structures 822 include an external silica shell structure and a hollow interior, including an opening to the hollow interior.

The method 800 includes a process 803 to produce gold nanobowl structures 832 based on the produced core-satellite template particle 810. For example, the process 803 can include the formation of gold nanoparticle seeds 831 that are attracted to the satellite particles 812, growing a gold shell 832 on the satellite particles 812 via the gold nanoparticle seeds 831, and dissolving the template particles, i.e., the core particle 811 and the satellite particles 812, to release the gold nanobowl structures 833. The synthesized gold nanobowl structures 833 include an external gold shell and a hollow interior, including an opening to the hollow interior.

Figure 8:
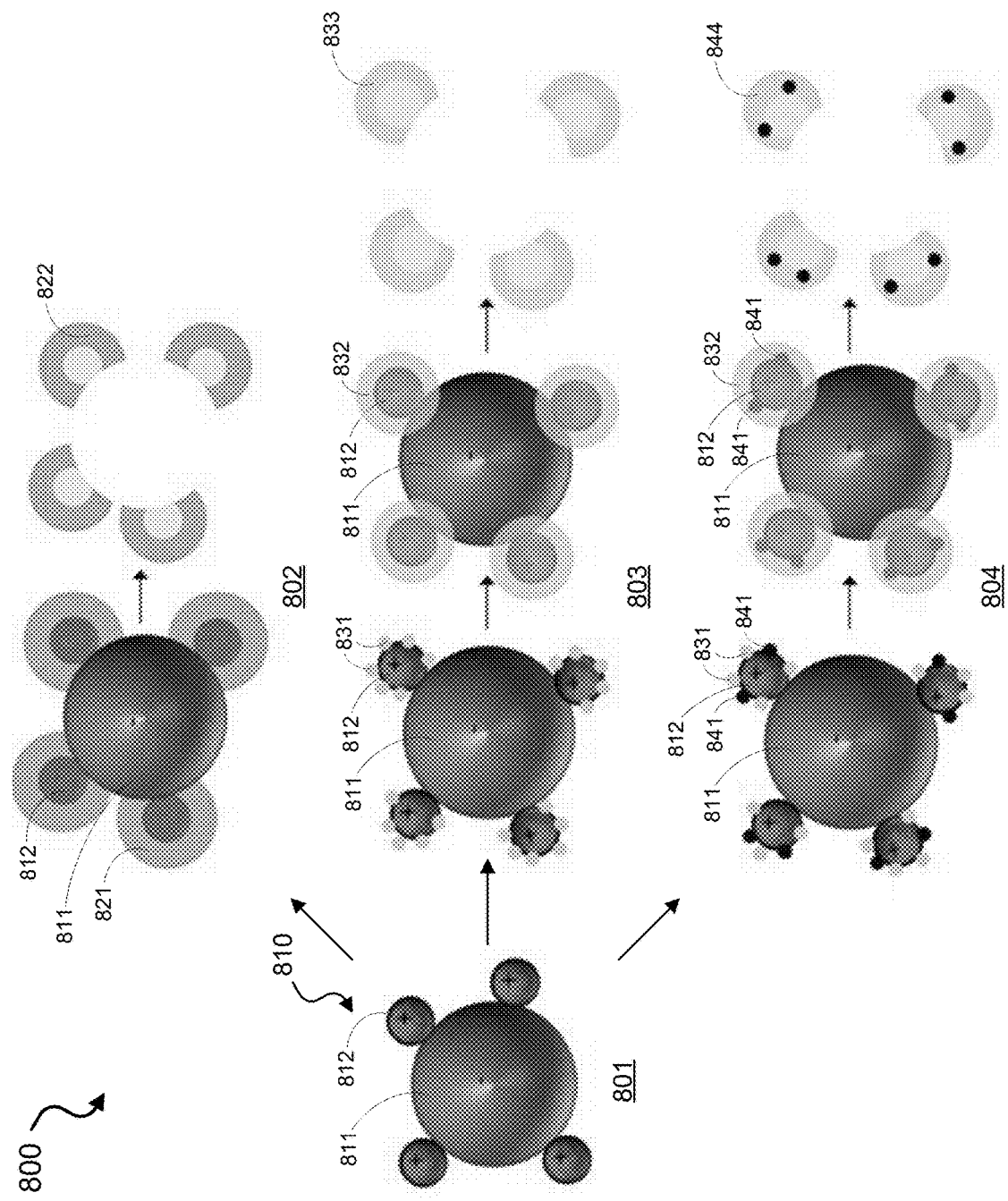
FIG. 8 shows a schematic illustration of an exemplary fabrication method of disclosed technology to produce exemplary nanobowl structures using a template directed process.

The method 800 includes a process 804 to produce magnetically responsive gold nanobowl structures 844 based on the produced core-satellite template particle 810. The process 804 can include attaching iron oxide nanoparticle seeds 841 and gold nanoparticle seeds 831 to the positively charged satellite particles 812. The process 804 can include growing a gold shell 832 on the satellite particles 812 via the gold nanoparticle seeds 831 that embeds the iron oxide nanoparticles 841 within. The process 804 can include dissolving the template particles, i.e., the core particle 811 and the satellite particles 812, to result in the formation of magnetically responsive gold nanobowl structures 844. The synthesized magnetically responsive gold nanobowl structures 844 include an external gold shell with iron oxide nanoparticles embedded in the gold shell, and a hollow interior, including an opening to the hollow interior. It is noted that other materials can be grown and formed using the exemplary fabrication method 800 shown in FIG. 8 to shape and produce the nanobowl structures of the disclosed technology.

FIGS. 9A and 9B show scanning electron microscopy (SEM) images demonstrating materials produced using the disclosed template synthesis fabrication methods from a negative charged 1000 nm polystyrene cores (in FIG. 9A) and positively charged 100 nm (cationic polyelectrolyte functionalized) polystyrene satellites (in FIG. 9B). For example, templates made from purely silica or a mixture of silica and polystyrene can be accomplished as well. FIG. 10 shows SEM images of exemplary fabricated structures with increasing thickness (e.g., left to right) of the silica exterior of nanobowls formed on satellite particles of polystyrene templates, e.g., according to the method shown in FIG. 8. The SEM images of FIG. 10 demonstrate the ability to control the thickness of the silica exterior of the exemplary nanobowls grown on the satellite particles by controlling the silica formation conditions, e.g., such as the amount of TEOS including medium amounts of TEOS (middle image), and large amounts of TEOS (right image).

In some implementations, for example, the exemplary fabrication method can include coating carboxylate-modified polystyrene spheres (e.g., 100 nm diameter) with a cationic polyelectrolyte (e.g., such as poly(diallyldimethylammonium chloride) or poly(allylamine hydrochloride)). The exemplary fabrication method can include electrostatically attracting negatively charged cores (e.g., 1000 nm diameters), e.g., in which the cores can be made of carboxylate-modified polystyrene and silica. The satellite particles can then be seeded and plated with gold, and/or coated with silica or coated with iron oxide.

Figure 11A:
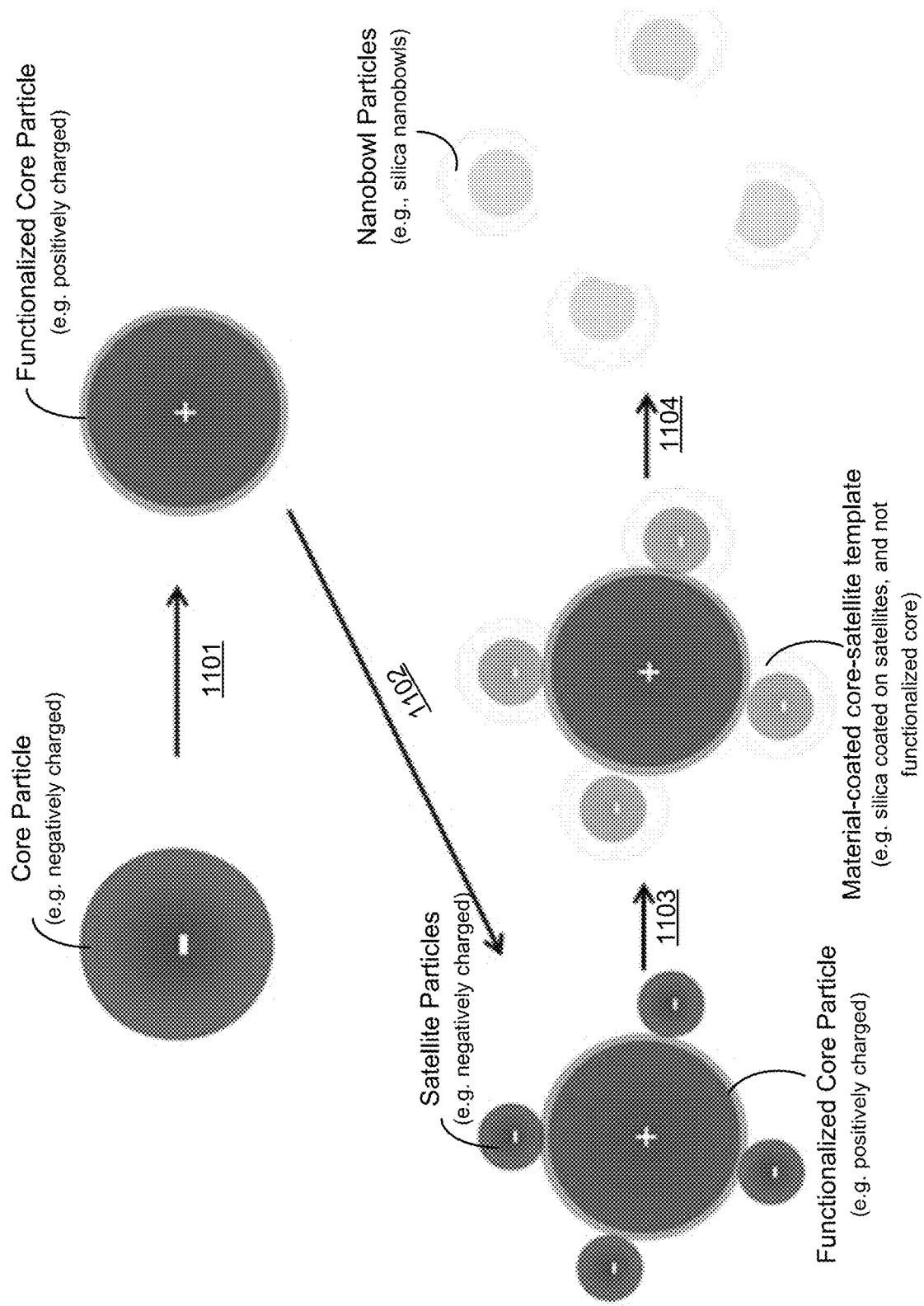
FIG. 11A shows an illustrative diagram of an exemplary fabrication method to produce nanobowl structures using a surface functionalized core and satellite particle template.
Figures 11B, 11C, 11D:
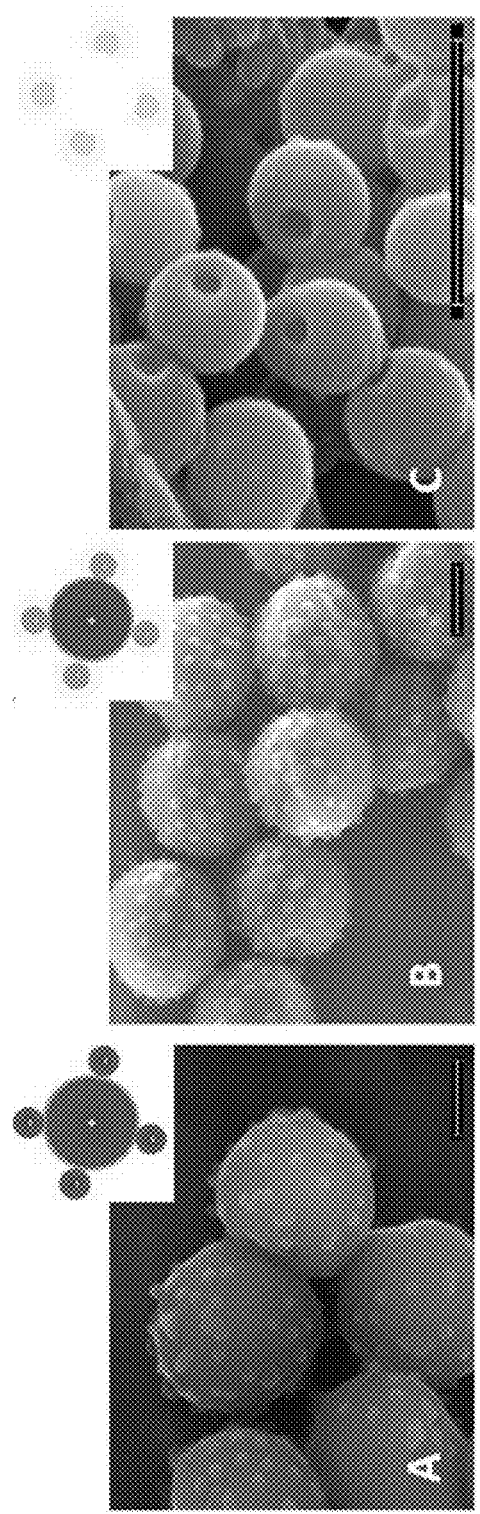
FIGS. 11B-11D show diagrams and associated SEM images of the resultant particles during implementation of an exemplary nanobowl fabrication method.

In some exemplary embodiments of the disclosed technology, the disclosed nanobowl structures can be synthesized using a core-satellite template including a large positively charged core and many smaller negatively charged satellite particles attached to it. FIG. 11A shows an illustrative diagram of one example of a method to produce nanobowl structures (e.g., silica nanobowls) using a surface functionalized core and satellite particle template, which includes the following processes. As shown in FIG. 11A, the method includes a process 1101 to functionalize a negatively charged core particle (e.g., 1 μm polystyrene) with a coating (e.g., polymer coating, such as Polydiallyldimethylammonium chloride (PDDA)) to form a positively charged surface of the core particle. The method includes a process 1102 to attach satellite particles (e.g., 100 nm of negatively charged polystyrene particles (e.g., polystyrene-COOH)). The method includes a process 1103 to react the positively-charged functionalized core and negatively-charged satellite template with positively charged silane to form a shell structure (e.g., silica shell structure), e.g., such as QuATPmS or ATPmS, or other, depending on the surface modification that is desired. The method includes a process 1104 to produce the nanobowl structure by removing the functionalized core—satellite template, e.g., using organic solvent to etch away the polystyrene and the polymer (PDDA) that was coated the core. FIGS. 11B-11D show illustrative diagrams and associated SEM images of the resultant particles during implementation of the exemplary fabrication method. The SEM image (A) shown in FIG. 11B shows 100 nm PS-COOH satellites that were attached to the PDDA-coated polystyrene core by charged interaction. The SEM image (B) shown in FIG. 11C shows the structure or pollen after coating with QuATPmS, e.g., the size of each satellite were increased by 20-30 nm. The SEM image (C) shown in FIG. 11D shows the produced nanobowl structures after an etching process with DMF. The exemplary scale bar in FIGS. 11B-11D represents 500 nm.

The exemplary method includes a process to form a polymer coated template. For example, a specific amount of 1 μm carboxylate-modified polystyrene is diluted in DI water; and to this solution, NH$_4$OH (29%) and Polydiallyldimethylammonium chloride (PDDA) is added respectively in a vigorously stirred solution. The polymer coated template formation process can include allowing a reaction to take place, e.g., for 20 minutes. For example, 500 μL of aqueous 1 μm PS-COOH (2.7% vol/vol) can be diluted in 4.5 mL DI water; then 320 μL of NH4OH (29%) can be added and stirred; and, while stirring, 2.5 mL 1% PDDA can be added and kept on stirring for 20 minutes. The polymer coated template formation process can include washing the solution, e.g., by centrifugation for 15 min at 3200 g, and re-suspending the pellet in DI water thrice and ethanol twice.

The polymer coated template formation process can include a final dispersion in 80% ethanol in DI water.

The exemplary method includes a process to attach satellite particles to the polymer coated template particle. For example, 1 μm PDDA coated carboxylate-modified polystyrene in 80% ethanol can be incubated with specific amount of 100 nm carboxylate-modified polystyrene for 30 minutes. The solution can then be washed thrice by centrifuge for 5 min at 1000 g. The satellite particle attachment process can include a final dispersion was performed in ethanol.

The exemplary method includes a process to functionalize the silica by amine surface functionalization. For example, ethanol can be added to the produced solution. The functionalization process can include stirring the solution vigorously. The functionalization process can include adding a small amount of N-(Trimethoxysilylpropyl)-N,N,N-trimethylammonium chloride, 50% in methanol (QuATPmS) to stirred solution. The functionalization process can include allowing a stirred reaction to take place, e.g., for 2 hours, before heating it up to 60° C., for example, while stirring for another 2 hours. The functionalization process can include washing the reacted solution in DI water by centrifugation, e.g., for 15 min at 3200 g thrice.

The exemplary method includes a process to form a polyelectrolyte coating or a TMOS coating. The exemplary method includes a process to remove the exemplary polystyrene. For example, the template removal process can include placing the template particles in an excess of DMF while stirring and heating at 100° C. for overnight. The template removal process can include centrifuging the sample and re-suspending in DMF, e.g., repeated three times. The template removal process can include washing the particles in water to remove the traces of DMF.

Exemplary Embodiments of the Disclosed Janus Nanoparticles

Colloidal particles with two or more different surface properties (Janus particles) are of interest in catalysis, biological imaging, and drug delivery. Eccentric nanoparticles are a type of Janus particle including a shell that envelops the majority of a template particle, leaving a portion of the template surface exposed. Exemplary embodiments of the disclosed nanostructures and fabrication methods of the present technology are disclosed that include the sol-gel synthesis of eccentric Janus nanoparticles composed of a silica shell around a Janus template (e.g., a carboxylate-modified polystyrene core). Nanoscale bowl-like structures are synthesized after the removal of the polystyrene core by organic solvent. The exemplary Janus templates (e.g., eccentric silica/polystyrene particles) and nanobowl structures can be used as a versatile platform for site-specific functionalization or theranostic delivery.

Colloidal particles with two or more unique surface chemistries can be referred to as Janus particles, e.g., named after the two-faced god of Roman mythology. The combination of multiple surface chemistries can create a material with its own unique properties. Janus particles can have wide applications in catalysis, biomedical imaging, and drug delivery.

The disclosed technology includes sol-gel, non-microemulsion methods for controlled synthesis of an eccentric silica particle with a silica shell (e.g., referred to as nanoscale olive particles or 'olives;') encapsulating a Janus template (e.g., a carboxylate-modified polystyrene core). The disclosed methods include fabrication of silica nanoparticles (sol-gel) and can include the addition of carboxyl modified polystyrene. Exemplary implementations of the disclosed fabrication method is described, showing the effect of polystyrene template size, surface functionalization, and tetraethylorthosilicate (TEOS) concentration on the Janus template-like particle morphology, and showing exemplary synthesized nanobowl structures after removal of the polystyrene core by organic solvent. The nanobowls can be engineered to have a cavity or hollow interior region that can be used for storage of payloads (e.g., therapeutics), and which can be capped with a biocompatible material structure in implementations for efficient and controlled delivery and release of theranostics (e.g., imaging contrast molecules and therapeutics).

Exemplary methods and materials utilized in the example implementations were as follows. For example, materials included the following. Spherical colloidal polystyrene with carboxylate (PS-COOH) modified surfaces of 50 nm (actual 45±6.2 nm) diameters, 2.6% in water; 100 nm (actual: 85±6.7 nm) diameters, 2.62% in water; and 200 nm (actual: 190±6.5 nm) diameters, 2.65% in water were obtained. Polystyrene with amine ($PS-NH_2$) modified surfaces 200 nm (actual: 230 nm±16.1) diameter, 2.5% in water; sulfate ($PS-SO_4$) modified surfaces, 2.65% in water, 200 nm (actual 194±9 nm) diameter and hydroxyl (PS-OH) modified surfaces 200 nm diameter (actual 190±16.1 nm) 2.6% in water, were obtained. Ammonium hydroxide ($NH_4OH$, 29.79%), dimethylformamide (DMF), TEOS (98%), and anhydrous isopropanol (IPA) were obtained. Deionized water used in all exemplary implementations was produced using a Millipore Advantage A10 system with a resistance of 18.2 MΩ.

For example, the example particle formation processes were as follows. The silica olives were synthesized in 20 mL glass scintillation vials with 700 μL of $H_2O$, 4 mL of IPA and 1.3 mL of $NH_4OH$. To this mixture 100 μL of polystyrene spheres and 83 μL of TEOS (60 mM) were simultaneously added while stirring (unless stated otherwise). The solutions were allowed to react for 2 hours prior to reaction termination by centrifugation (unless stated otherwise). Reaction mixtures were centrifuged for 5 min at 500 g; the supernatant was transferred (the pellet discarded) to a fresh 15 mL centrifuge tube and centrifuged at or greater than 3000 g for 5 min (e.g., 3221 g for 5 min). The resulting pellet was we dispersed in ~15 mL of IPA. The particles were washed by centrifugation twice in IPA (e.g., at 3221 g) prior being re-dispersed and washed twice in $H_2O$ (e.g., by centrifugation at 3221 g).

For example, determination of the particle diameter and imaging techniques were as follows. Particle diameters were measured using either dynamic light scattering (DLS) or by averaging 100 measurements from SEM images. For example, a Brookhaven ZetaPlus DLS instrument was used to measure particle dimensions in solution. Each sample was measured five times to obtain an average signal. The largest majority peak is reported. Histograms were obtained from DLS or SEM measurements and plotted using OriginPro 7.0. For imaging, for example, samples were sputter coated with palladium to improve imaging, e.g., using an Emitech K575X Sputter Coater. SEM images were obtained using an FEI XL30 fitted with an FEI Sirion column to enable ultra-high resolution.

Figure 12:
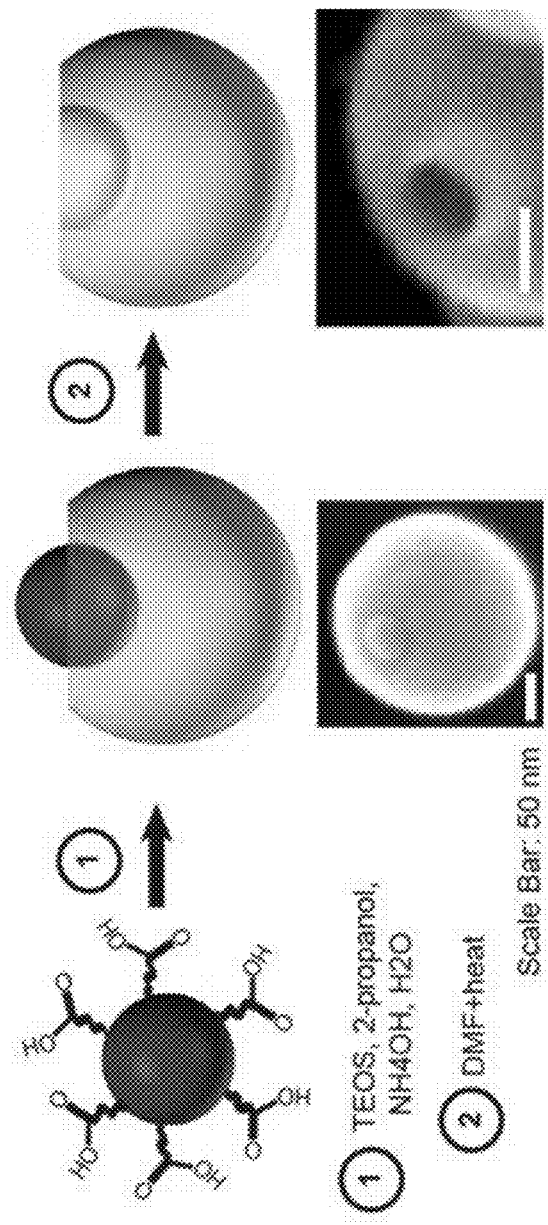
FIG. 12 shows a schematic illustration of an exemplary fabrication method to produce silica olive-like nanostructures.
Figure 13A:
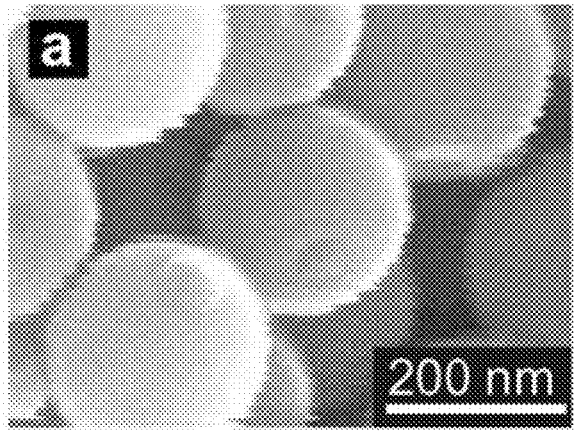
FIGS. 13A-13D show SEM images of exemplary eccentric silica/polystyrene particles produced with 60 mM TEOS over different reaction times.
Figure 13B:
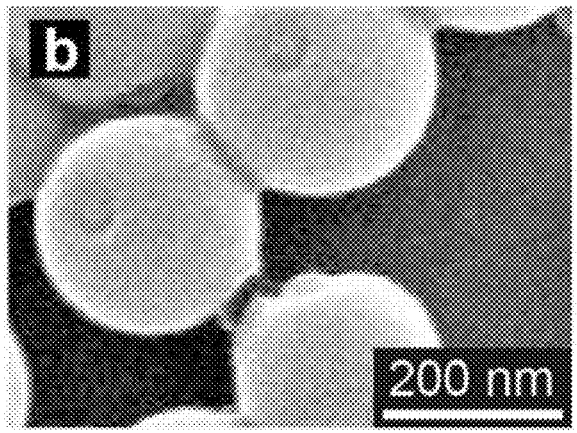
Figure 13C:
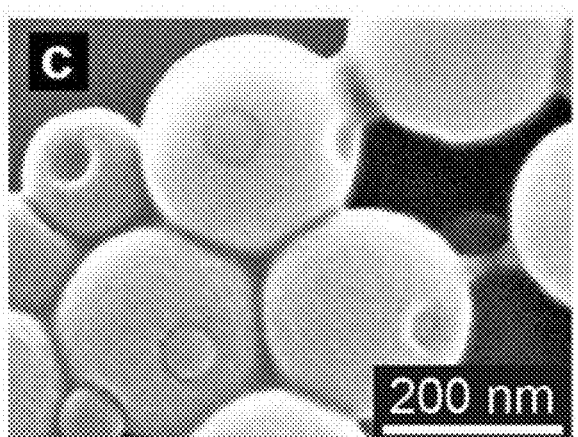
Figure 13D:
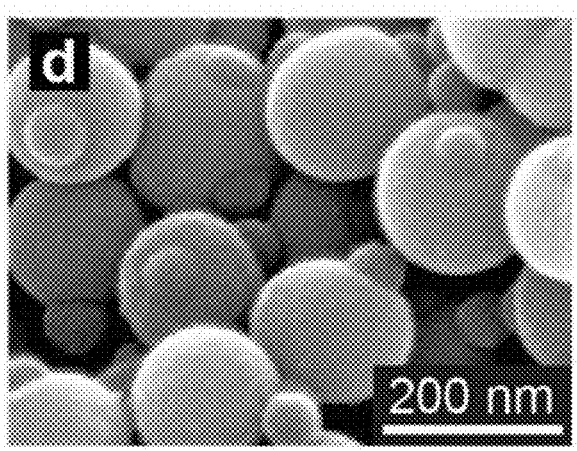

The exemplary results of the example implementations were as follows. FIG. 12 shows a schematic illustration of exemplary eccentric silica/polystyrene particles (e.g., silica nanoscale olives) fabricated using carboxylated polystyrene nanoparticles (PS-COOH) at the start of the reaction, and using a solution of ammonium hydroxide, IPA, DI water, with addition of TEOS and PS-COOH, silica condensed around the PS-COOH in an eccentric fashion. An excess of PS-COOH yielded olives with one or more templates embedded in the silica. The templates were removed using an organic solvent (e.g., DMF) to create a silica nanobowl structure (e.g., an olive without the polystyrene template). In the exemplary implementations, for example, the actual formation of the olives occurred rather quickly, e.g., within the first 15-20 minutes, and the reaction transitioned from a translucent solution to an opaque white one. Additional processing time did not affect the morphology of the olives; it only allowed time to solidify the particle and did not cover up the exposed polystyrene. Olives were observed under the SEM for as long as 18 hr reaction period. The reaction was usually terminated after 2 hr, e.g., which ensured that aggregates did not form. FIGS. 13A-13D show SEM images of exemplary eccentric silica/polystyrene particles produced with 60 mM TEOS after 1 hr (FIG. 13A), 2 hr (FIG. 13B), 3 hr (FIG. 13C), and 18 hr (FIG. 13D) in reaction solution. The polystyrene template remains partially exposed at all times.

Figure 14A:
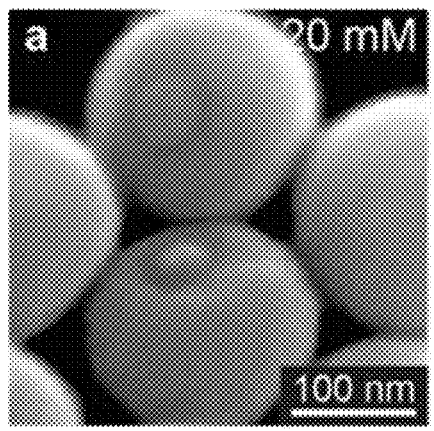
FIGS. 14A-14E show SEM images of exemplary nanoscale olive structures formed using different TEOS concentrations.
Figure 14B:
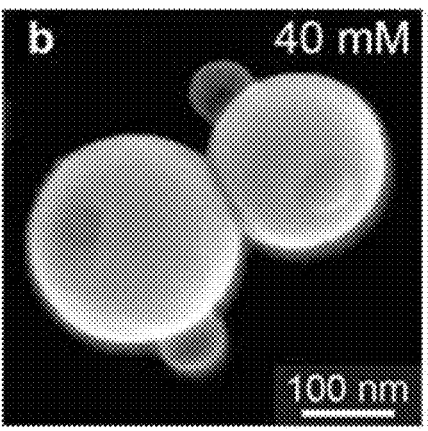
Figure 14C:
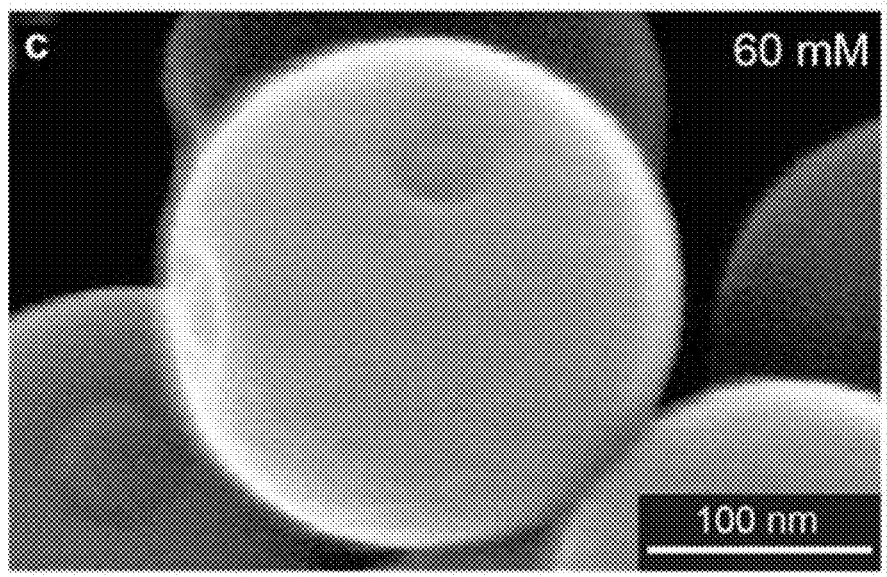
Figure 14D:
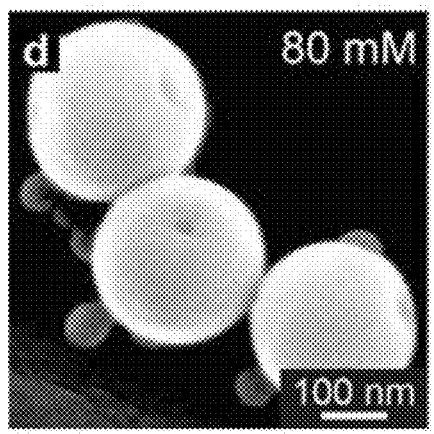
Figure 14E:
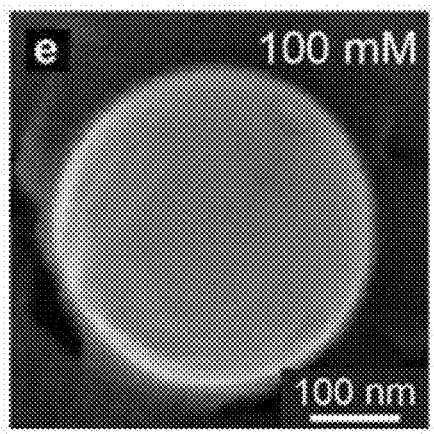

FIGS. 14A-14E show SEM images of exemplary nanoscale olive structures formed using different TEOS concentrations, e.g., holding all other reactants constant. The exemplary images show two trends that emerged from the increasing TEOS concentration, e.g., (i) increasing olive diameter, and (ii) increasing coverage of the polystyrene by the silica. The following TEOS concentrations were used to form olives. Each exemplary fabrication condition's average olive diameter and coefficient of variance included: (a) 20 mM (222 nm, 0.15), as shown in FIG. 14A; (b) 40 mM (206 nm, 0.08), as shown in FIG. 14B; (c) 60 mM (244 nm, 0.15), as shown in FIG. 14C; (d) 80 mM (298 nm, 0.18), as shown in FIG. 14D; and (e) 100 mM (539 nm, 0.34) as shown in FIG. 14E. For example, adjusting the TEOS concentration while holding everything else the same changed how much the silica envelops the PS-COOH. As the TEOS concentration and silica coverage of the polystyrene increased, so did the particle size as measured by DLS, as shown in FIG. 14A. At low TEOS concentrations (e.g., 20 mM, 40 mM), half to three quarters of the polystyrene surface was enveloped by the silica. At higher concentrations (e.g., 80 mM, 100 mM), the silica almost engulfed the polystyrene.

Figure 15A:
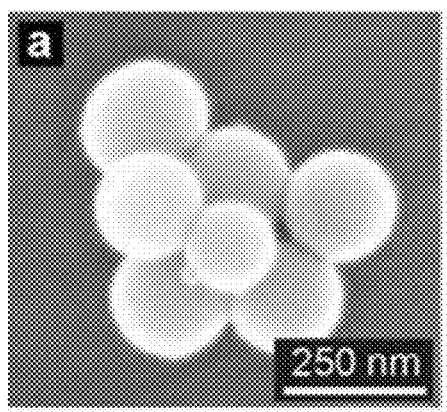
FIGS. 15A-15E show SEM images and data plots of exemplary nanoscale olive structures synthesized using 60 mM TEOS concentration using various sized templates.
Figure 15B:
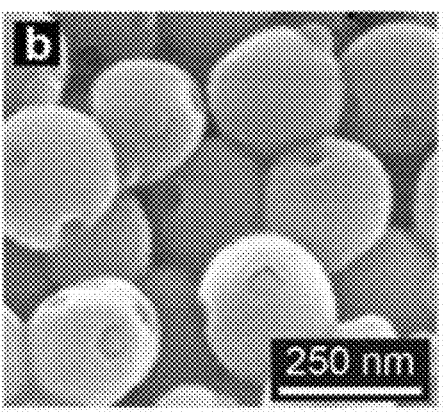
Figure 15C:
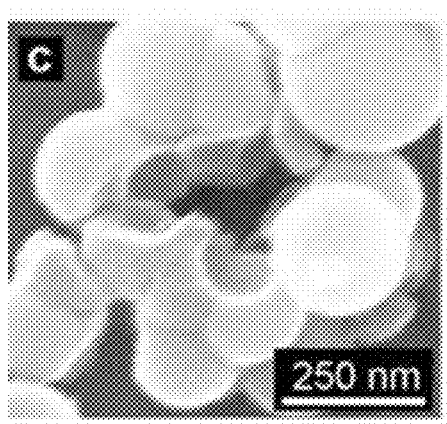
Figure 15D:
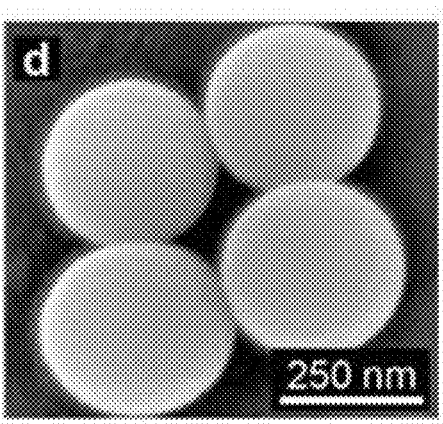
Figure 15E:
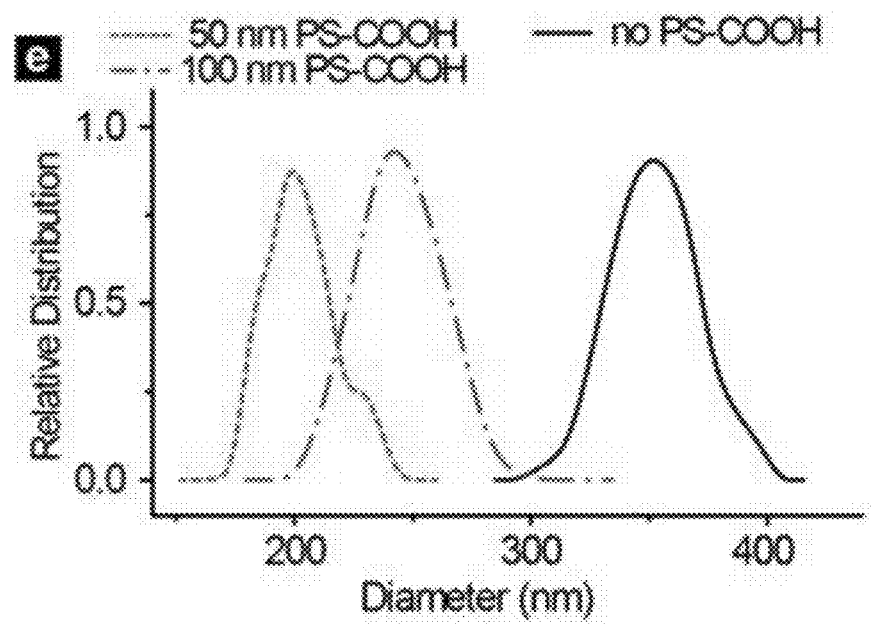

For example, three different sizes of PS-COOH were used to investigate the effect of template size on eccentric particle formation. Using 60 mM TEOS with the standard reaction conditions, particles were synthesized with no PS present, 50 nm, 100 nm and 200 nm diameter PS-COOH templates. FIGS. 15A-15E show SEM images and data plots of exemplary nanoscale olive structures synthesized using 60 mM TEOS concentration using various sized templates, i.e., PS-COOH templates of different diameters: (a) 50 nm, as shown in FIG. 15A; (b) 100 nm, as shown in FIG. 15B; (c) 200 nm in diameter, as shown in FIG. 15C; and (d) no template, as shown in FIG. 15D. FIG. 15E shows a data plot depicting the olives made with 50 nm and 100 nm templates, which shows a smaller average diameter when compared to a silica sample made with no templates. For example, no size distribution is reported for olive synthesis using 200 nm templates because the silica wrapped poorly around many of the 200 nm templates (e.g., they instead agglomerated leaving imprints where the polystyrene spheres once were). As illustrated by the SEM images in FIGS. 15A and 15B, the 50 nm and 100 nm PS-COOH templates successfully made eccentric nanoparticles. These olives were smaller on average than a pure silica particle. However, 200 nm PS-COOH included in the 60 mM TEOS mix appeared to have formed poorly or not at all. For example, from the SEM images, the silica tried to wrap around the PS-COOH unsuccessfully, leaving round indents and heavily agglomerated particles.

Comparing the diameter of the pure silica particle (e.g., 350 nm) with the size of the 200 nm PS-COOH, the exemplary results suggested that there is an upper limit to the size of PS-COOH the silica can engulf. It may suggest that the interaction between the silica and the PS-COOH during formation are due to multiple weak bonds. Successful formation of an eccentric particle would thus hinge on growing enough silica to physically entrap the PS-COOH.

Figures 16A, 16B, 16C:
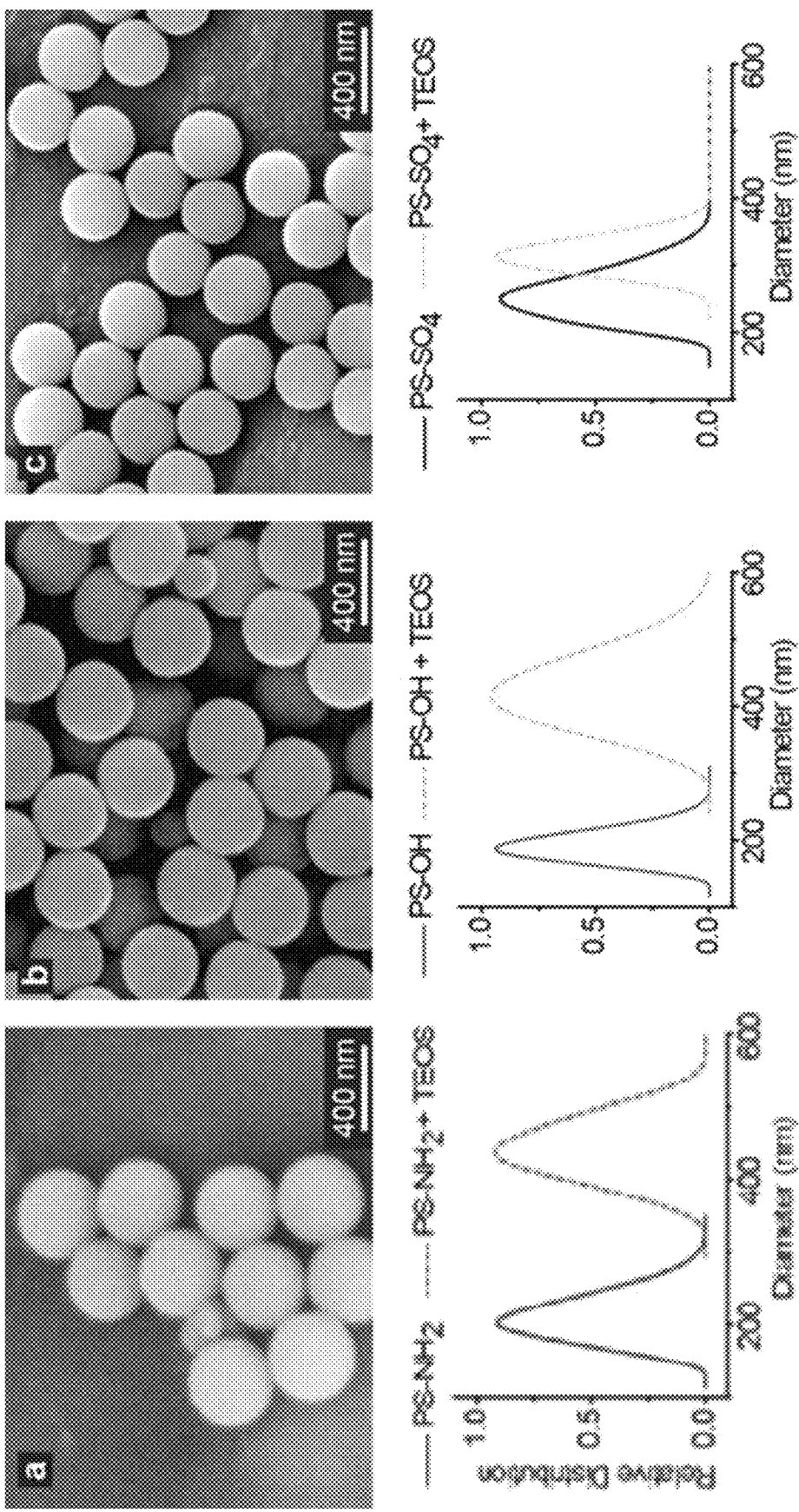
FIGS. 16A-16C show SEM images and accompanying data plots for analysis of exemplary polystyrene nanospheres functionalized with amines, hydroxyls, and sulfates.

In the exemplary results of the exemplary implementations, for example, the surface functionality of the template particle appeared to play a central role in olive morphology. The addition of 200 nm PS-$NH_2$, PS-OH, or PS-$SO_4$ into a 60 mM TEOS reaction solution yielded particles that were completely encapsulated by silica. FIGS. 16A-16C show SEM images and accompanying data plots featuring exemplary 200 nm polystyrene spheres functionalized with amines (FIG. 16A), hydroxyls (FIG. 16B), and sulfates (FIG. 16C), e.g., which were added to a 60 mM TEOS solution. For example, these polystyrene spheres were uniformly coated with silica as confirmed by the SEM and DLS analysis data plots. For example, this was observed by an increase in the diameter of the resultant particles over the size of the polystyrene templates and by SEM images showing spherical particles with smooth morphology. Therefore, some undetermined interaction between TEOS and PS-COOH enabled the formation of the exemplary olive nanostructures which did not occur with polystyrene templates containing other surface functional groups.

The exemplary results of the exemplary implementations, for example, may suggest that the interaction between the silica and the PS-COOH interact during formation with multiple weak molecular bonds. For example, comparing the diameter of the pure silica particle (350 nm) with the size of the 200 nm PS-COOH, suggests that core size in addition to surface functionality plays an important role in Janus template formation. Successful formation of a Janus template would thus hinge on growing enough silica to physically entrap the core.

Silica can be grown around polystyrene of different surface functionalities using Stöber's method. In some implementations, uniform shells were grown around amine-terminated polystyrene while silica islands were grown around sulfate terminated polystyrene. Differences between those implementations and the exemplary implementations described here is likely due to the relative amounts of water and ammonium hydroxide used. Those previous implementations used 3.5 mL DI water and 0.5 mL ammonium hydroxide; 6 times more volume of water than ammonium hydroxide. In the exemplary implementations of the disclosed method, the volume of water used was about half the volume of ammonium hydroxide used. The diameter of silica nanoparticles (e.g., such as those formed with the Stöber method) is highly sensitive to even small changes in reaction conditions and the same is likely true for shell formation.

For example, because the exemplary nanoscale olive structures contain both silica and carboxyl groups on the same particle, chemical moieties like a targeting agent and a therapeutic can be attached independently in a spatially defined manner. The olives may be of use as a multifunctional delivery platform because it can spatially organize the different chemical moieties on the nanoscale, which is a feature not commonly found in existing drug delivery systems like nanoliposomes or silica. Alternatively, for example, by removing polystyrene, the olive becomes a nanobowl with internal carrier space for therapeutic or diagnostic agents. The disclosed nanobowls can then be capped with biocompatible materials, including PLGA, liposomes, and chitosan.

For conditional and controlled release of the therapeutic from the nanobowl structure, e.g., such a cap (e.g., capping particle), the payload could be released by specific interaction with DNA, enzymatic processes, or environmental triggers like temperature and pH. Existing delivery systems usually have pores or open surfaces that allow passive and/or continuous release of their loads (imaging contrast molecules or therapeutic agents). The disclosed nanobowl structures can be used for a controlled release of imaging contrast molecules and therapeutic (theranostics) agents.

Exemplary Embodiments of the Disclosed Nano/Micro Ball Structures

In some aspects of the present technology, techniques, systems, and devices are disclosed for fabricating and implementing a nano/microscale carrier structures having a hollow and porous shell functionalized interior and/or exterior surfaces and capable of magnetic guidance that enable controlled release of a payload, improvement of cellular uptake, and other features. In some implementations, the nano/microscale carrier structures of the disclosed technology can be utilized for targeted and on-demand delivery of molecules and small molecules for the diagnosis and/or treatment (e.g., referred to as theranostics) of abnormal pathology and diseases in both human and animals.

Hollow, porous micro- and nano-particles having a diameter in a range of 100 nm to 100 µm are of particular interest in catalysis, photonics, biosensing, nanodelivery of therapeutic and diagnostic agents, cell culture, and toxin scavenging. Such particle structures are useful for encapsulation and storage. In some cases, nanoparticles are surface modified with other elements, such as gold or self-assembled organic molecules that allow task-oriented functionalization. This additional functionality can include responsiveness to light, temperature, pH, and other environmental cues. For example, gold in general has many highly attractive photophysical properties that make it useful for imaging as well as thermal manipulations. Gold can be used to design different structures, including solid spheres and rods, hollow structures such as nanocages, and core/shell structures.

In some embodiments, for example, the disclosed technology can include fabrication methods to produce the nano/micro carrier structures by fabricating a template particle including a core particle covered by mask particles used to fabricate a porous and/or hollow/porous shell structure formed of selected materials that can be functionalized for desired applications. In some embodiments, for example, the shell structures can be fabricated as gold nanoscale or microscale golf balls, having a solid silica core with an outer gold shell surface having pits or pores leading to the core. In some embodiments, for example, the shell structures can be fabricated as hollow and porous gold nanoscale or microscale wiffle balls having a gold shell surface with pores leading to the a hollow interior. These embodiments can be further modified to allow for layers or islands of gold within a silica shell which in turn facilitate attachment of other entities (e.g., iron oxide particles, molecules, passivation agents) to the interior of the carrier structure.

In some embodiments, for example, fabrication methods to produce the disclosed nano/microscale carrier structures can include one or more of the following processes. An exemplary fabrication method can include (i) synthesis of a pollen-like template particle with a large center particle and smaller satellite particles attached to it, e.g., which can be made from silica, polystyrene or a combination of the two; in which the synthesis can include (i.a.) addition of small gold nanoparticles (e.g., ~5 nm) to the outside of the pollen-like template, (i.b.) growth of larger gold islands or a gold shell using the gold nanoparticles, and/or (i.c) creation of a porous, golf ball-like shell or a hollow and porous wiffle ball-like shell by dissolution of the template in a stepwise dissolution of the silica. The exemplary fabrication method can include (ii) modifications to the template that can include growth of an exemplary silica layer around the gold island or gold shell, and/or addition of iron oxide nanoparticles to the exterior and/or interior surface of the exemplary silica golf/wiffle ball-like shell. The exemplary fabrication method can include (iii) differential functionalization of interior and exterior surfaces of the structure (e.g., the ball/particle), modification of the exemplary silica surface by an alkoxysilane, and removal of the core. The exemplary fabrication method can include (iv) loading of a molecular payload (e.g., such as a drug, image contrast agent, etc.) into shells. For example, a molecular payload that can be loaded into the shell can include a drug, image contrast agent, enzyme, protein, hormone, glycoprotein, glycolipid, nucleic acid, aptamer, lipid, and/or metallic, polymeric, or ceramic nanoparticle. The exemplary fabrication method can include (v) controlled release of the molecular payload from the exemplary wiffle ball. The exemplary fabrication method can include (vi) external surface modification of the surface with a passivation layer, e.g., including polyethylene glycol or similar inert polymer, and addition of targeting moieties to improve cellular uptake. The exemplary fabrication method can include (vii) guidance of the exemplary magnetically-loaded golf/wiffle ball carrier structure to a specific location under external magnetic field.

The disclosed nano/micro carrier structures can be configured as a particle that allows of dual functionalization in the internal surface, e.g., because of the presence gold and silica. Magnetic guidance of the disclosed nano/micro carrier structures is possible with inclusion of magnetic material. The disclosed fabrication methods can produce multiple types of particles using the same template based synthesis process, e.g., such as the two exemplary porous, golf ball-like carrier structures and hollow/porous wiffle ball-like carrier structures. The disclosed fabrication methods can produce these multiple particle types in a variety of sizes, e.g., to have 200 nm or 1 µm diameter.

FIGS. 17-21 show illustrative diagrams of fabrication techniques to produce and implementations of the disclosed nano/micro carrier structures.

Exemplary Synthesis of a Shell Structure

Figure 17:
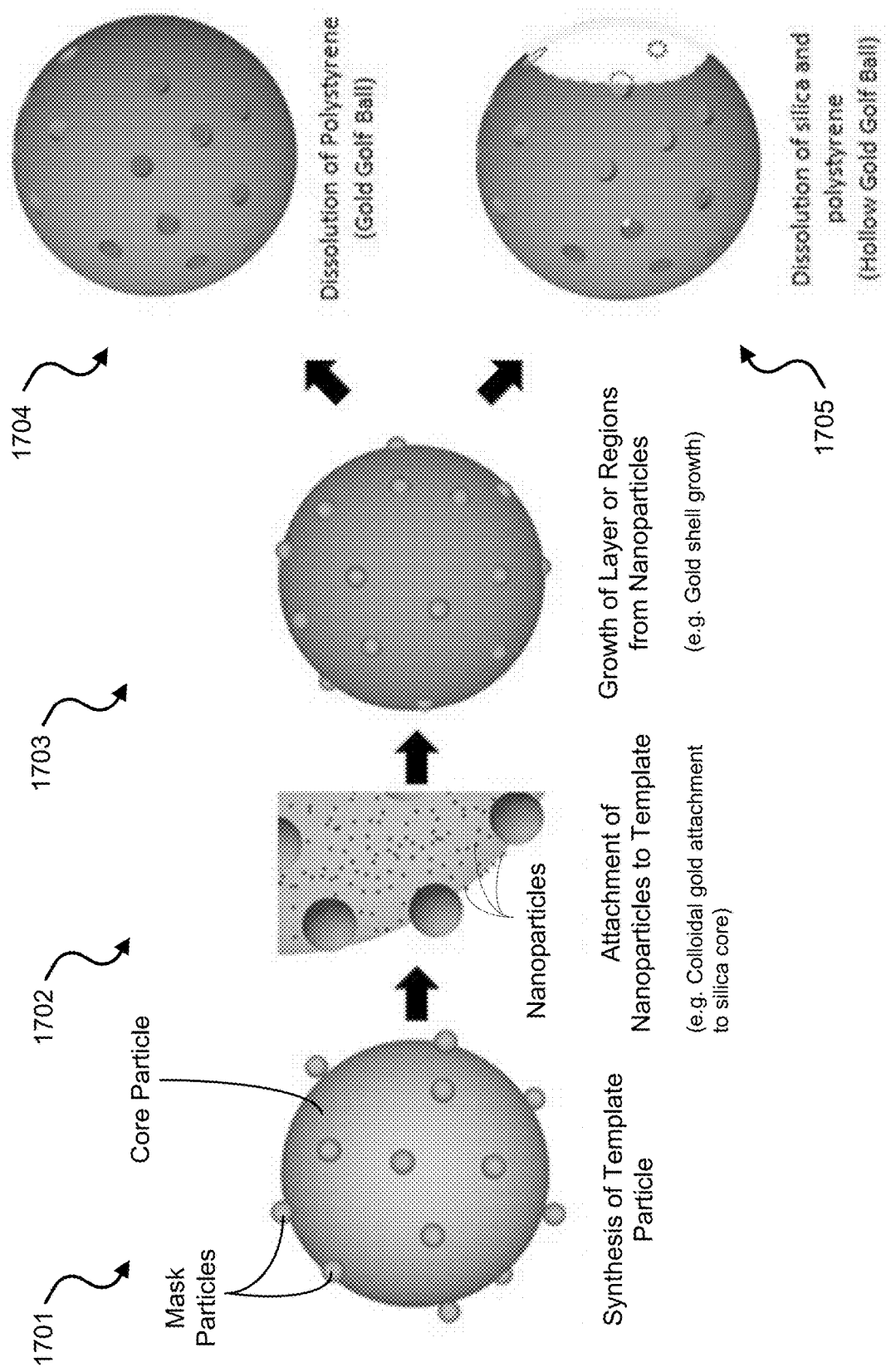
FIG. 17 shows an illustrative schematic of an exemplary fabrication process to synthesize a porous and hollow/porous carrier structure depicting different reactions to form the structures.

FIG. 17 shows an illustrative schematic of an exemplary fabrication method to produce a porous and hollow/porous carrier structure depicting different reactions to form the structures, e.g., a porous golf ball-like carrier structure (nano golf ball) and a hollow and porous wiffle ball-like carrier structure (nano wiffle ball). The fabrication method includes a process 1701 to synthesize a template particle includes attaching mask particles to a core particle, e.g., which can be attached by electrostatic interaction. In some implementations of the process 1701, for example, negatively-charged satellite colloidal polystyrene spheres (e.g., ~100 nm) can be used as the mask particles and attached to a larger cationic silica core particle (e.g., ~1 µm). The fabrication method includes a process 1702 to attach nanoparticles to the uncovered portion of the core particle. In some implementations of the process 1702, for example, colloidal gold is attached to the exemplary silica core particle, in which the exemplary polystyrene mask particles prevent such attachment of the gold over the regions where the mask particles are attached to the core particle. For example, the gold layer can be formed by addition of small gold nanoparticles (e.g., ~5 nm) to the outside of the pollen-like template. The fabrication method includes a process 1703 to form a layer by material growth of the attached nanoparticles over the uncovered portion of the core particle, thereby forming a shell structure over the template. In some implementations of the process 1703, for example, growth of larger gold islands or regions on the template using the gold nanoparticles to produce a gold shell. For example, the template can be immersed in a solution of gold hydroxide and processed to causes the gold seeds to nucleate into a gold shell around the template. The fabrication method includes a process 1704 to remove the mask particles from the template to form a porous carrier structure. In some implementations of the process 1704, for example, a porous golf ball structure having an outer gold porous shell formed over a silica core particle can be formed by dissolution of the exemplary polystyrene mask particles. Additionally or alternatively, the fabrication method includes a process 1705 to remove the template by removing the mask particles and the core particle (or at least a portion of the core particle) to form a hollow, porous carrier structure. In some implementations of the process 1705, for example, a hollow and porous wiffle ball structure of a gold porous shell can be formed by dissolution of the exemplary polystyrene mask particles and the exemplary silica core in a step-wise dissolution process, e.g., first dissolving the mask particles and then dissolving the core particle.

Exemplary Modifications to the Template and/or Shell

Figure 18B:
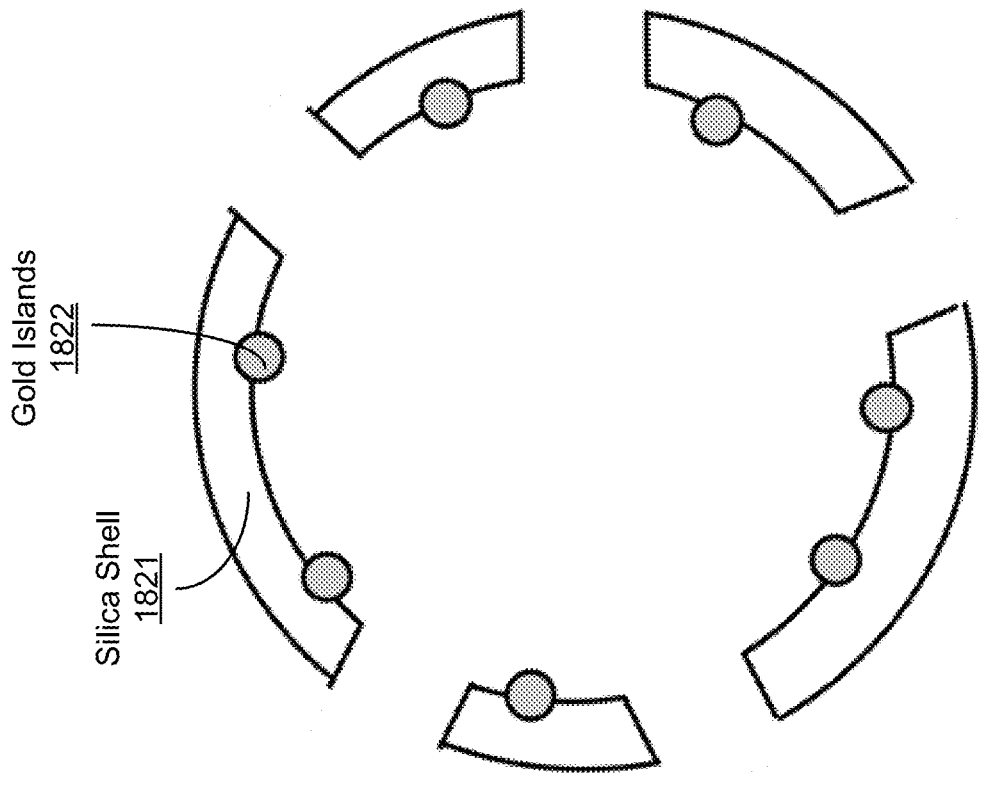
FIG. 18B shows an illustrative diagram of an exemplary carrier structure including a silica shell over gold islands embedded in the interior of the silica shell.
Figure 18A:
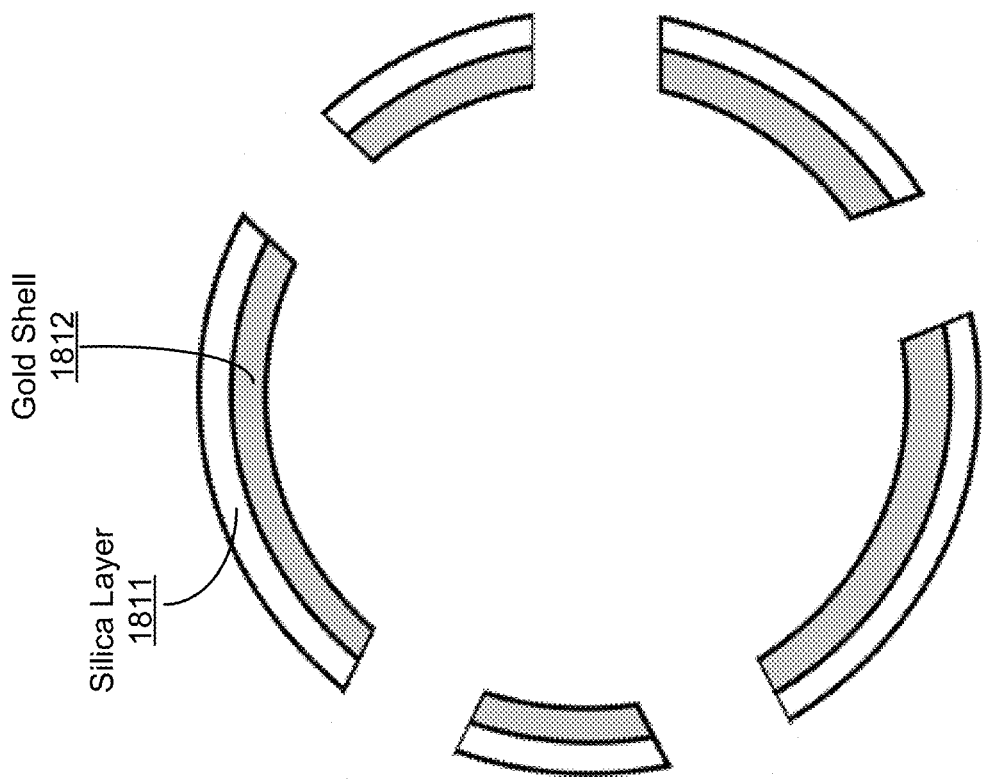
FIG. 18A shows an illustrative diagram of an exemplary carrier structure including a silica shell over a gold shell.
Figure 19:
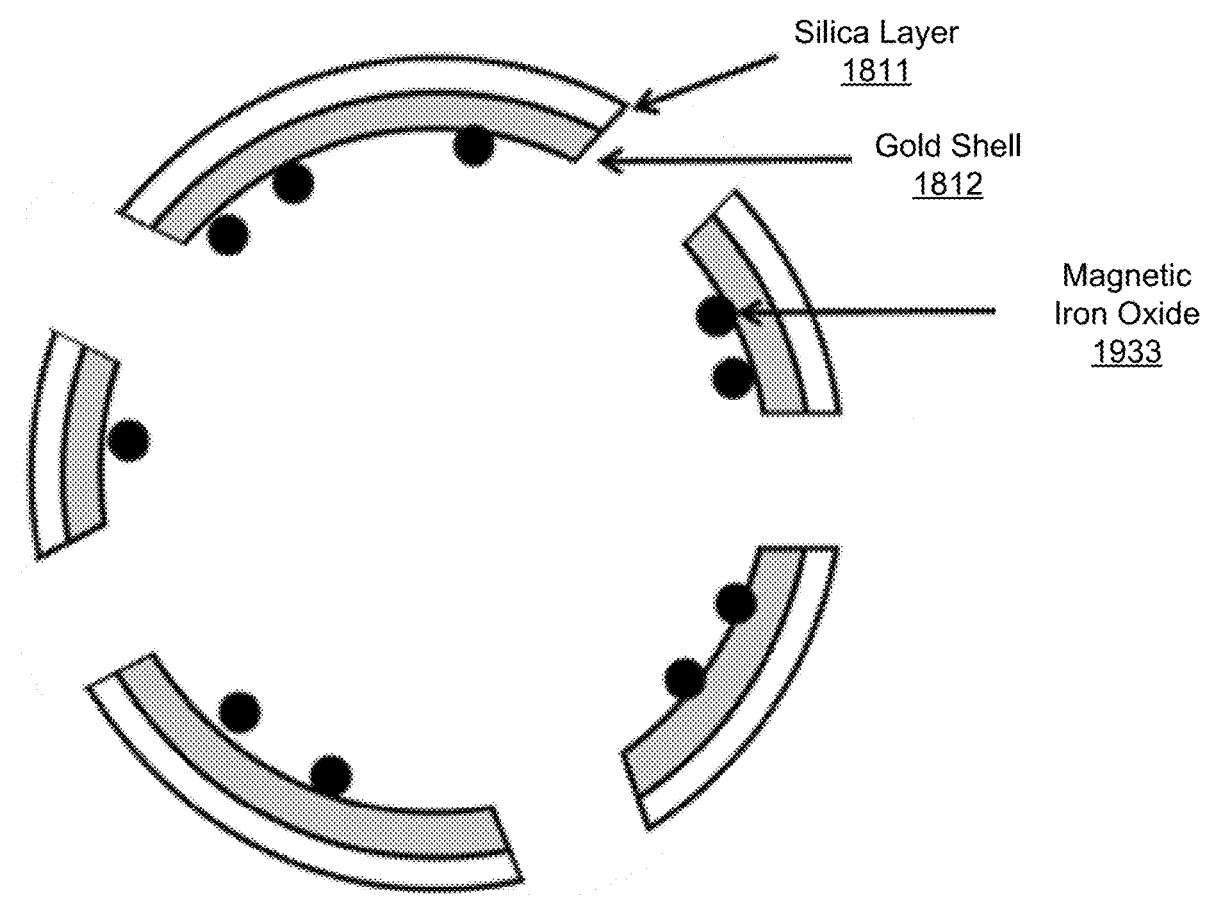
FIG. 19 shows an illustrative diagram of an exemplary carrier structure including iron oxide nanoparticles added into the interior of the exemplary gold/silica shell of FIG. 18A.

The fabrication method can also include surface modification processes to the template that enables differential functionalization to the shell. In some implementations, for example, the fabrication method can include a process to grow a silica layer around the gold shells. FIG. 18A shows an illustrative diagram of an exemplary carrier structure including a silica shell 1811 over a gold shell 1812. In some implementations, for example, the fabrication method can include a process to form gold islands. FIG. 18B shows an illustrative diagram of an exemplary carrier structure including a silica shell 1821 over gold islands 1822 embedded in the interior of the silica shell 1821. In some implementations, for example, iron oxide nanoparticles can be attached into the exterior and/or the interior of the shell. FIG. 19 shows an illustrative diagram of an exemplary carrier structure including iron oxide nanoparticles 1933 added into the interior of the exemplary silica/gold shell of FIG. 18A. In some implementations, for example, the iron oxide nanoparticles 1933 can be placed on the outside of the shell as well.

Figure 20:
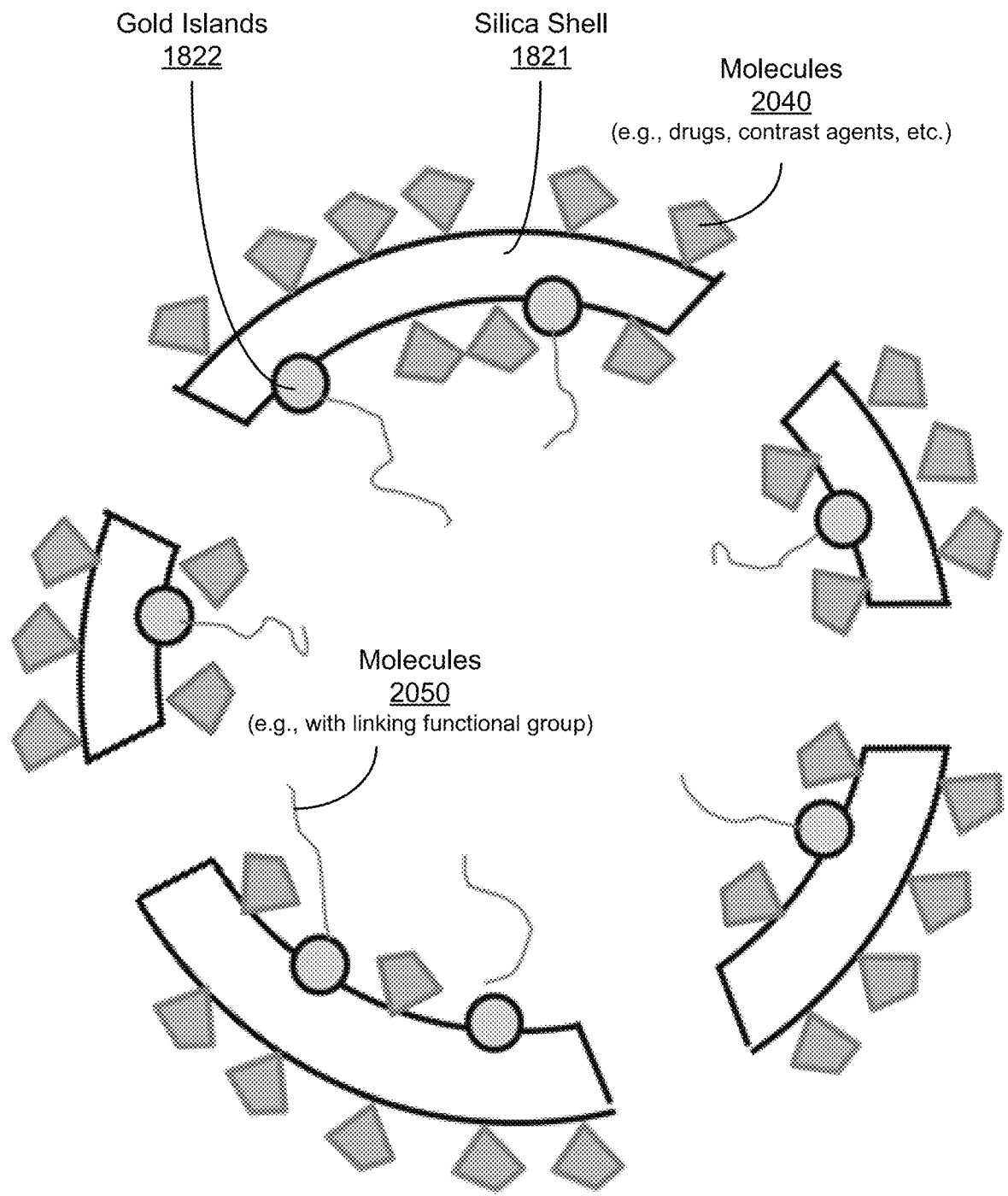
FIG. 20 shows an illustrative diagram of an exemplary carrier structure including selective functionalization of the exemplary silica shell/gold islands of FIG. 18B with molecules inside and targeting molecules outside.

The fabrication method can also include surface modification processes to the formed shell structures that enable functionalization of the shell externally and/or internally with different molecules. FIG. 20 shows an illustrative diagram of an exemplary carrier structure including selective functionalization of the exemplary silica shell 1821/gold islands 1822 with molecules and/or small molecules 2040 (e.g., including payloads such as drugs) inside and targeting molecules 2050 outside. The fabrication method can include a process using silica surface, alkoxysilane chemistry to interface a wide variety of molecules. The fabrication method can include a process to attach molecules on the gold surface, e.g., using a free sulfhydrl or amine that will attach to the surface of the gold spontaneously. For example, this can be used for attachment of passivation agents like polyethylene glycol or targeting moieties.

Exemplary Loading of the Carrier with a Payload

For differential functionalization, for example, the interior can be modified using a drug or contrast agent. One such example for linkage is the modification of the drug (monomethylauristatin E, MMAE) with an alkoxysilane to attach to the shell structure or linking molecule attached to the shell structure based on the material.

Exemplary Releasing of the Payload from the Carrier

In some implementations, a chemical linker interfaces the active molecule to the silica. Chemical linkers that can be used can be selected from those that are sensitive to enzymes inside or outside the cell, e.g., to cause controlled delivery of the payload from the carrier at the target. Other exemplary chemical linkers can be selected from those that are sensitive to light, pH, and temperature, or other stimuli to control the delivery of the payload.

The carrier structures can be targeted to specific cells. For example, in implementations using the wiffle ball structures (e.g., hollow and porous carrier structures), the carriers can be targeted to specific cells by attachment of a targeting molecule on the outside of the shell. This can be accomplished by using any targeting molecule with a free sulfhydryl or amine group, for example, for outer gold shells. The sulfhydryl and amine groups will spontaneously form a strong bond with the gold surface. The external surface can also be modified with passivation ligands like polyethylene glycol to improve circulation time in the bloodstream.

Exemplary Magnetic Guidance of the Carrier

In some implementations using the fabricated nano/micro carrier structures, e.g., such as the nano golf balls and nano wiffle balls, a strong external magnet can be placed over the bodily region of interest and carriers can be injected intravenously into the body (e.g., in a biocompatible solution) to preferentially collect in the local tissue near the magnet. For example, this is particularly useful in difficult to access regions such as the brain or deep cancer tumors. As shown previously in FIG. 5, the exemplary nano/micro carrier structures (e.g., such as nano golf balls or nano wiffle balls) can be injected into the bloodstream of a subject (e.g., human or animal subject), and a strong magnet can be used to guide and direct (e.g., preferentially pull) the exemplary magnetically responsive carriers (e.g., nanoballs) out of the bloodstream and into the tissue of interest.

Exemplary Implementations of the Fabrication Methods for Nanoball Carrier Synthesis and Functionalization In some implementations, the disclosed fabrication methods can include the following exemplary synthesis techniques to produce magnetically-sensitive gold/silica nanoball structures using solution-based processes, as shown in FIGS. 17-20. Exemplary implementations of an exemplary fabrication method were performed, where exemplary results are shown in FIG. 21.

Surface Functionalization of Exemplary Silica Particles with PDDA

Colloidal silica has a net negative surface charge at a pH values above ~2.2. The net charge on the surface of colloidal silica can be reversed using a cationic polyelectrolyte such as poly(diallyldimethylammonium chloride) (PDDA). PDDA electrostatically binds to the surface and reverses the net charge on the surface of colloidal silica. The stoichiometric formation of salt linkages between the quaternary ammonium ions in the polymer and the deprotonated silanol groups of the colloid. This was performed by adding 320 µL of ammonium hydroxide to 5 mL of 2% dispersions of colloidal silica (pH≳11). Subsequently, the solution was placed in an ultrasonic ice bath at 4° C., and then 5 mL of 1 wt % aqueous PDDA solution was added into the mixture. The resulting solution was left in the ultrasonic bath for 20 min. The tube containing the solution was then centrifuged at 3200 g for 10 min to remove unadsorbed polymer. Centrifugation and re-dispersion was repeated four times with a change to a clean container in between. The white pellet was re-dispersed in 5 mL of water.

Synthesis of the Exemplary Template

Negatively-charged satellite colloidal polystyrene spheres were attached to the larger cationic silica cores. Carboxyl-functionalized polystyrene spheres ~100 nm in diameter were electrostatically attracted to the 1000 nm PDDA-functionalized silica. In a 2 mL centrifuge tube, 1 mL of the PDDA-functionalized silica was centrifuged at 3200 g and re-dispersed in 1 mL of EtOH. The tube containing PDDA-functionalized silica solution was placed in an ultrasonic ice bath at 4° C. for 10 min. Then 25 µL of aqueous carboxyl-functionalized colloidal polystyrene was added to the PDDA-functionalized silica and left in the ultrasonic ice bath for an additional 5 min. The mixture was then centrifuged at 1000 g for 5 min, decanted and the pellet was re-dispersed in 1 mL of water.

Attachment of Gold Seeds to the Template

Colloidal gold nanoparticles with 1-3 nm diameters were used as gold seeds for the gold plating process. 54 mL of water and 50 µL of 10 M sodium hydroxide were mixed together. In a separate container 12 µL of 80% Tetrakis (hydroxymethyl)phosphonium chloride (THPC) was diluted in 1 mL of water, added to the original solution, and stirred for 5 min. 15 mL of 1% chloroauric acid was added to the solution and stirring continued for another 30 min. The gold seed solution was aged 24 hours at 4° C. before use. THPC simultaneously reduces chloroauric acid and stabilizes gold nanoparticles in aqueous solution, leaving the gold nanoparticles with a negative charge. Assuming the bulk density of gold and complete conversion to 3 nm gold seeds, the gold seed concentration was $1.0 \times 10^{16}$ gold seeds/mL.

The exemplary gold seeds were attached to the templates by adding 100 µL of the template solution and 5 mL of gold seed solution together while vigorously stirring. The solution was stirred at 45° C. for at least 30 min. To remove excess free gold seeds from the mixture, the solution was centrifuged at 1000 g for 10 min. This centrifugation step was repeated at least 2 times. Finally, a reddish white pellet formed and was redispersed in 1 mL of water.

Growth of the Exemplary Gold Shell

A gold shell was grown on the exemplary gold-seeded colloidal silica templates with the attached polystyrene satellites using a solution of gold hydroxide. In a 100 mL bottle gold hydroxide solution was prepared by stirring 70 mL of 5.37 mM $K_2CO_3$ for 10 min prior to the addition of 3.15 mL of 1% chloroauric acid to the solution. The gold hydroxide solution was initially light yellow and became clear after 1 hour of stirring prior to refrigeration. The solution was aged in the dark at 4° C. for 24 hours prior to use in plating. Then 500 µL of the gold-seeded templates were added to 15 mL of gold hydroxide and mixed vigorously for 5 min followed by the addition of 50 µL of 37% formaldehyde. The addition of formaldehyde starts the plating process by reduction of the gold hydroxide into metallic gold. This step was quickly followed by the addition of 5 µL of $NH_4OH$. This causes the gold seeds to nucleate into a shell around the template. The resulting solution was mixed using a tumbler for approximately 3 hours. The mixture was then centrifuged at 1000 g for 5 min to remove solution. This step was repeated at least 4 times. The pellet was re-dispersed in 2 mL of water.

Dissolution of the Exemplary Template

The exemplary gold golf balls were created when the 100 nm polystyrene satellites were removed. Gold plated templates were re-dispersed in 5 mL of dimethylformamide (DMF) after centrifugation. The tube containing the solution was placed in an ultrasonic water bath for 20 min at 60° C. followed by centrifugation at 3200 g for 10 min and re-dispersing in DMF. Centrifugation and rinsing with DMF was repeated twice more before re-dispersing in water.

Hollow gold golf balls were made by removing the silica core by dispersing the gold golf balls in 10% hydrofluoric acid (HF) while in 2 mL centrifuge tubes. The resulting mixture was left standing for 24 hours. This step was repeated once more. The hollow gold golf balls were rinsed 6 times by centrifugation with water and then re-dispersed in 2 mL of water.

Figure 21A:
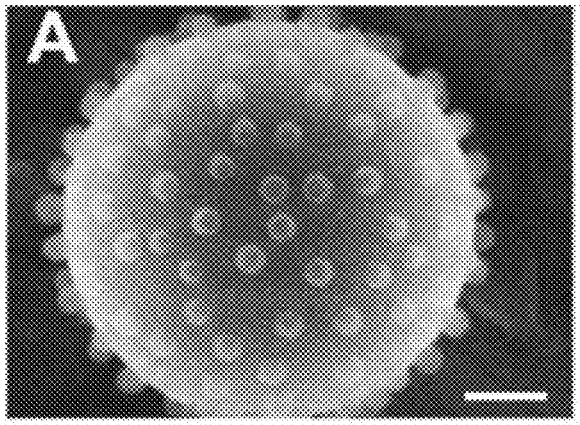
FIGS. 21A-21F show SEM images of exemplary porous and hollow/porous nanocarrier structures.
Figure 21B:
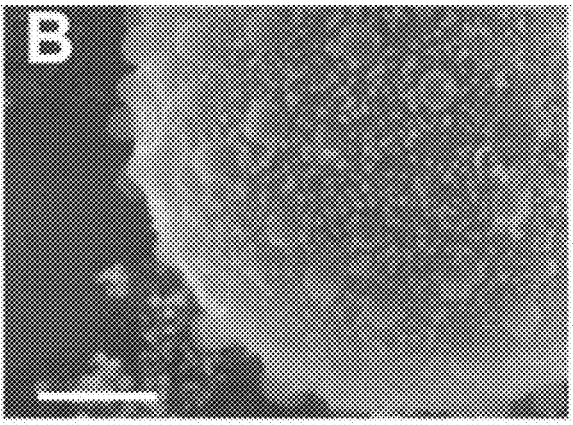
Figure 21C:
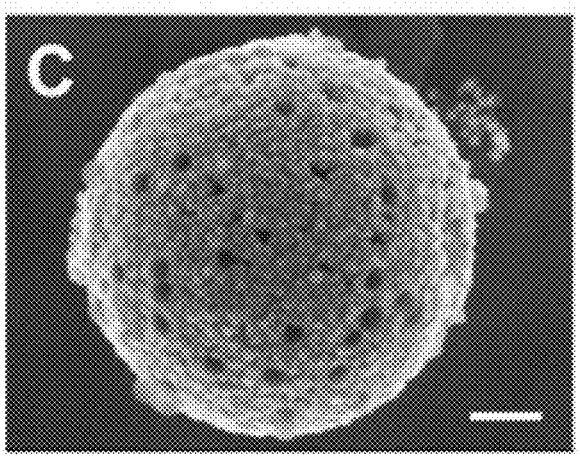
Figure 21D:
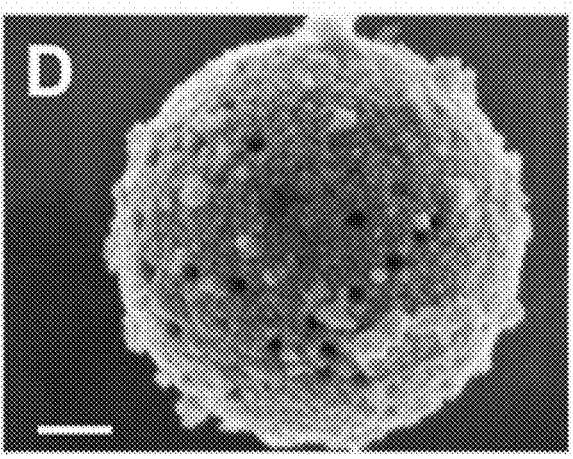
Figure 21E:
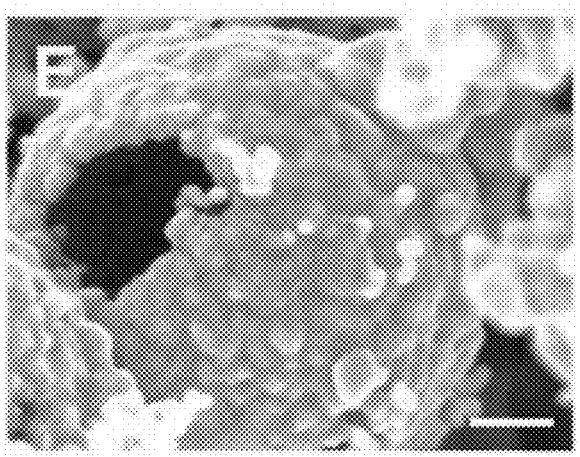
Figure 21F:
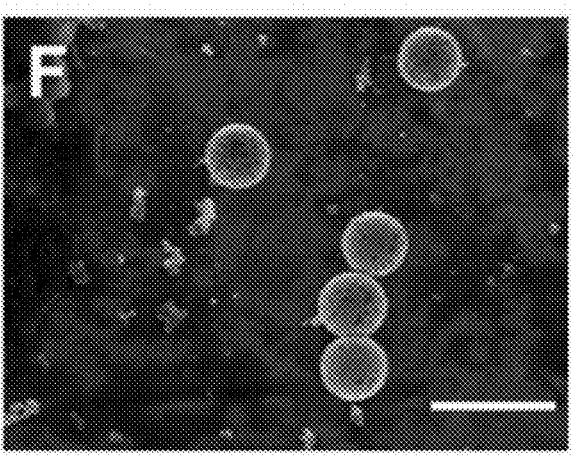

FIGS. 21A-21F show scanning electron micrograph (SEM) images of exemplary porous and hollow/porous nanocarrier structures (e.g., gold golf balls) using the exemplary synthesis techniques described above. Image (A) of FIG. 21A shows an exemplary 1000 nm polystyrene/$SiO_2$ template. Image (B) of FIG. 21B shows an exemplary gold seeding of template. Image (C) of FIG. 21C shows gold shell growth. Image (D) of FIG. 21D shows dissolution of smaller polystyrene (e.g., which forms gold golf balls). Image (E) of FIG. 21E shows dissolution of $SiO_2$ core particle (e.g., which forms hollow gold wiffle balls). Image (F) of FIG. 21F shows a wide angle view of an exemplary 1000 nm gold shell template. The scale bar shown in the images of FIGS. 21A-21E represents 200 nm. The scale bar shown in the image of FIG. 21F represents 2 µm.

Exemplary Embodiments of Dual-Functionalized Hollow Porous Nanoparticles

Figure 22A:
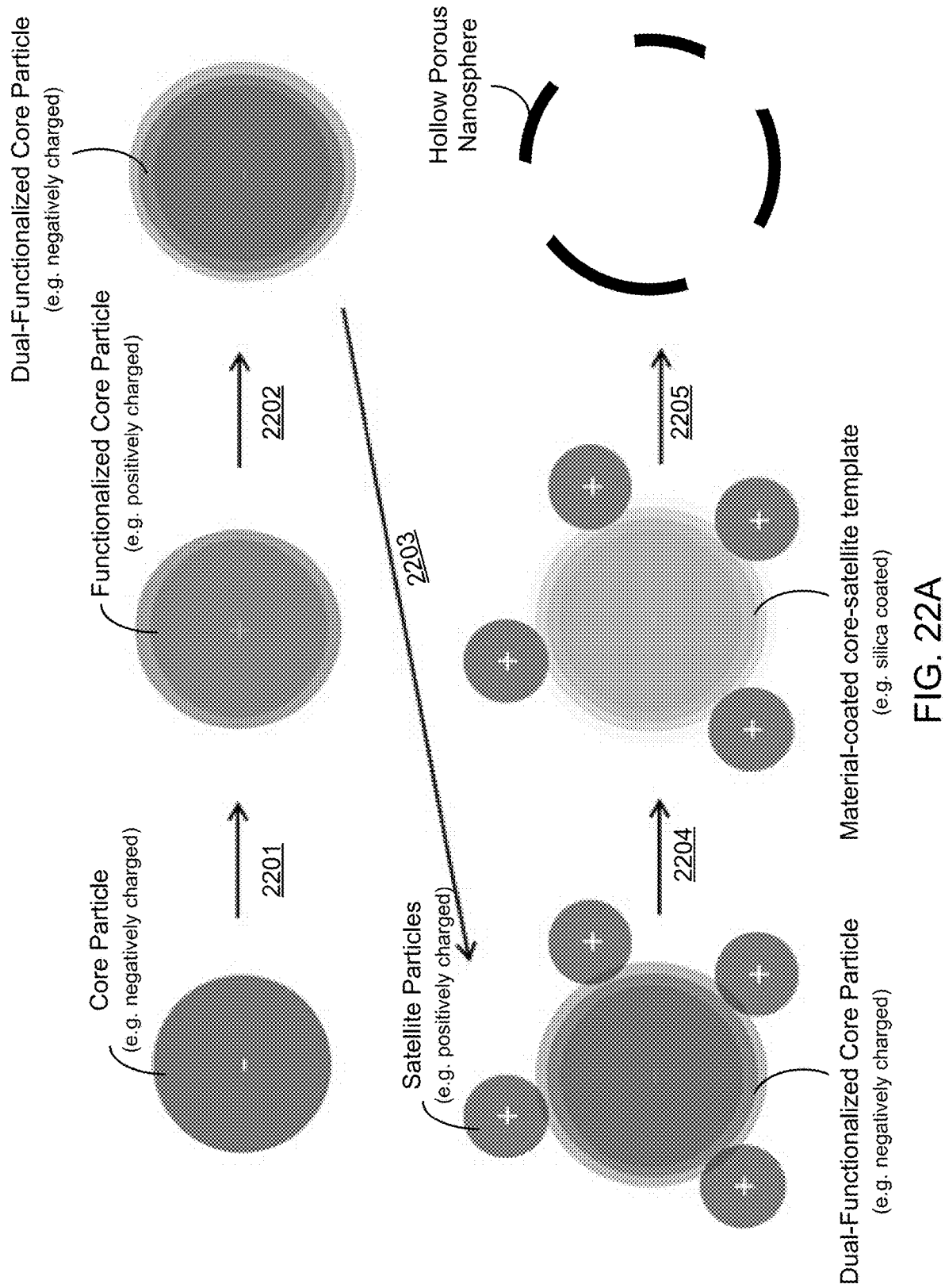
FIGS. 22A and 22B show illustrative diagrams of an exemplary synthesis method that can be used to fabricate porous hollow nano-/mirco-particles of the disclosed technology on dual-functionalized template structures.
Figure 22B:
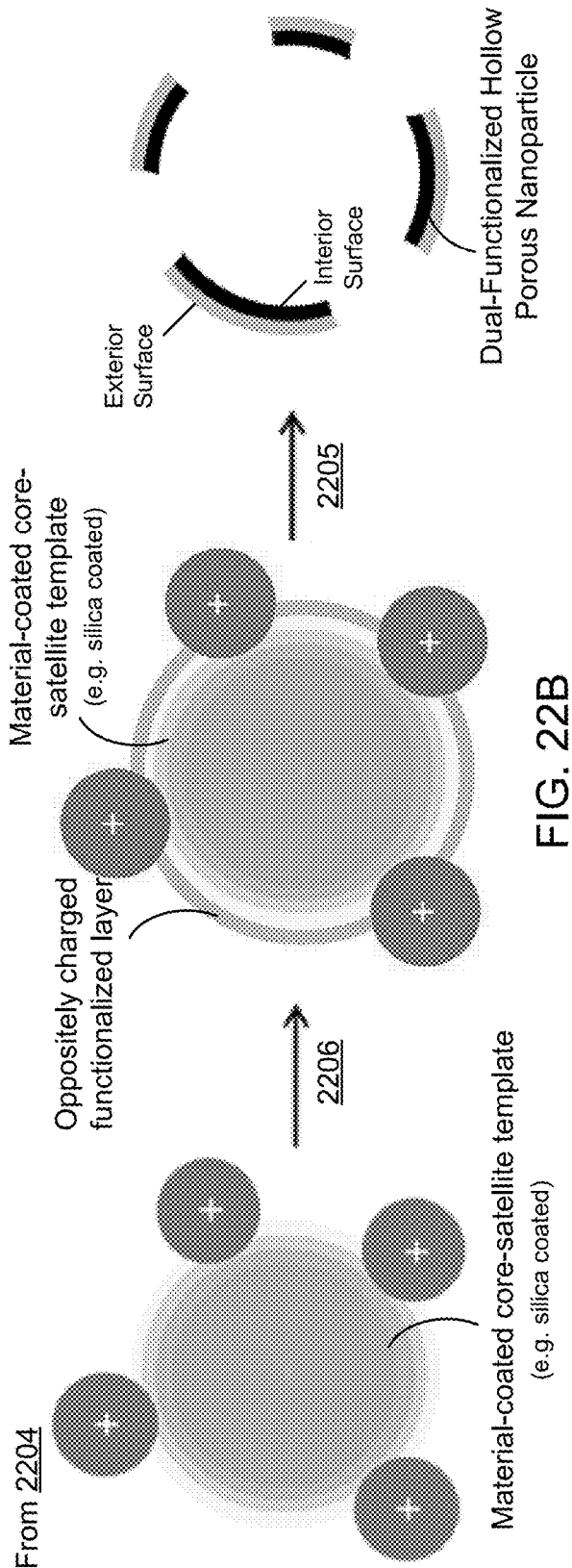

In some exemplary embodiments of the disclosed technology, the hollow porous nanoparticles (e.g., hollow porous silica nanospheres), including dual-functionalized hollow porous nanoparticles, can be synthesized in an exemplary step-wise electrostatic assembly process. FIGS. 22A and 22B show illustrative diagrams of an exemplary synthesis method that can be used to fabricate porous hollow nano-/micro-particles (e.g., silica nanospheres) of the disclosed technology on dual-functionalized template structures, in which the produced porous hollow nanoparticles can be fabricated to possess one chemical functional group on the particle's interior and another chemical functional group on the particle's exterior. As shown in FIG. 22A, the method includes a process 2201 to functionalize a negatively charged core particle, e.g., to form a coating, providing a positively charged surface to the core particle. For example, in some implementations of the process 2201, a 1 µm modified carboxylated polystyrene particle is coated by a first coating (e.g., PDDA) to form a positively charged core particle. The method includes a process 2202 to further modify the functionalized particle, forming a second coating, to provide a negatively charged functionalized surface over the positively charged first functionalization layer that is over the negatively charged core, e.g., thereby producing a dual-functionalized core particle. For example, in some implementations of the process 2202, a second coating (e.g., poly(acrylic acid) (PAA)) can be formed over the core particle to form a negatively charged surface of the dual-functionalized core particle. The method includes a process 2203 to attach positively charged satellite particles to the multi-coated negatively charged core particle. For example, in some implementations of the process 2203, the dual-functionalized polymer coated core (e.g., PAA-PDDA-PS) can be attached to 100 nm amine-modified polystyrene particles. The method includes a process 2204 to form a shell (e.g., silica shell) over the core-satellite template. For example, in some implementations of the process 2204, a positively charged silane (e.g., QuATPmS) can be grown on the negatively charged PAA-PDDA-PS core while avoiding the growth on the positive satellites to produce the silica shell over the core particle. In some implementations of the method, as shown in FIG. 22A for example, the method includes a process 2205 to remove the core-satellite template and produce a hollow porous nanoparticle (e.g., a hollow porous silica nanosphere). For example, in some implementations of the process 2205, the core and satellite particles can be etched with organic solvent. Whereas, in some implementations of the method, as shown in FIG. 22B, for example, the method can include a process 2206 prior to the process 2205 to form an external functionalized surface (e.g., a coating) over the shell, where the coating includes an opposite charge to that of the shell. For example, in some implementations of the process 2206, tetraethylorthosilicate (TEOS) can be used to form a final thin layer over the silica shell on the dual-functionalized core template.

In some embodiments of the method depicted in FIGS. 22A and 22B, for example, the method can be implemented with an initial positively charged core particle in the process 2201 to form the functionalized core particle having a negatively charged surface. The process 2202 can including forming a positively charged second coating on the core particle to form the dual-functionalized core particle, such that the process 2203 includes attaching negatively charged satellite particles to the positively charged exterior surface of the dual-functionalized core particle. The process 2204 can include forming the shell using a negatively charged coating material (e.g., negatively charged silane to form the silica shell), such that the process 2206 can include forming a positively charged external functionalized surface over the shell.

Figures 23A, 23B:
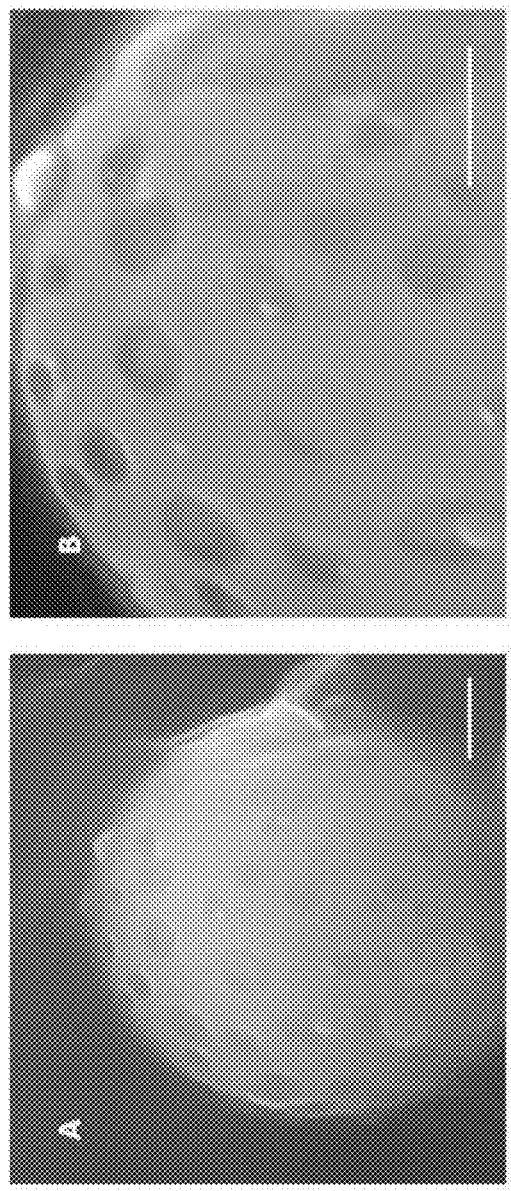
FIGS. 23A and 23B show SEM images of example resultant particles during implementations of the exemplary hollow porous nanosphere synthesis method of FIGS. 22A and 22B.

FIGS. 23A and 23B show SEM images of example resultant particles during implementation of the exemplary hollow porous nanosphere synthesis method. The exemplary scale bar in FIGS. 23A and 23B represents 200 nm.

The exemplary method includes a process to form a polymer coated template. For example, a specific amount of 1 μm carboxylate-modified polystyrene is diluted in DI water; and to this solution, $NH_4OH$ (29%) and Polydiallyldimethylammonium chloride (PDDA) is added respectively in a vigorously stirred solution. The polymer coated template formation process can include allowing a reaction to take place, e.g., for 20 minutes. The polymer coated template formation process can include washing the solution, e.g., by centrifugation for 15 min at 3200 g, and re-suspending the pellet in DI water thrice. The pellet is then re-suspended in DI water. The polymer coated template formation process can include adding an amount of Poly (acrylic acid) (PAA) while the solution is stirring, e.g., in which this process allows opposite charged polyelectrolye (PAA) to assemble on PDDA. The reaction is allowed for 20 minutes. The polymer coated template formation process can then include washing the solution, e.g., by centrifugation for 15 min at 3200 g, and re-suspending the pellet in DI water thrice. The final dispersion can be performed in 80% Ethanol in DI water.

The exemplary method includes a process to attach the satellite particles to the polymer coated template particle. For example, the 1 μm PAA/PDDA coated carboxylate-modified polystyrene particles in 80% ethanol can be incubated with specific amount of 100 nm amino-modified polystyrene for 30 minutes. The solution is then washed thrice by centrifugation for 5 min at 1000 g. Final dispersion was performed in ethanol. The satellite particle attachment process can include a final dispersion was performed in ethanol.

The exemplary method includes a process to functionalize the silica by amine surface functionalization. For example, ethanol can be added to the produced solution. The functionalization process can include stirring the solution vigorously. The functionalization process can include adding a small amount of N-(Trimethoxysilylpropyl)-N,N,N-trimethylammonium chloride, 50% in methanol (QuATPmS) to stirred solution. The functionalization process can include allowing a stirred reaction to take place, e.g., for 2 hours, before heating it up to 60° C., for example, while stirring for another 2 hours. The functionalization process can then include washing the reacted solution in DI water by centrifugation, e.g., for 15 min at 3200 g thrice.

The exemplary method includes a process to remove the exemplary polystyrene. For example, the template removal process can include placing the template particles in an excess of DMF while stirring and heating at 100° C. for overnight. The template removal process can include centrifuging the sample and re-suspending in DMF, e.g., repeated three times. The template removal process can include washing the particles in water to remove the traces of DMF.

Exemplary Embodiments of Hollow Nano Gold Golf Balls and Wiffle Balls

Hollow, porous nanoparticles such as nano-carriers, nano-liposomes, nanoshells, mesoporous natural organic materials have wide applications ranging from catalysis, photonics and biosensing to delivery of therapeutic and diagnostic agents. Many of these hollow nanostructures are made of silicon-based materials or organic polymers and are commonly coated with other metals and self-assembled organic molecules for task-oriented functionalization. Exemplary embodiments of such porous and hollow porous nanostructures and their fabrication methods using a template synthesis scheme are described. For example, exemplary fabrication methods described below are capable of producing (i) a nanoscale ball with a solid silica core and gold surface with pits (e.g., a nano golf ball), and (ii) a nanoscale ball with a hollow gold shell and pores on the surface, e.g., without silica (e.g., a nano wiffle ball), among other carrier structure designs. In some implementations, for example, the template was created by placing negatively charged, 100 nm diameter polystyrene bead in contact with a positively charged, 1 micron diameter silica core. Subsequent gold plating and the dissolution of the polystyrene bead produced a gold shell with equally spaced diameter pits (e.g., 100 nm), mimicking a golf ball. In addition, by dissolving the silica core, a hollow golf ball with pores was created. The disclosed template strategy of the exemplary fabrication method could be adapted to other metals and oxides.

Exemplary hollow, porous micro- and nano-particles of the disclosed technology can be used in a variety of applications including catalysis, photonics, biosensing, nanodelivery of therapeutic and diagnostic agents, cell culture, and toxin scavenging. Such structures are useful for encapsulation and storage as well because of the presence of the pores. The nanoparticles can be surface modified with other elements, such as gold or self-assembled organic molecules that allow task-oriented functionalization. This additional functionality can include responsiveness to light, temperature, pH, and other environmental cues.

Gold in general has many highly attractive photophysical properties that make it useful for imaging as well as thermal manipulations, e.g., including surface plasmon resonance (SPR), surface enhanced Raman spectroscopy (SERS), and photothermal heating. In biological applications, gold is biocompatible and modifiable with thiol containing ligands and targeting molecules.

Creating hollow, porous gold nanostructures is also attractive because of its optically responsive surface and its capability for storage or catalysis. Previous attempts at making such nanostructures have been limited to the large size (tens of micron size range). Using the disclosed techniques, for example, gold shell golf balls and hollow gold wiffle balls can be designed and created in controllable sizes (e.g., 200 nm and 1 µm diameters, as shown in the exemplary implementations described here) with controllably sized features, e.g., pit and pore sizes, which demonstrates the scalability of the present nanostructure fabrication technology.

Exemplary implementations were performed to fabricate and characterize exemplary nanoscale and microscale gold golf balls and gold wiffle balls. The following exemplary materials were used. Colloidal polystyrene spheres with carboxylate modified surfaces (PS-COOH, 2.73 wt % in water) with 100 nm diameters, spherical colloidal silica ($SiO_2$) with 200 nm or 1000 nm diameters (2 wt % in water), and poly(diallyldimethylammonium chloride) (PDDA) $M_w$~8,500 (28 wt % in water) were obtained. Tetrakis(hydroxymethyl)phosphonium chloride (THPC) (80% solution in water) and sodium hydroxide (NaOH, 10 M) were obtained. Potassium carbonate ($K_2CO_3$), formaldehyde (37%), ammonium hydroxide ($NH_4OH$) (29.79%), hydrofluoric acid (HF, 48%), and dimethylformamide (DMF), and anhydrous ethyl alcohol (EtOH) were obtained. Chloroauric acid ($HAuCl_4$) was obtained as a powder and prepared as a 1 wt % solution in water. The water used in all implementations was produced using a Millipore Advantage A10 system with a resistance of 18.2 MΩ.

The exemplary fabrication method can include a process to functionalize the surface of the silica particles with PDDA. Colloidal silica has a net negative surface charge at a pH values above ~2.2. The net charge on the surface of colloidal silica can be reversed using a cationic polyelectrolyte such as PDDA. PDDA electrostatically binds to the surface and reverses the net charge on the surface of colloidal silica. The stoichiometric formation of salt linkages between the quaternary ammonium ions in the polymer and the deprotonated silanol groups of the colloid. This was performed by adding 320 µL of ammonium hydroxide to 5 mL of 2% dispersions of colloidal silica (pH≳11). Subsequently, the solution was placed in an ultrasonic ice bath at 4° C., and then 5 mL of 1 w % t aqueous PDDA solution was added into the mixture. The resulting solution was left in the ultrasonic bath for 20 min. The tube containing the solution was then centrifuged at 3200 g for 10 min to remove unadsorbed polymer. Centrifugation and re-dispersion was repeated four times with a change to a clean container in between. On final rinse, the silica pellet was re-dispersed in 5 mL of water.

The exemplary fabrication method can include a process to synthesis the template. For example, negatively-charged satellite colloidal polystyrene spheres were attached to the larger cationic silica cores. Carboxyl-functionalized polystyrene spheres ~100 nm in diameter were electrostatically attracted to the 1000 nm PDDA-functionalized silica. For example, in a 2 mL centrifuge tube, 1 mL of the PDDA-functionalized silica was centrifuged at 3200 g and re-dispersed in 1 mL of EtOH. The tube containing PDDA-functionalized silica solution was placed in an ultrasonic ice bath at 4° C. for 10 min. Then 25 µL of aqueous carboxyl-functionalized colloidal polystyrene was added to the PDDA-functionalized silica and left in the ultrasonic ice bath for an additional 5 min. The mixture was then centrifuged at 1000 g for 5 min, decanted, and the pellet was re-dispersed in 1 mL of water.

The exemplary fabrication method can include a process to attach gold seeds to the template. For example, colloidal gold nanoparticles with 1-3 nm diameters were used as gold seeds for the gold plating process. In these exemplary implementations, the utility of the colloidal gold seeding solution was dependent on the order and method by which the reactants were mixed during their synthesis. For example, they were prepared by mixing 54 mL of water and 50 µL of 10 M sodium hydroxide together. In a separate container, 12 µL of 80% THPC was diluted in 1 mL of water, and aged for 5 min before being added to the aqueous sodium hydroxide solution. The mixture was then stirred for an additional 5 min prior to the addition of 2 mL of 1 wt % $HAuCl_4$. The solution turned a brown-red color and was stirred for 30 min prior to storage at 4° C. (e.g., for 24 hours before use). The gold seed solution was aged 24 hours at 4° C. before use. THPC simultaneously reduces chloroauric acid and stabilizes gold nanoparticles in aqueous solution, leaving the gold nanoparticles with a negative charge. For example, assuming the bulk density of gold and complete conversion to 3 nm gold seeds, the gold seed concentration was $1.0 \times 10^{16}$ gold seeds/mL.

The gold seeds were attached to the templates by adding 100 µL of the template solution and 5 mL of the gold seed solution together while vigorously stirring. The solution was stirred at 45° C. for at least 30 min. To remove excess free gold seeds from the mixture, the solution was centrifuged at 1000 g for 10 min. This centrifugation process was repeated at least 2 times. Finally, a reddish white pellet formed and was re-dispersed in 1 mL of water.

The exemplary fabrication method can include a process to grow the gold shell. For example, the gold seeds were grown into an interconnected gold shell structure (e.g., on the gold-seeded colloidal silica templates with the attached polystyrene satellites) through an exemplary electroless plating process. For example, a gold hydroxide ($Au(OH)_3$) stock solution (e.g., 183 µM) was prepared by stirring 70 mL of 5.37 mM $K_2CO_3$ aqueous solution for 10 min prior to the addition of 3.15 mL of 1 wt % $HAuCl_4$. The gold hydroxide solution was initially light yellow and became clear after 1 hour of stirring prior to refrigeration. The gold hydroxide solution was initially a light yellow color and became clear after 1 h of stirring prior to refrigeration. The solution was aged in the dark at 4° C. for 24 hours prior to use in plating. Then 500 µL of the gold-seeded templates were added to 15 mL of the gold hydroxide solution and mixed vigorously for 5 min followed by the addition of 50 µL of 37% formaldehyde. For example, the addition of formaldehyde starts the plating process by reduction of the gold hydroxide into metallic gold. This process step was quickly followed by the addition of 5 µL of 29% $NH_4OH$. For example, this causes the gold seeds to nucleate into a shell around the template. The resulting solution was mixed using a tumbler (e.g., a rotisserie) and tumbled for approximately 3 hours. The mixture was then centrifuged at 1000 g for 5 min, decanted to remove waste products, and re-dispersed in water. This process step was repeated at least 4 times. The pellet was re-dispersed in 2 mL of water.

The exemplary fabrication method can include a process to remove the template (e.g., by dissolution) and form the gold golf ball structures. For example, the gold golf balls were created when the 100 nm polystyrene satellites were removed, e.g., by solvent dissolution of the polystyrene by re-dispersing them in 5 mL of DMF after centrifugation. Gold plated templates were re-dispersed in 5 mL of DMF after centrifugation. The tube containing the solution was placed in an ultrasonic water bath for 20 min at 60° C. followed by centrifugation at 3200 g for 10 min and re-dispersing in DMF. Centrifugation and rinsing with DMF was repeated twice more before re-dispersing in water.

In some implementations of the method, for example, the exemplary fabrication method can include a process to remove the silica core and form hollow gold wiffle ball structures. For example, hollow gold golf balls were made by removing the silica core by dispersing the gold golf balls in 10% HF, e.g., while in 2 mL centrifuge tubes, in which the resulting mixture was left standing for 24 hours. The golf balls were centrifuged and etched with HF once more. The hollow gold balls (e.g., wiffle balls) were rinsed again (e.g., 6 times) by centrifugation with water and then re-dispersed in 2 mL of water.

Scanning electron microscopy (SEM) images were obtained, e.g., using a FBI XL30 SFEG UHR microscope at an acceleration voltage of 5 kV.

Figure 24:
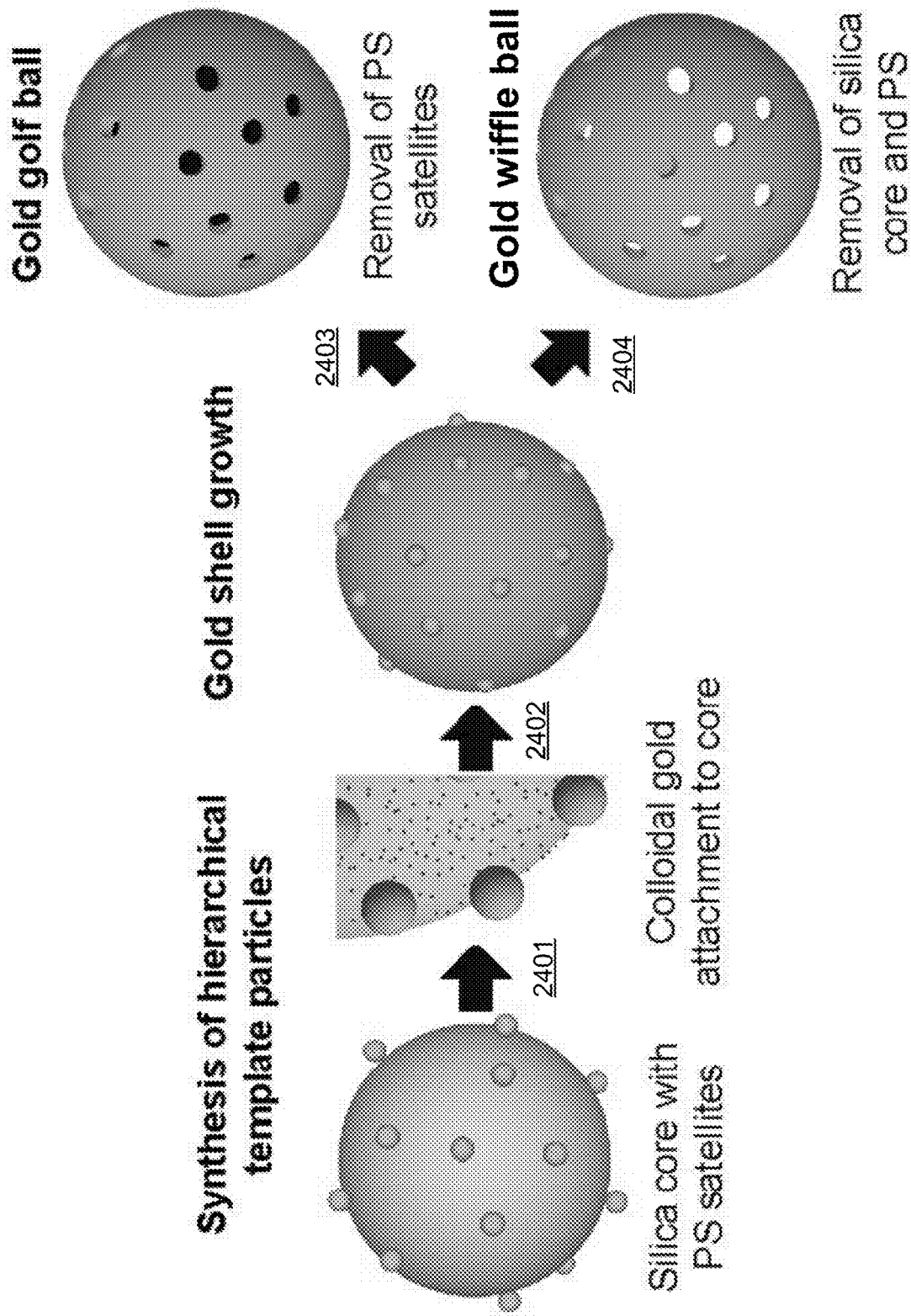
FIG. 24 shows an illustrative diagram of the exemplary synthesis method to fabricate porous nano-/micro-scale golf balls and hollow porous nano-/micro-scale wiffle balls.

FIG. 24 shows an illustrative diagram of the exemplary synthesis method to fabricate porous nano-/micro-scale golf balls and hollow porous nano-/micro-scale wiffle balls. The example shown in FIG. 24 produces gold nano golf balls and gold nano wiffle balls. As shown in the diagram, a silica core particle functionalized with a cationic polyelectrolyte (PDDA) with smaller polystyrene (PS) satellite spheres electrostatically attached is used to selectively attach nano-sized colloidal gold, in a gold seeding process 2401, onto its PDDA-functionalized silica core. An electroless plating process 2402 is shown depicting the growth of the nanosized gold seeds into an interconnected gold shell. Gold golf ball particles are synthesized by dissolution of the polystyrene satellites, as shown in the process 2403. In some implementations of the method, as shown in the process 2404, subsequent dissolution of the silica core completes the synthesis of the hollow porous gold wiffle ball particles.

Exemplary implementations of the exemplary synthesis method produced the following example results. The template was synthesized by attaching 100 nm carboxyl-modified polystyrene to a 1000 nm PDDA-functionalized silica core. By varying the concentration of the polystyrene spheres during the synthesis process, the amount of polystyrene spheres attached to the silica core could be controlled until saturated, in which an example was shown in the SEM image of FIG. 21A. This can be attributed to electrostatic repulsion limiting the number of polystyrene particles that can attach to the surface. Gold shell formation included the attachment of small gold seeds to the template and an electroless plating process that fills in the gaps between the seeds. For example, the gold seeds have a negative surface charge and are stabilized by a monolayer of THPC. This attracts the gold seeds to the surface of the positively charged PDDA-functionalized silica on the template. For a similar reason the negative surface charge of the seeds prevents attachment to the polystyrene on the template. These seeds in turn serve as nucleation sites for the next part of gold shell formation, in which an example was shown in the SEM image of FIG. 21B. Gold shell growth is completed by the reduction of gold ions into metallic gold. The growth preferentially happens on preexisting gold surfaces, i.e. gold seeded templates. As the seeds grow they come into contact with each other and eventually form a complete gold shell around the seeded parts of the template, where an example is shown in the SEM image of FIG. 21C.

After the gold shell is formed, the dissolution of the template particle can create either a gold golf ball particle (e.g., an example shown in the SEM image of FIG. 21D) or a hollow porous particle (e.g., an example shown in the SEM image of FIG. 21E). For example, by dissolving the polystyrene beads, a gold golf ball was created. Also, for example, dissolving the silica in a dilute solution of HF produced porous shells that are hollow inside. Further examination of the gold golf ball formation shows agglomeration does not happen with the current reaction conditions, where an example is shown in the SEM image of FIG. 21F.

The thickness and completeness of the gold shells are determined by the surface coverage of seeds on the template, kinetics of gold reduction, and the gold ion/template ratio. For example, the denser gold seeding on the template means the gold seeds do not have to grow as large in order to contact a neighboring seed. The saturation limit for gold seeds on silica has been observed to be about 30% surface coverage without salt. The density of gold seeding on the template cores may be expected to be near the saturation limit.

Figure 25A:
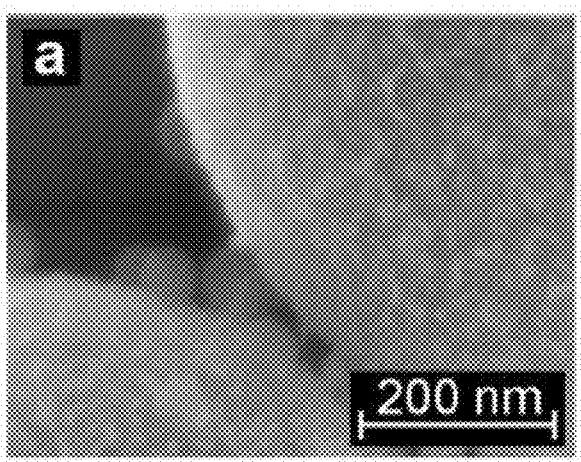
FIGS. 25A-25F show SEM images of exemplary gold plated template particles prepared with varying formaldehyde concentrations and gold ion concentrations.
Figure 25B:
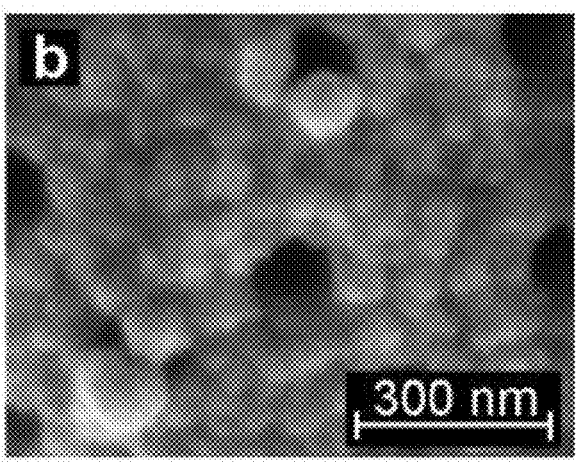
Figure 25C:
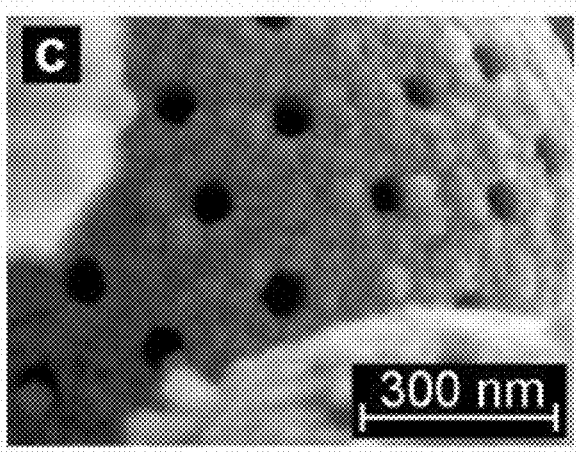
Figure 25D:
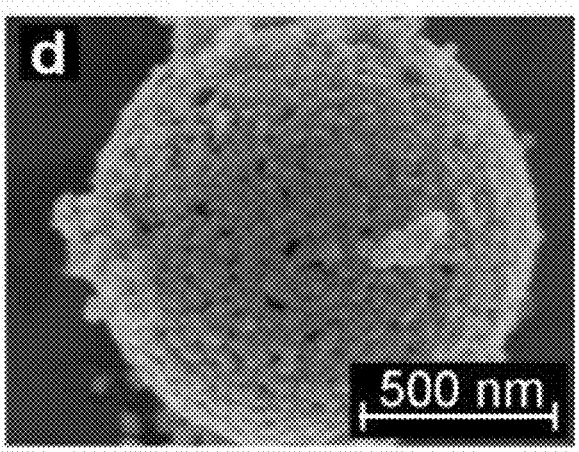
Figure 25E:
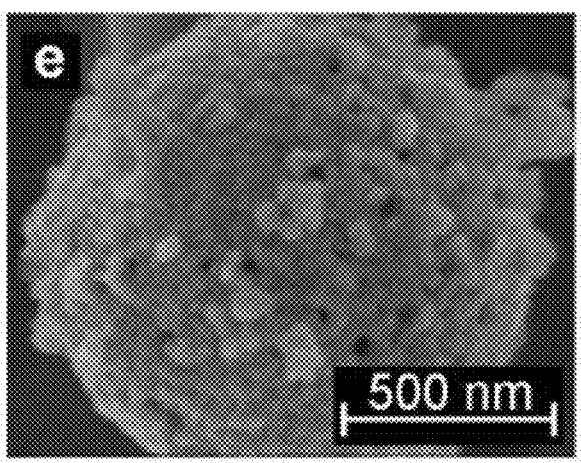
Figure 25F:
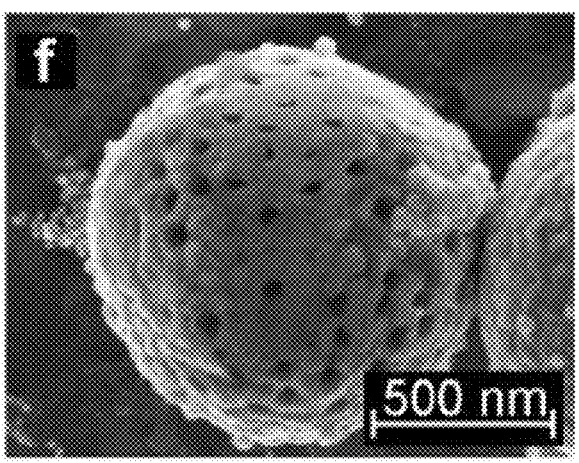

Gold shell growth on the template particles was controlled by varying formaldehyde concentration and gold ion concentration. FIGS. 25A-25C show SEM images of gold plated template particles using 15 mL of 183 µM gold hydroxide plating solution prepared with increasing formaldehyde concentration, e.g., 7 µL (FIG. 25A), 50 µL (FIG. 25B), and 100 µL (FIG. 25C); the exemplary scale bar represents 100 nm. FIGS. 25D-25F show SEM images SEM images of gold plated template particles using 50 µL of 37% formaldehyde with varying amounts of gold hydroxide solution, e.g., 2.5 mL (FIG. 25D), 5 mL (FIG. 25E), and 15 mL (FIG. 25F); the exemplary scale bar represents 500 nm. For example, assuming a well seeded template, thickness and completeness can also be limited by the kinetics of the formaldehyde/gold reaction. Since the reaction free energy is highly favorable, the gold deposition rate on the template is the dominant factor in the shell formation. Upon addition of formaldehyde, gold growth may not be enough to bring gold seeds in contact with each other. This results in an incomplete gold shell. To make a complete gold shell, higher concentration of formaldehyde is needed as shown in FIGS. 25A-25C. Gold coverage can also be limited if there is not sufficient amount of gold ion present in the solution to cover the templates. This is evident based on the exemplary results shown in FIGS. 25D-25F where increasing the volume of gold solution with the same amount of formaldehyde yields more complete and thicker gold shell. Using less gold, for example, the templates have distinct islands of gold that have not merged. With more plating solution, for example, the gold shell goes from spotty patches to a rough shell and eventually to a smoother shell. If a sufficiently thick shell is grown, the gold will envelope the polystyrene.

Figure 26A:
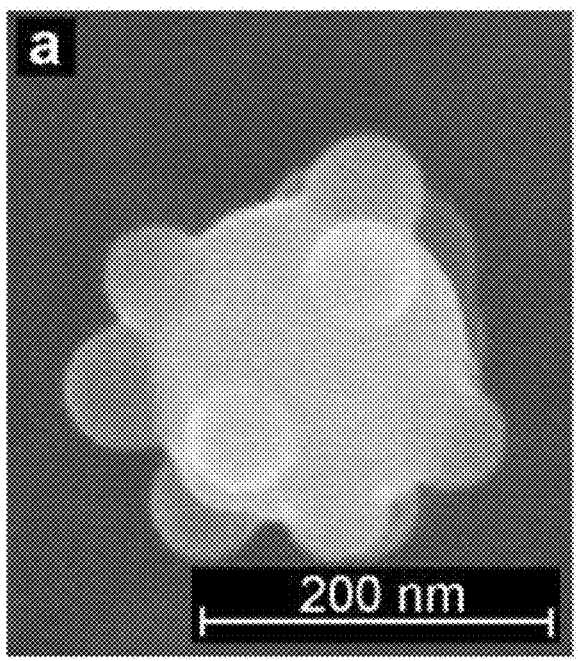
FIGS. 26A and 26B show SEM images from stages of the exemplary gold golf ball synthesis process using 200 nm cores.
Figure 26B:
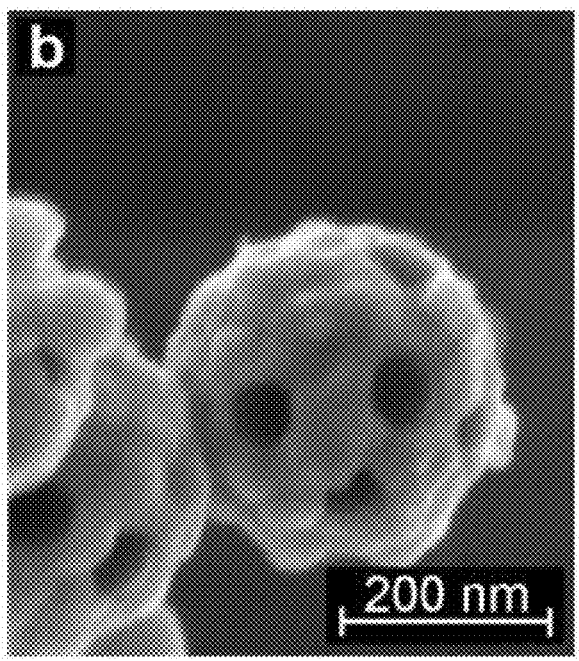

The exemplary implementations included producing smaller templates that were created with positive charged 200 nm PDDA silica cores and negative 100 nm carboxyl-modified polystyrene. FIGS. 26A and 26B show SEM images from stages of the exemplary gold golf ball synthesis process using the exemplary 200 nm cores. The SEM image in FIG. 26A shows the colloidal hierarchical template particles containing PDDA-functionalized 200 nm silica cores and 100 nm carboxylate-modified polystyrene satellites. The SEM image in FIG. 26B shows the particles after completion of the electroless gold plating process and before the removal of the polystyrene satellites.

Using the disclosed hierarchical template structure constructed of two different materials, two variations of the same particle (e.g., nano/micro golf balls and nano/micro wiffle balls) can be produced with potentially very different applications. For example, the pores of the gold golf ball have a silica bottom and may allow them to be selectively functionalized. The vacant center of the hollow gold wiffle ball offers storage capacity unavailable to the gold golf ball and may be used to store and release theranostic agents.

Exemplary Embodiments of the Disclosed Magnetically Guided Nanobowls

In some aspects of the present technology, techniques, systems, and devices are disclosed for fabricating and implementing composite nano-/micro-scale carriers that combine different properties on the same carrier, which can be used for a variety of applications including drug delivery, catalysis, and biological imaging. For example, using a template synthesis method of the disclosed technology, exemplary magnetic gold/silica nanobowls can be produced using an exemplary silica/polystyrene Janus template. The exemplary nanobowls can be fabricated to include a three-layer structure including a silica core coated with a gold shell and small iron oxide nanoparticles sandwiched in between. For example, in implementations of this exemplary fabrication method, selective gold plating only on the silica of the Janus template can ensure that only the exterior of the bowl is gold coated when the polystyrene in the template is dissolved away and leaving the silica interior. For example, this allows for a magnetically responsive nanobowl with a gold exterior and a silica interior.

Figure 27:
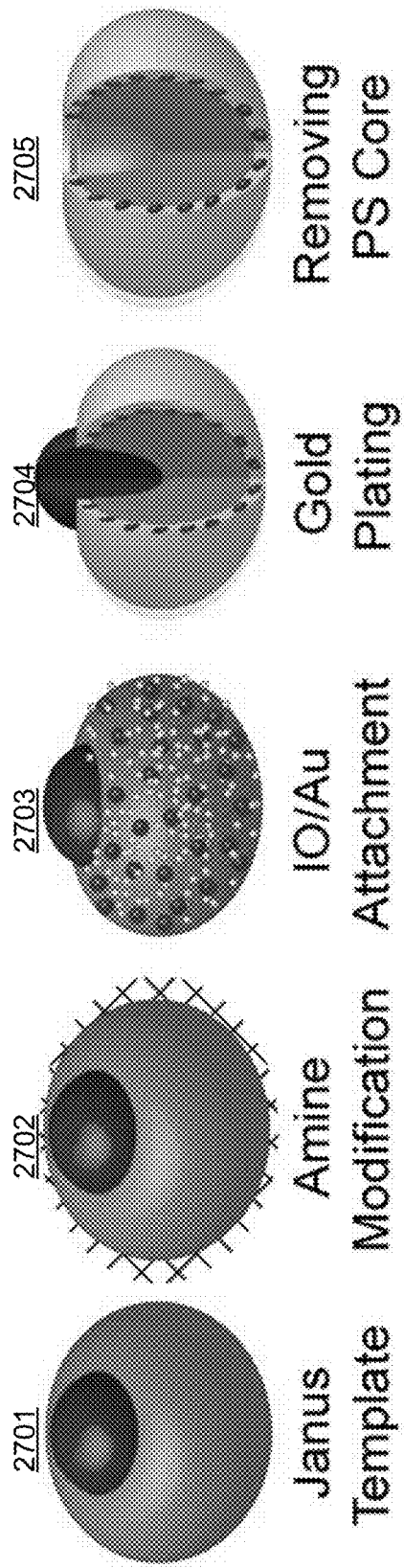
FIG. 27 shows an illustrative diagram depicting an exemplary fabrication method of the disclosed technology to produce exemplary composite magnetic nanoscale bowl-like structures ('nanobowls').

FIG. 27 shows an illustrative diagram depicting an exemplary fabrication method of the disclosed technology to produce exemplary composite magnetic nanoscale bowl-like structures ('nanobowls'). The method includes a process 2701 to synthesize a silica/polystyrene Janus template, e.g., such as in FIG. 12. In some implementations of the method, for example, the method can include a process 2702 to modify the surface to facilitate subsequent attachment of nanoparticles (e.g., to form an amine-functionalized surface on the silica/polystyrene Janus template). The method includes a process 2703 to attach nanoparticles to the Janus template, e.g., such as iron oxide and gold nanoparticles. The method includes a process 2704 to grow a shell over the Janus template. In some implementations of the process 2704, for example, the process 2704 includes reducing a gold chloride solution with the seeded templates (e.g., gold and/or iron oxide nanoparticles) dispersed within. In some implementations of the method, for example, the outer surface of the shell can be further modified. For example, in the case of a gold shell composite nanobowl, the gold surface is modified with polyethylene glycol to keep the particles well dispersed. The method includes a process 2705 to form an opening into the interior of the olive to form a nanobowl structure. For example, the gold covered templates are turned into magnetic bowls by dissolving the exposed polystyrene in organic solvent.

The exemplary fabrication method represents a bottom-up synthesis approach of a composite magnetic nanobowl with a gold exterior shell and a silica bowl. Exemplary implementations of the exemplary fabrication method and resultant composite magnetic nanobowl particles is described. For example, particles were constructed on an asymmetric silica/polystyrene Janus template-like templates including a silica shell around a partially exposed polystyrene core. The exemplary implementations show the formation of the resultant particles using electron microscopy, UV/vis & IR spectroscopy, and magnetometry, as well as show magnetically responsive transport of these example nanobowls. In addition Raman spectroscopy demonstrated that these particles provide an effective SERS platform.

Figure 28A:
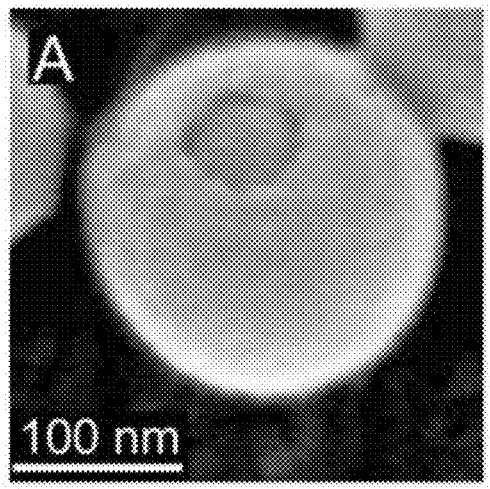
FIGS. 28A-28F show images including electron microscopy images of the exemplary particles produced using the exemplary fabrication method.
Figure 28B:
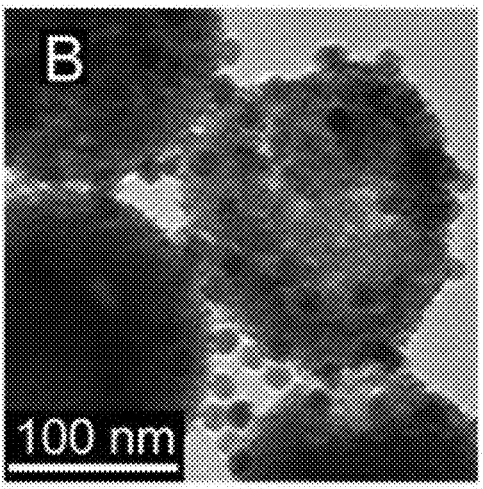
Figure 28C:
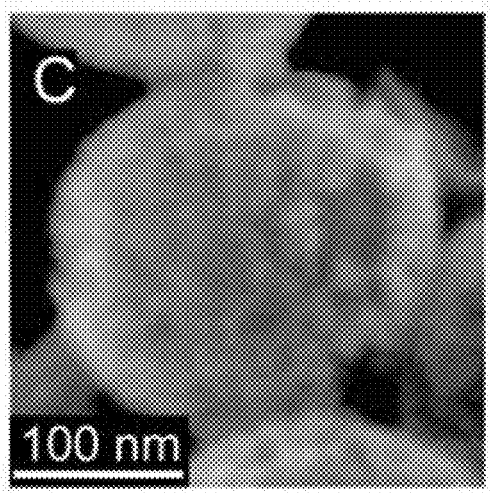
Figure 28D:
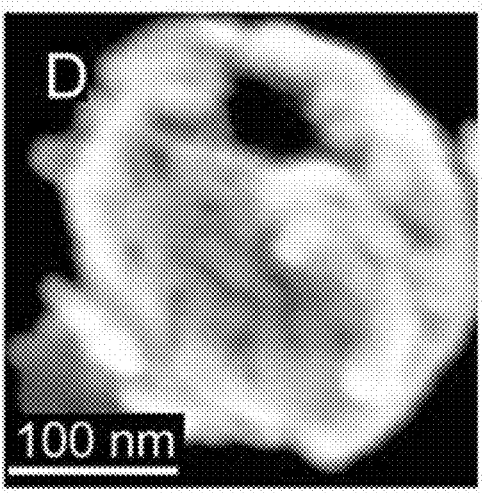
Figure 28E:
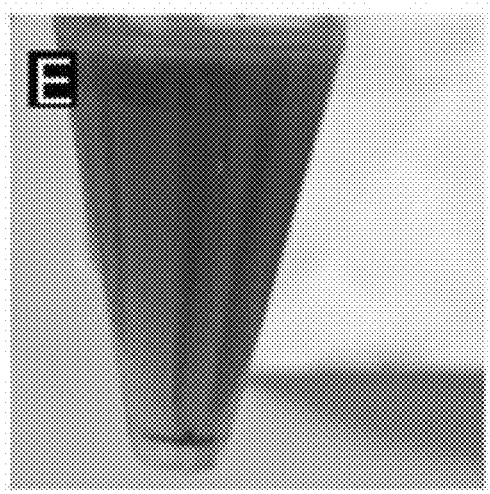
Figure 28F:
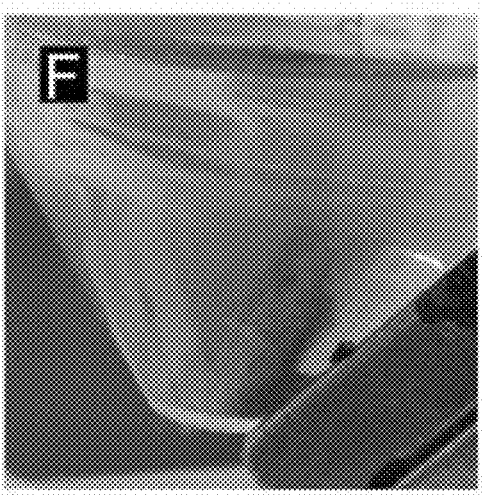

FIGS. 28A-28F show images including electron microscopy images of the exemplary particles produced using the exemplary fabrication method. FIG. 28A shows an electron micrograph of an exemplary Janus template formation (e.g., silica/polystyrene Janus templates). FIG. 28B shows an electron micrograph of exemplary gold and iron oxide nanoparticle attachment on silica. FIG. 28C shows an electron micrograph of an exemplary gold shell formation. FIG. 28D shows an electron micrograph of the removal of polystyrene core. FIG. 28E shows an image of exemplary gold plated particles in solution. FIG. 28F shows an image of exemplary magnetic gold/silica particles in solution attracted to magnet on the outside of the container.

The exemplary results shown in FIGS. 28A-28F provide visualization in the changes in morphology at each process. For example, modification of the Janus templates by an amine-silane (AEAPTMS) resulted in a positive surface charge, e.g., +20-30 mV as measured by zeta potential. For example, sequential attachment of negatively charged, 15 nm iron oxide (IONP) and 3-5 nm gold (AuNP) nanoparticles was performed, in which IONP were modified with a strong negative charge, and AuNP were synthesized from the reduction of chloroauric acid ($HAuCl_4$) with tetrakis (hydroxymethyl)phosphonium chloride (THPC) under basic conditions. For example, TEM images (not shown) of well-washed IONP/AuNP Janus templates showed dense surface coverage of both the larger IONP and the smaller AuNP.

Combination seeding and pH played a critical factor in proper seeding of the templates. In order for the seeded templates to remain stable in solution, a rapid reversion in charge is required when using electrostatic assembly methods. Amine modified templates would often aggregate when solely in the presence of IONP. Manufacturer supplied IONP was at a sub-saturation concentration and thus neutralized the surface change (e.g., zeta potential typically, −10 to +10 mV) rather than completely reversing it. For example, seeding with both IONP and gold at the same time was performed, e.g., because the gold seed concentration was sufficiently high to reverse the surface charge and stabilize the seeded templates. By adjusting the ratio of IONP and Janus templates, for example, the amount of IONP on the shell can be further optimized if needed. Also, for example, pH was a factor examined, e.g., because the gold seed solution is synthesized in basic conditions and remains highly basic (e.g., pH>9). At such high pH values, for example, aminated templates were generally neutral due to deprotonation of the majority of amines on the silica surface. Addition of IONP into the seeding solution did not lower the pH significantly and attempts to seed in these conditions resulted in heavy agglomeration. Adjustment of the pH with small amounts of 10 mM HCl to between 7-8 in the IONP/gold seed solution resulted in non-agglomerated templates and successful seeding of both IONP and gold as seen under TEM in FIG. 28B.

In the exemplary implementations, for example, a complete shell was formed by suspending the IONP/AuNP Janus templates in a $HAuCl_4$ plating solution and reducing the gold onto the templates, e.g., as shown in FIG. 28C. For example, poly(vinylpyrrolidone) (40 kDa) was added to the solution just before reduction because it improved gold surface coverage during the plating process. After formation of the gold shell, the now gold plated Janus template was suspended in DMF and the polystyrene was dissolved, e.g., as shown in FIG. 28D. The exemplary results of the exemplary implementations showed that the nanobowls displayed a deep teal color when suspended in solution (FIG. 28E), and can be magnetic attracted to the side wall of the container (FIG. 28F).

Figure 29:
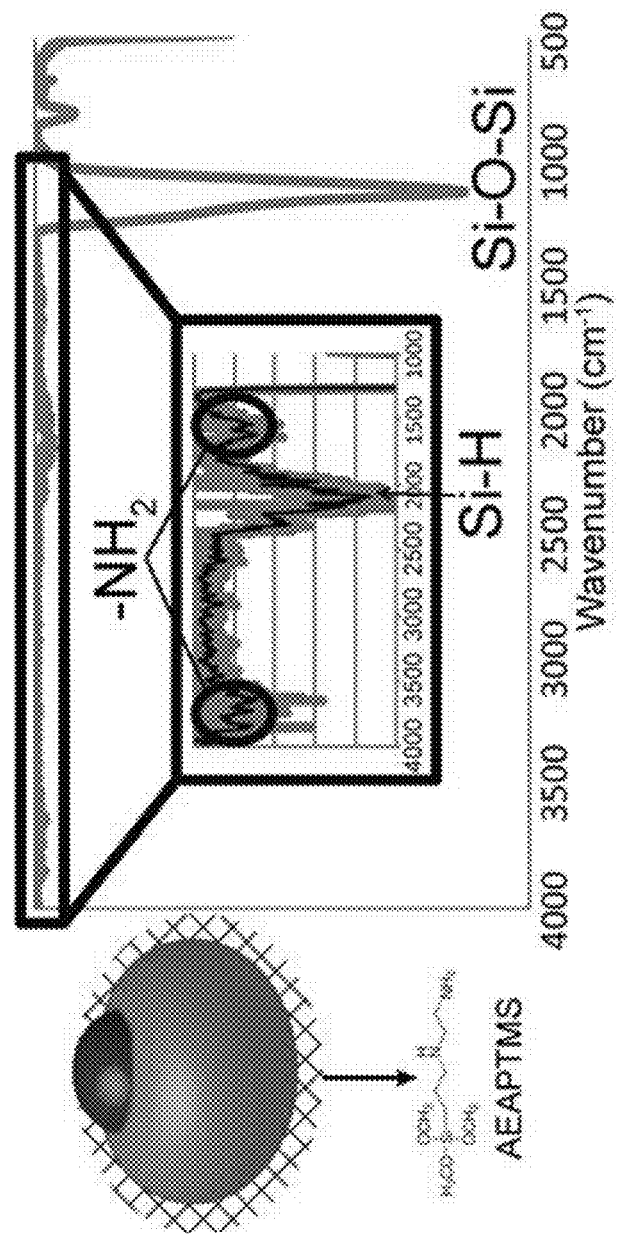
FIG. 29 shows an FTIR data plot of the amine-modified Janus template.

In the exemplary implementations, for example, different characterization modalities were used to confirm the completion of different processes. For example, after the Janus templates were formed, the surface of the Janus templates were modified with (3-aminoethylamino)propyl-trimethoxysilane (AEAPTMS) is confirmed with FTIR. FIG. 29 shows an FTIR data plot of the amine-modified Janus template. The spectrum showed peaks that correspond with primary amines at 1500 and 3600 cm$^{-1}$. In addition the siloxane and silylhydride bonds were seen more prominently at 1100 and 2100 cm$^{-1}$ respectively. These measurements confirm the present absorbance measurements of the gold nanobowls indicated the formation of absorbance peak at 840 nm, indicative of a gold shell around a silica core.

Figure 30A:
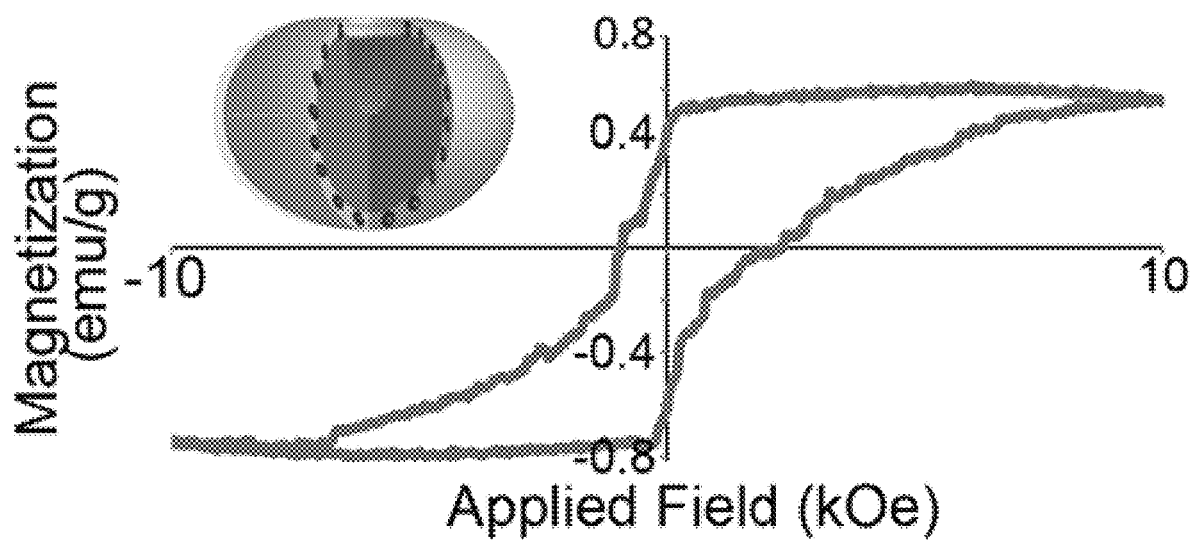
FIGS. 30A and 30B show magnetic hysteresis and UV/Vis data plots of the of shell of the exemplary nanobowls.
Figure 30B:
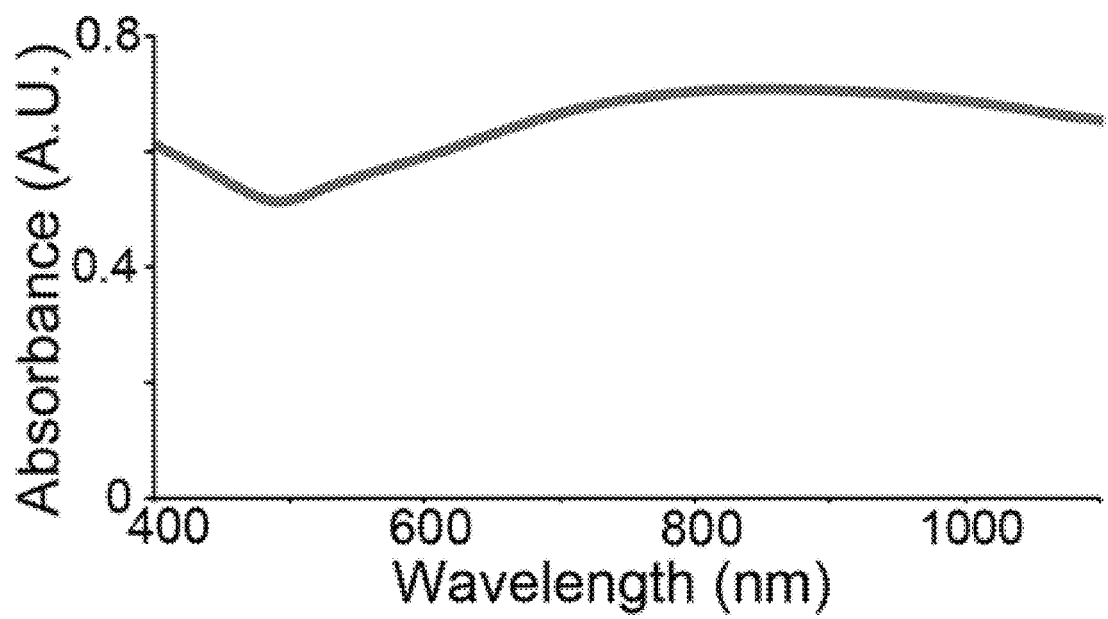

FIGS. 30A and 30B show magnetic hysteresis and UV/Vis data plots of the of shell of the exemplary nanobowls. FIG. 30A shows the magnetic hysteresis of the particles, which indicates the composite particle retains some ferromagnetic character despite using 15 nm ferromagnetic particles. FIG. 30B shows the UV/Vis spectrum of the gold plated nanobowls, e.g., in which the peak at 840 nm is indicative of successful gold shell formation. For example, the magnetic hysteresis of the particles were measured with a vibrating sample magnetometer and found to be slightly ferromagnetic. The saturating magnetization for the magnetic gold shell nanobowls is between 0.4-0.6 emu/g. The 15 nm IONPs were usually superparamagnetic at the 15 nm size, but in this particular case the composite particle appears to have retained some ferromagnetic character with a noticeable hysteresis.

Figure 31A:
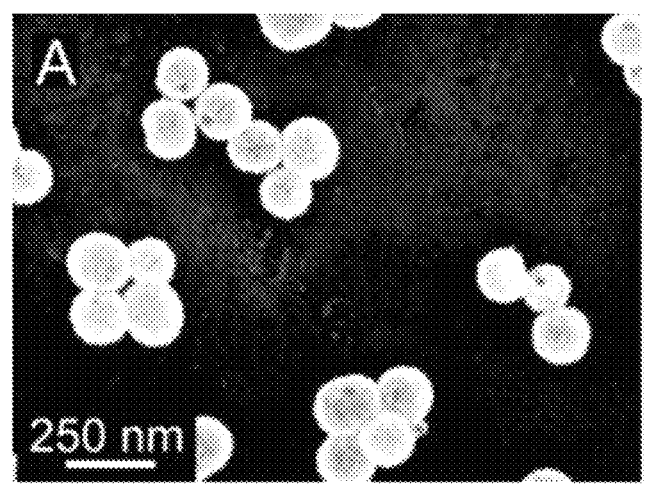
FIGS. 31A-31C show wide field images and data plots of exemplary functionalized magnetic gold-silica before and after removal of the polystyrene.
Figure 31B:
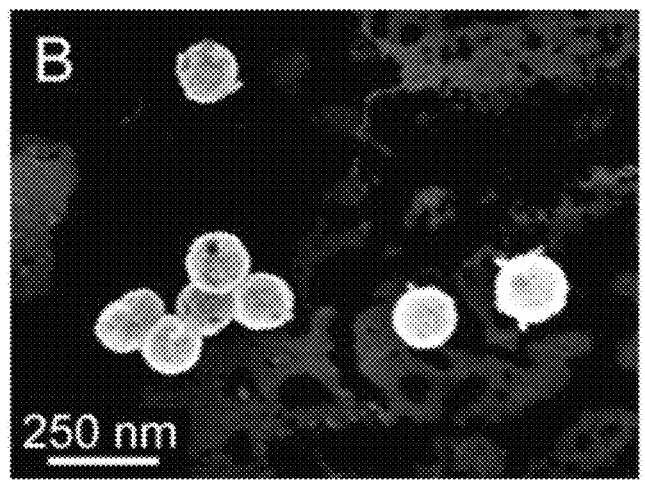
Figure 31C:
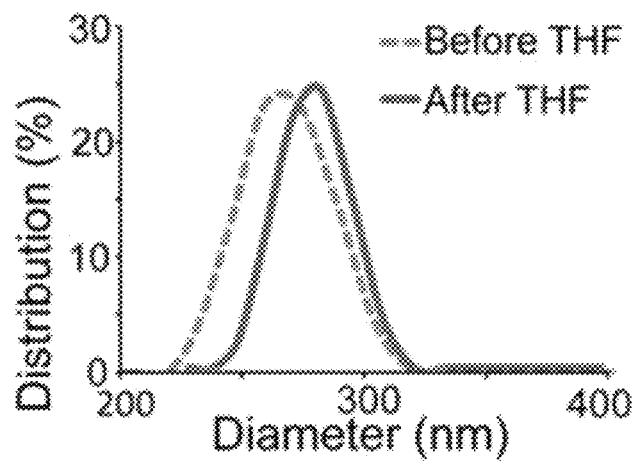

FIGS. 31A-31C show wide field images and data plots of exemplary PEGylated magnetic gold-silica before (FIG. 31A) and after removal of the polystyrene (FIG. 31B). FIG. 31C show accompanying DLS data for before (e.g., solid red, 264 nm) and after removal of polystyrene (e.g., dotted green, 282 nm). For example, the wide field images and DLS of the gold plated Janus templates and nanobowls demonstrated the monodispersity of the nanobowls. The PEGylated gold plated Janus templates show individual particles formed with complete formation of a gold shell over the external silica surface. The DLS data revealed a single peak at 264 nm of the sample shows good agreement with what is seen in the SEM image. After removal of polystyrene by THF, for example, the magnetic gold nanobowls were shown to be disperse under SEM (FIG. 31B) and DLS (solid line in FIG. 31C). The exemplary data from these exemplary implementations showed a slight increase in the average diameter to 282 nm, for example, but, running a t-test on the two curves showed that the two populations are statistically different from each other.

FIGS. 32A-32F show time lapse images and a data plot of the exemplary functionalized magnetic nanobowl guided through a hydrogel medium. For example, the exemplary PEGylated magnetic nanobowl was attracted through a GelMA-co-A6ACA hydrogel toward a Nd—Fe—B magnet (shown on the left in FIG. 32A). FIGS. 32B-32E show the exemplary time lapse images of the guided functionalized magnetic nanobowls through the hydrogel as time elapses from 0, 9, 27, and 52 hr, respectively. As shown in the time lapse images, for example, the gel becomes noticeably more teal color on the right as the nanobowls infiltrate the gel and exit on the left. Under higher optical magnification, for example, as shown in FIGS. 32F-32H, the gel at 9, 27, and 52 hr, respectively, show a teal colored front build up in the circled area on the right at 9 hours (FIG. 32F), move left and become more diffuse about two-thirds of the way through the gel at 27 hr (FIG. 32G), and most particles have passed through the gel at 52 hours (FIG. 32H). For example, the circled areas in FIGS. 32F-32H highlight the noticeable differences that can be seen in the gel as time progresses. FIG. 32I shows a data plot depicting exemplary line contrast scans between the dotted straight lines in each image show a greater amount of contrast on the right at 9 hour. The contrast levels out with both 27 and 52 hr, e.g., indicating most of the particles have passed through, leaving only traces of nanobowls behind. For the images shown in FIGS. 32F-32H, the distance between the dotted lines is 2 mm.

The exemplary data shown in FIGS. 32A-32H demonstrated the ability of the nanobowls to pass through porous materials with a time lapse images. In the exemplary implementations, for example, the gelatin-methacrylate-co-N-acryloyl 6-aminocaproic acid gel was laid on its side with a strong rare earth magnet at one in and imaged over a span of 52 hours. Pegylated nanobowls over the time course were attracted toward the magnet and the infiltration of the particles in the gel can be visualized as teal tint in a previously clear gel. For example, the gel become progressively more teal colored as the time goes on; and in closer examination a front of particles can be seen infiltrating the gel and diffusing throughout as time progresses.

Figure 33:
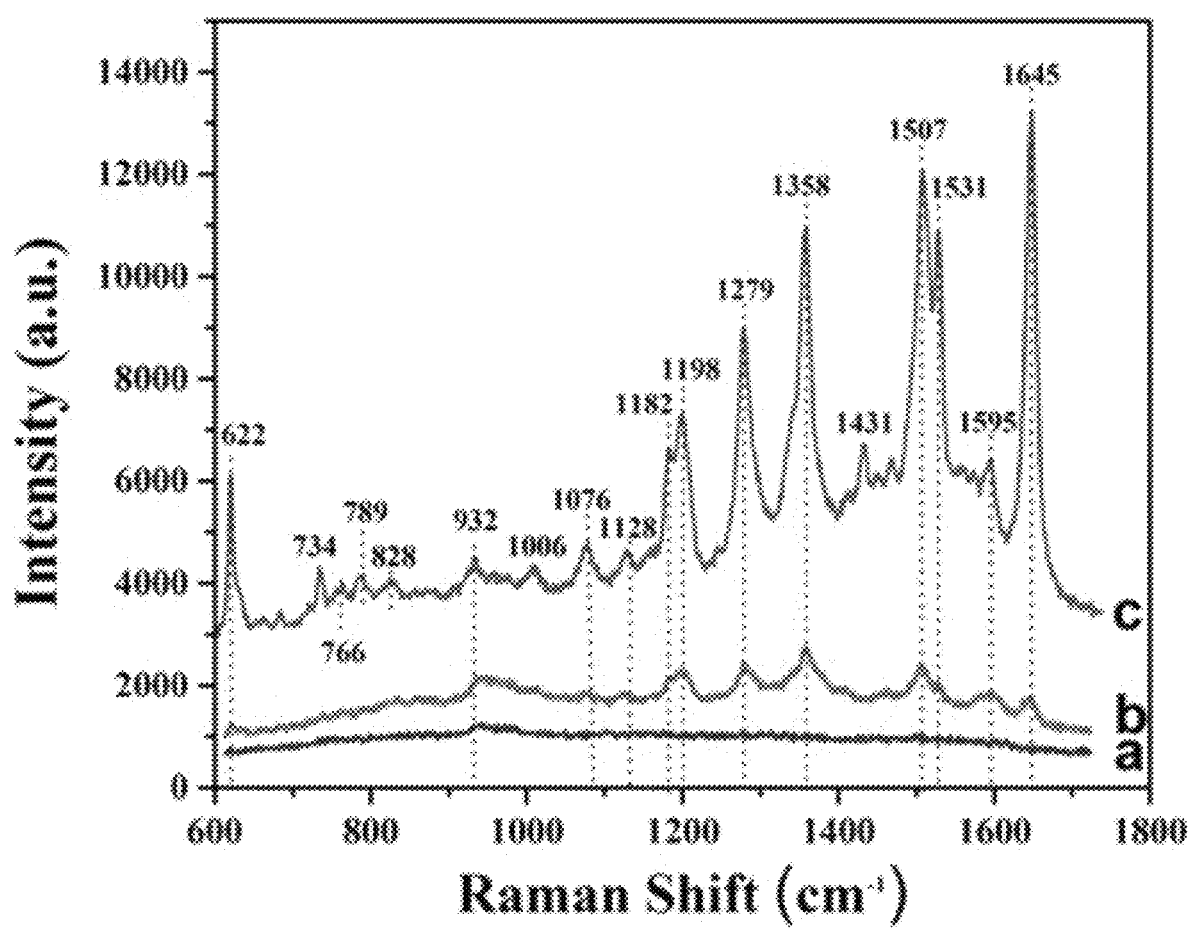
FIG. 33 shows a Raman spectral data plot of Rho B with and without exemplary gold/silica nanobowls.

In addition, the exemplary gold/silica nanobowls can be used as SERS platforms that combine the advantage of sensibility and specificity binding with a Raman reporter. The SERS activity of the exemplary nanobowls was tested, for example, using Rhodamine B (Rho B) as a probe molecule. SERS effect can be maximized when both the frequency of the excitation laser and Raman scattered phonons approach the resonance frequency of localized surface plasmon resonance. For example, the exemplary nanobowls presented a maximum absorption peak at 840 nm. Based on this, an exemplary 632 and 785 nm laser was used for Raman excitation in these exemplary implementations. FIG. 33 shows exemplary Raman spectra of Rho B with and without gold/Silica nanobowls. FIG. 33 shows a data plot of Raman Spectra of 0.1 M Rhodamine B in aqueous solution (spectra (a)); SERS spectra of 1×10$^{-6}$ M Rhodamine on gold/silica nanobowls, 150 mW of 632 nm excitation, 30 s acquisition (spectra (b)); and SERS spectra of 1×10$^{-6}$ M Rhodamine on gold/silica nanobowls, 150 mW of 785 nm excitation, 30 s acquisition (spectra (c)). As shown in the exemplary data, there was a dramatic increase of the Raman intensity, e.g., in which the SERS intensity on the gold/silica nanobowls excited with a 785 nm laser was ten-fold larger than that of single Rho B; and seven-fold more intense than that of the same sample using a 632 nm laser.

The disclosed magnetic gold shelled nanobowls can be used in a variety of applications such as drug delivery vehicle by sealing bowl with biocompatible materials, including liposomes, chitosan, and PLGA. For example, for conditional and controlled release of the therapeutic from the bowl, such a cap could be released by specific interaction with DNA, enzymatic processes, or environmental triggers like temperature and pH. For example, the disclosed nanobowls can be used for a magnetically-guided delivery and controlled on-demand release of imaging contrast molecules and therapeutic (theranostics) agents.

Exemplary Implementations on Core Size of Exemplary Janus Particles

Exemplary implementations and results are described that examine the role of the carboxylated polystyrene (cPS) core size on the cPS-silica Janus particle morphology (e.g., its size and shape). For example, two different silica sizes and five different cPS core sizes were studied in these exemplary implementations. Exemplary results from electron microscopy (EM) and dynamic light scattering (DLS) analysis indicated that the composite cPS-silica particle acquired two distinct shapes, e.g. (i) when the size of the cPS core is much smaller than the non-cPS silica (b-$SiO_2$) sphere, partially encapsulated Janus particles are formed, and (ii) when the cPS core is larger than or equal to the b-SiO2 sphere, e.g., a raspberry-like structure rather than a Janus particle is formed. For example, cPS-silica Janus particles of ~100 nm-500 nm size were obtained when the size of the cPS core was much smaller than the non-cPS silica (b-SiO2) sphere. The exemplary scalable nanoscale Janus particles will have wide application in multifunctional delivery theranostics platform and catalysis.

For example, the described exemplary implementations examine the cPS core size-dependence on the cPS-silica morphology, e.g., where cPS-silica particles were created by adding cPS cores of varying core sizes (e.g., 50-1000 nm) to make small (e.g., ~180 nm) and large (e.g., 380 nm) b-$SiO_2$ nanoparticles. The reaction conditions for producing the exemplary small b-$SiO_2$ and the large b-$SiO_2$, respectively, are referred to here as "small recipe" and "large recipe". The core size dependence on the cPS-silica particle's morphology was evaluated using the size of b-$SiO_2$ nanoparticles as reference; and the particle morphology was evaluated using TEM, SEM and DLS. Without any cPS cores, the above-mentioned recipes created small (e.g., ~180 nm) and large (e.g., ~380 nm) diameter b-$SiO_2$ nanoparticles.

Figure 34:
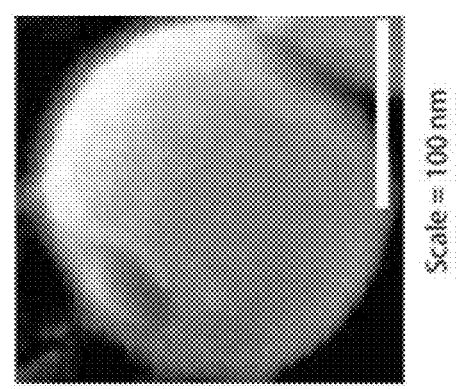
FIG. 34 shows an illustrative diagram and accompany image of exemplary cPS-silica Janus particles formed when carboxylated polystyrene particles are added into a silica sol-gel reaction.
Figure 34:
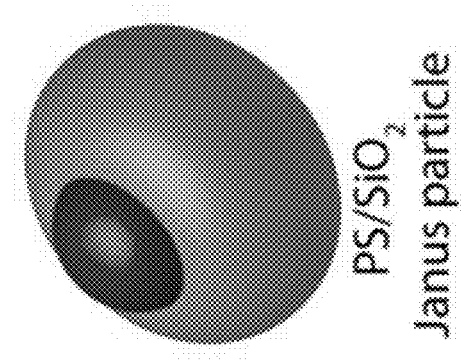
Figure 34:
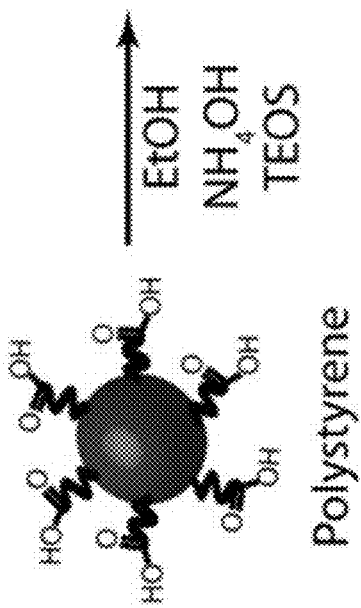

FIG. 34 shows an illustrative diagram and accompany image of exemplary cPS-silica Janus particles formed when carboxylated polystyrene particles are added into a silica sol-gel reaction. The formation of cPS-silica Janus particles were first observed after the addition of cPS at the start of a sol-gel reaction. As shown in FIG. 34, these particles can be identified by a smooth silica shell and with distinct depressions right at the surface where the silica meets the cPS. These depressions are easily recognizable in SEM images because of the distinctive circular mark in the silica.

Size dependence was first investigated by keeping the reaction volume constant. Four cPS cores of different diameters (50 nm-400 nm) were examined for the smaller recipe, while five different cPS cores (50-1000 nm) were examined for the large recipe.

Figure 35A:
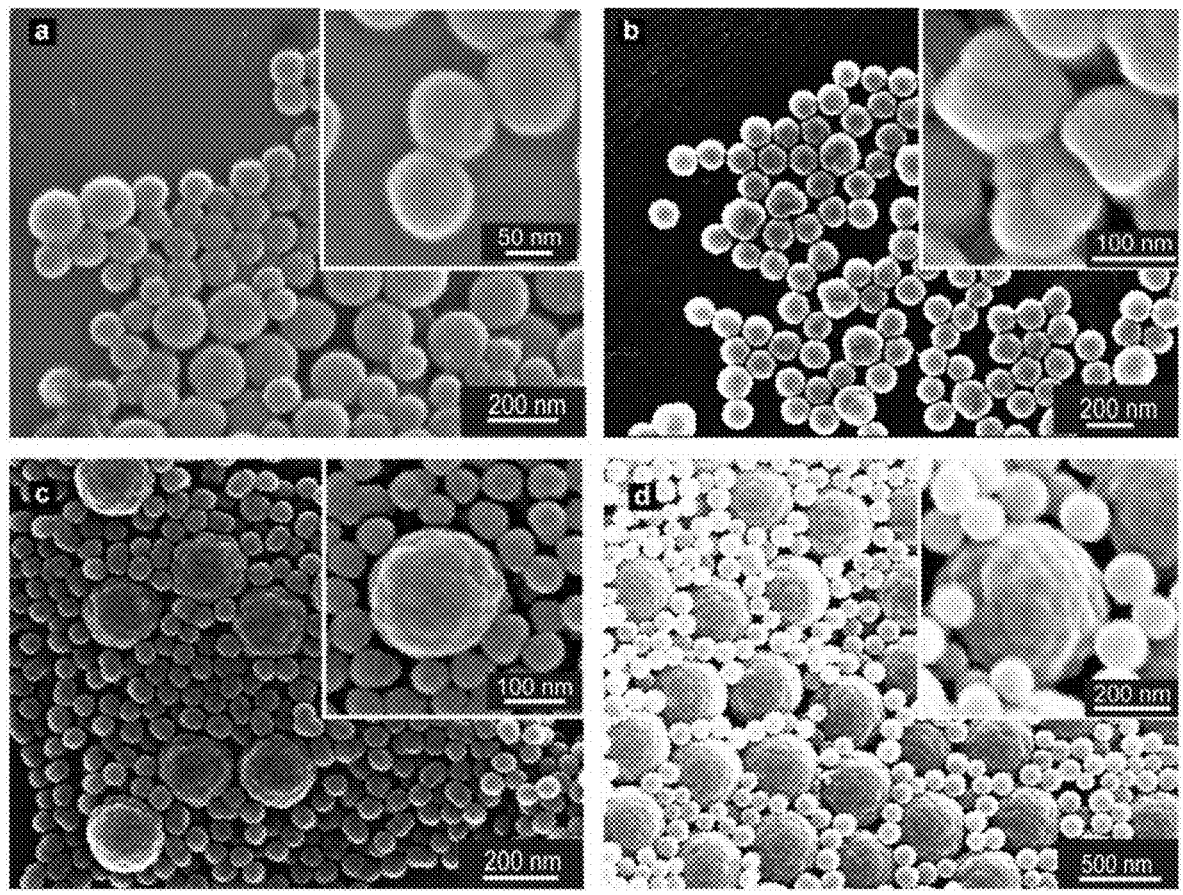
FIG. 35A shows an images of exemplary particles produced using the small silica fabrication process with different diameter cPS cores.
Figure 35B:
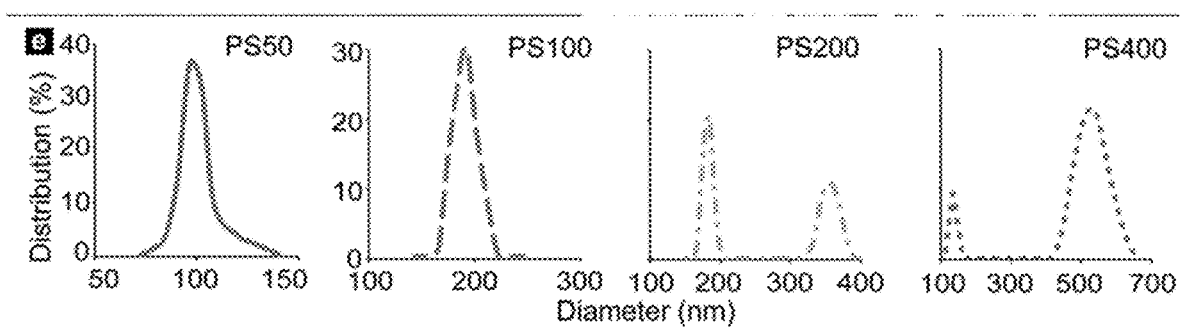
FIG. 35B includes DLS histogram data plots.

FIG. 35A shows an images of exemplary particles using the small silica process with different diameter cPS cores, e.g., 50 nm in image (a), 100 nm in image (b), 200 nm in image (c), and 400 nm in image (d). Each of the images in FIG. 35A includes wide field image insets, which show a more detailed image of the exemplary cPS-silica particles. The small silica process with addition of 50 nm core sizes created uniformly-sized Janus particles. The addition of 100 nm cores created particles with multiple silica shells attempting to cover the core. As the cores become larger (e.g., 200, 400 nm), silica formed around the larger cores in a lumpy shell and excess silica coalesced into smaller particles. For the smaller ethanol recipe, cores smaller (e.g., 50 nm) than the small b-$SiO_2$ formed well-defined Janus particles, as shown in image (a) of FIG. 35A. However, when the PS core diameter became similarly sized or much larger than b-$SiO_2$ particles, the silica started to coat the cPS in clumps, as shown in image (b) of FIG. 35A. The clumps became more numerous and a defined raspberry-like shell formed as the core sizes increased, as shown in images (c) and (d) in FIG. 35A. The silica completely coated the cPS, leaving the excess TEOS to form the pure silica particles surrounding it. The formation of the raspberry shell and Janus particles were also relatively uniform as can be seen in wide-field images. FIG. 35B includes histogram data plots showing the corresponding DLS distribution.

Figure 36:
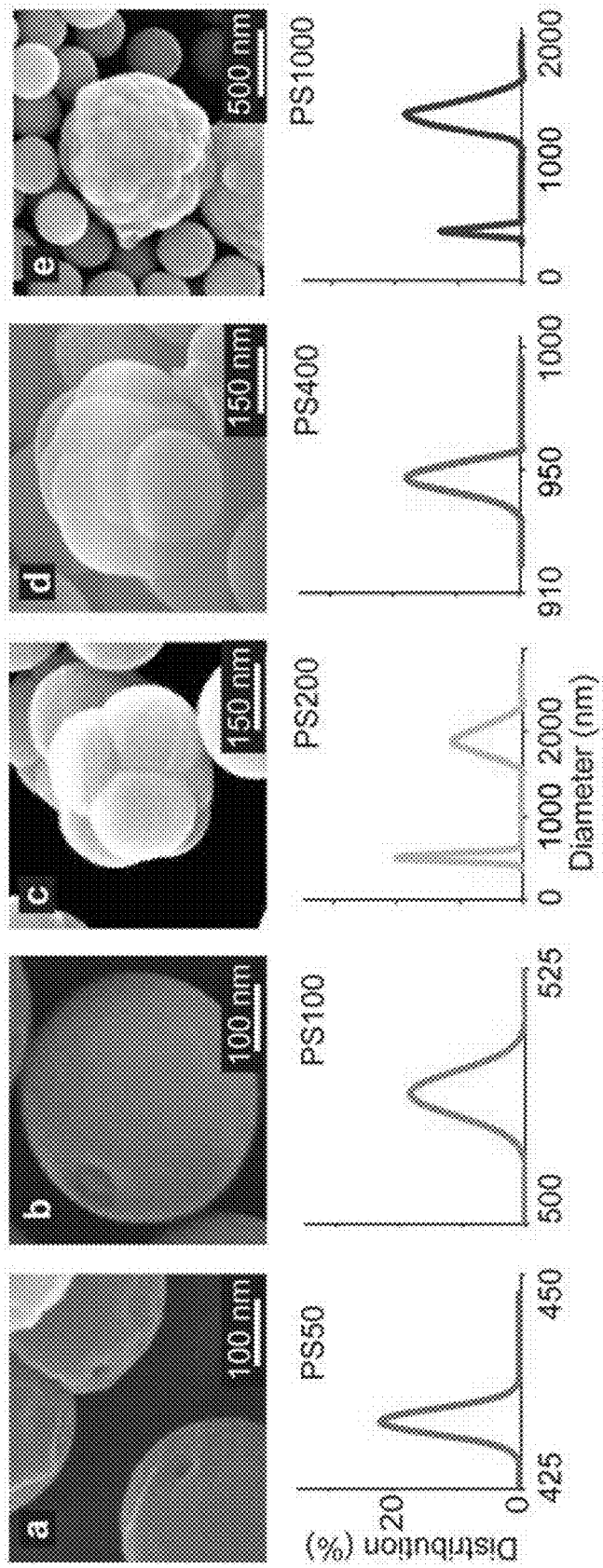
FIG. 36 shows an electron micrographs and accompanying DLS histograms of exemplary particles produced using the large silica fabrication process with different diameter cPS cores.

The exemplary implementations showed a similar trend emerged when the cPS core size was varied using the large silica recipe. FIG. 36 shows an electron micrographs and accompanying DLS histograms of exemplary particles produced using the large silica fabrication process with different diameter cPS cores. For example, the images and corresponding histograms include the following cPS core sizes: 50 nm in image (a), 100 nm in image (b), 200 nm in image (c), 400 nm in image (d), and 1000 nm in image (e). The 50 and 100 nm core sizes correspond with partial encapsulation around the core. The medium sized core (e.g., 200 nm) demonstrated formation of raspberry-like shells. The much larger cores (e.g., 400, 1000 nm) showed the cPS cores covered with a raspberry-like shells with larger clumps of silica than the shell formed with the small silica processes. DLS histograms revealed the formation of larger structures and confirmed smaller silica particles. When 50 nm cores were used multiple cores appeared to be almost fully encapsulated in a single Janus particle, as shown in panel (a) of FIG. 36. When 100 nm cores were used cPS's encapsulation by silica is noticeably reduced, as shown in panel (b) of FIG. 36. In addition, cPS-silica Janus particles formed with smaller cPS cores (e.g., 50-100 nm), but with a larger diameter than corresponding particles in the smaller recipe. Using mid-sized cores (e.g., 200, 400 nm) that approached the particle size of large b-$SiO_2$, for example, a complete silica shell was formed with varying levels of bumps. For example, the exemplary 200 nm core showed a complete silica shell with a few defined bumps around the shell as shown in panel (c) of FIG. 36. For example, the exemplary 400 nm core showed a greater progression of this trend as more bumps can be seen forming on the outside of the cPS cores, as shown in panel (d) of FIG. 36. When the core is much larger (e.g., 1000 nm) than b-$SiO_2$, for example, the lumps appeared to be very pronounced on the silica surface, as shown in panel (e) of FIG. 36.

Figure 37:
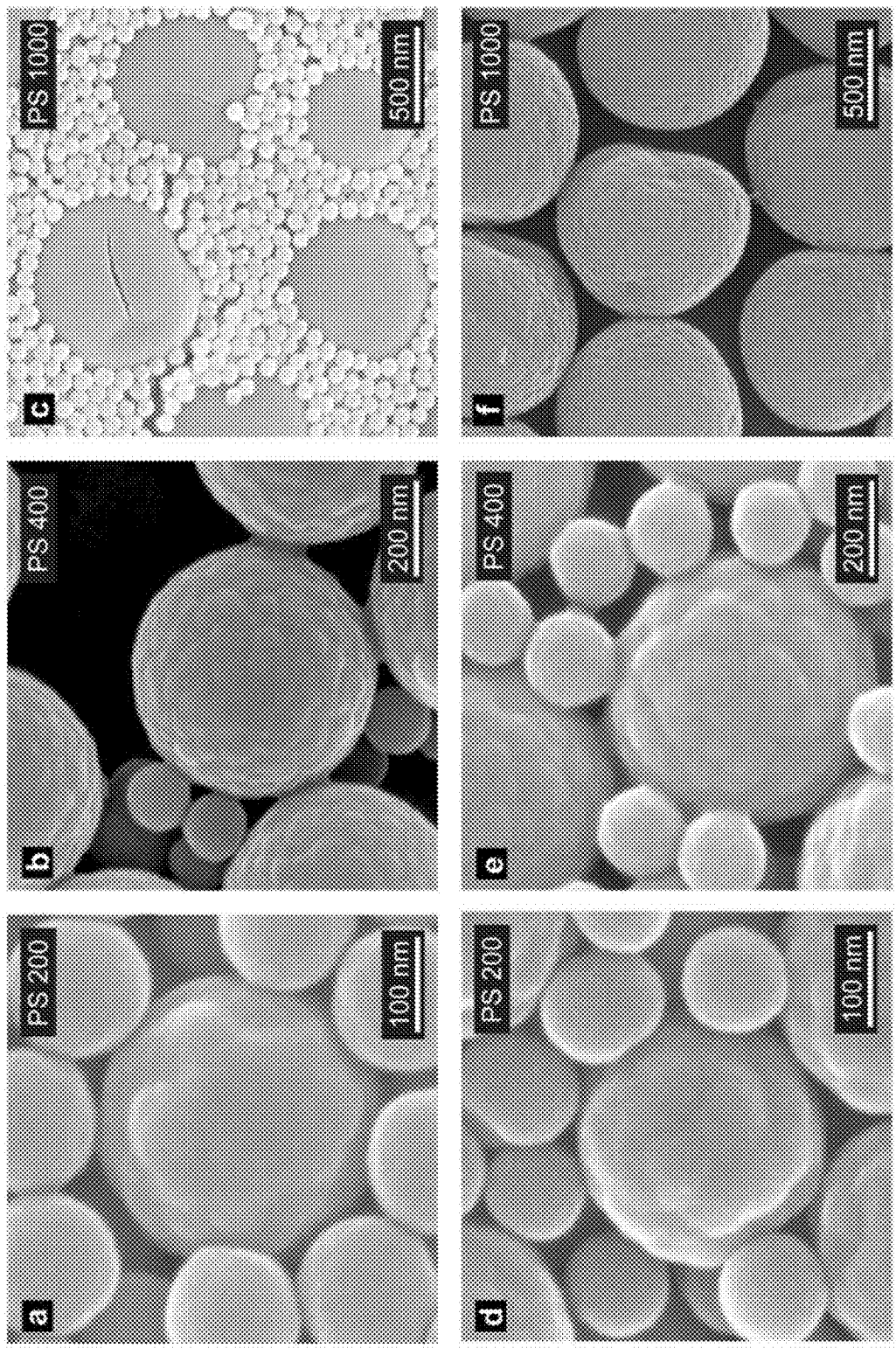
FIG. 37 shows images of exemplary PS/silica composites produced by the exemplary small silica process created by varying the TEOS/PS ratio.

The formation of raspberry-like shells (e.g., cPS core>b-$SiO_2$ particle) may be a result of different TEOS/cPS ratios instead of the core size. To account for this possibility, the ratio of TEOS to cPS was held constant for different core sizes made with the same recipe. FIG. 37 shows images of exemplary PS/silica composites produced by the exemplary small silica process created by varying the TEOS/PS ratio at $10^{10}$ (images (a), (b), and (c), and at $10^9$ (images (d), (e), and (f)). For example, as the core size increases from 200 nm (e.g., images (a), (d)), to 400 (e.g., images (b), (e)), and to 1000 nm (e.g., images (c), (f)), the bumps were observed to be more noticeable and numerous than the larger silica process. From the exemplary results of the exemplary implementations, it appeared that as the core size increases, the silica shell begins to smoothen out (e.g., image (c)) or coalesce (e.g., image (f)), e.g., depending on the TEOS/PS ratio. The excess silica coalesces into smaller silica particles and is noticeable as smaller spheres. From these SEM images, raspberry-like silica shells coated all cPS cores and any excess TEOS in solution formed silica nanoparticles. Changing the TEOS/PS ratio did not affect the overall morphology of the shells. In addition at the same TEOS/PS ratio the shell developed more noticeable bumps as well as a greater number of bumps as the core size increases.

Figure 38:
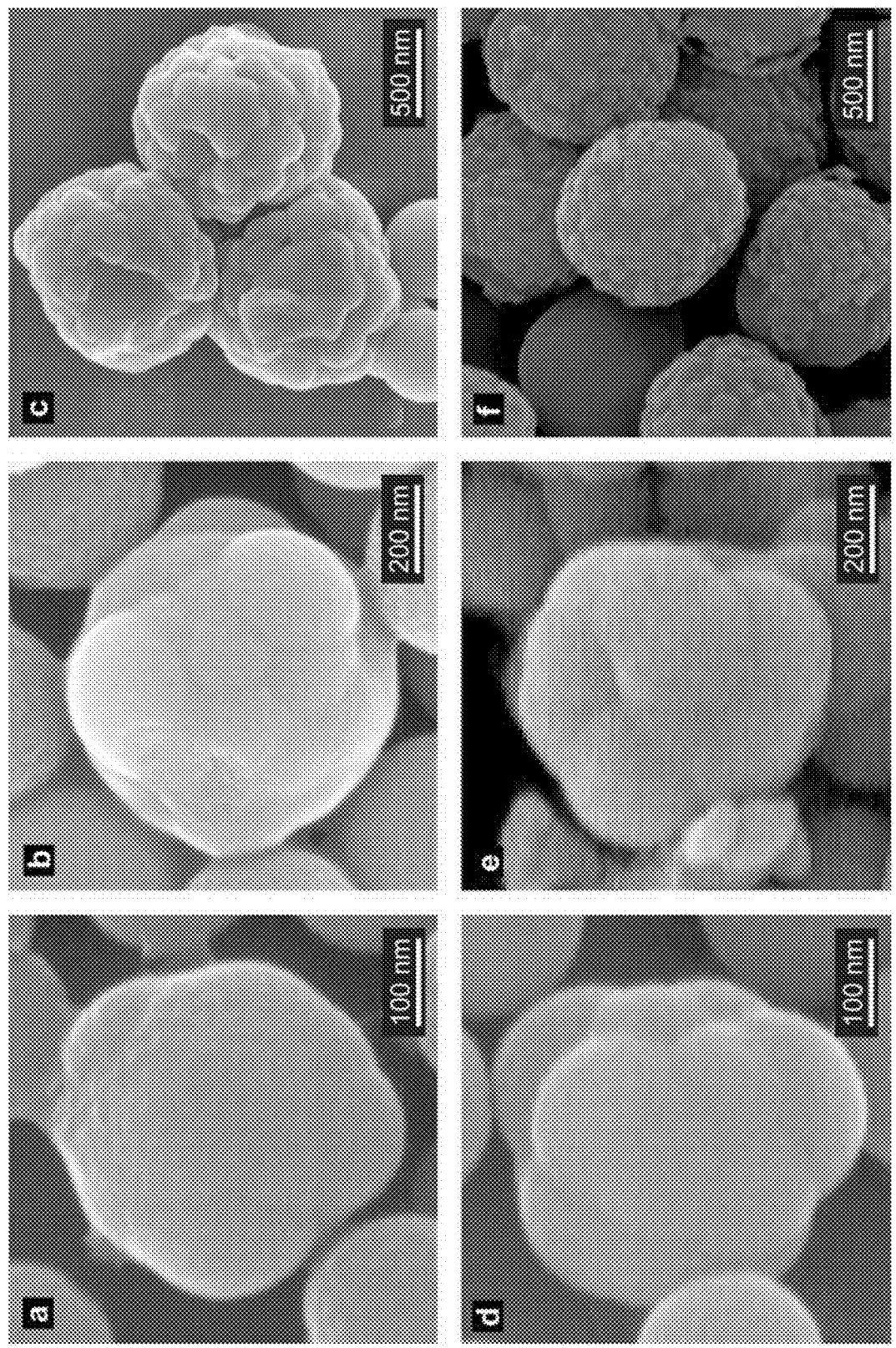
FIG. 38 shows images of exemplary PS/silica composites produced by the exemplary large silica process created by varying the TEOS/PS ratio

FIG. 38 shows images of exemplary PS/silica composites produced by the exemplary small silica process created by varying the TEOS/PS ratio at $10^{10}$ (images (a), (b), and (c), and at $10^9$ (images (d), (e), and (f)). Silica-encapsulated cPS was shown to be distinguishable from solid silica particles by their larger diameter and multiple bumps on the surface. For example, as the core size increases from 200 nm (e.g., images (a), (d)), to 400 (e.g., images (b), (e)), and to 1000 nm (e.g., images (c), (f)), the bumps become more noticeable and numerous to the point where they may not completely cover the surface of the particles. Similar to the exemplary results in FIG. 37, raspberry-like shells coated all cPS cores and excess TEOS formed silica nanoparticles as well, as shown in the results of FIG. 38. These example results suggest that in general, changing the TEOS/PS ratio did not greatly affects the overall morphology of the raspberry shells. Also the shell developed more numerous bumps as the core size increased. However in comparing samples with the same TEOS/PS ratio and cPS core size between the small (e.g., the condition to make the small $b-SiO_2$ particle) and large (e.g., the condition to make the large $b-SiO_2$ particle) recipes (e.g., image (a) of FIG. 37 vs. image (a) of FIG. 38), the individual bumps on the silica shell were reduced in size using the small recipe compared to the large recipe.

Figure 39:
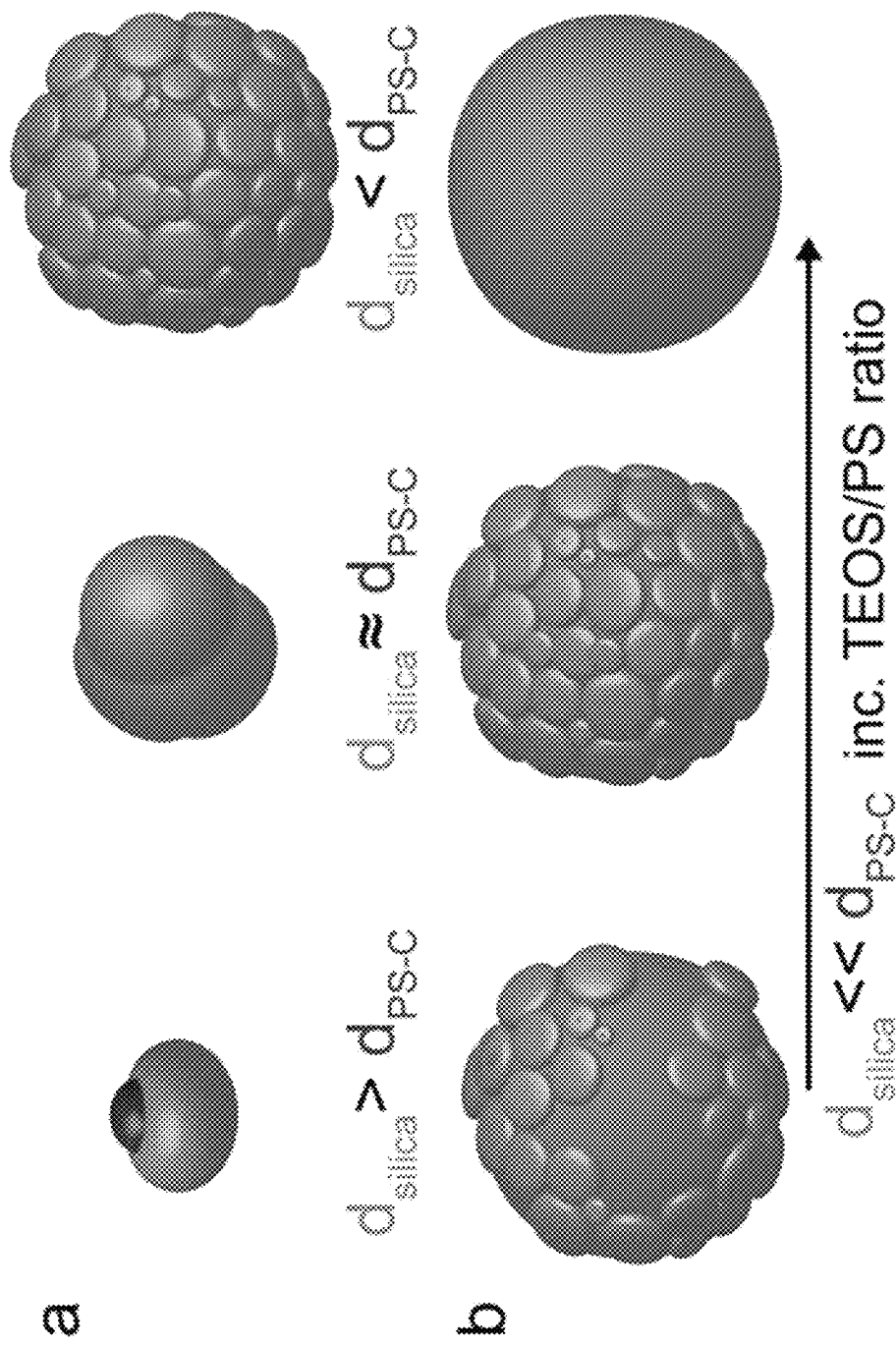
FIG. 39 shows an illustrative diagram of an exemplary model of the effects of the core in Janus particles formation.

FIG. 39 shows an illustrative diagram of an exemplary model of the effects of the core in Janus particles formation. For example, when the core size is much smaller than the $b-SiO_2$ particle size Janus particles will form. As the core and $b-SiO_2$ diameter approach each other's size, a raspberry-like shell will form around the cPS with only a few bumps. When the core is much larger than $b-SiO_2$, the TEOS will form a raspberry-like shell with numerous rounded protrusions around the PS core. The larger the size difference between the core and the $b-SiO_2$, the more pronounced and numerous are the bumps. Additionally any excess TEOS that did not incorporate into a raspberry shell then goes into forming silica nanoparticles similar to the size of $b-SiO_2$. If the cPS core diameter is kept the same and the TEOS/PS ratio is increased, an increasingly bumpy silica shell is formed that continues to coalesce together to form a smoother shell (panel (b) of FIG. 39).

Exemplary Implementations of Capturing Colloidal Gold Nanoparticles with Exemplary Janus Silica Nanoparticles Janus Particles Exemplary implementations are described that demonstrate an exemplary dual functionalized silica nanoparticles-based gold nanoparticles (GNPs) capturer platform (silica golf ball) capable of physically adsorption of various sized GNPs in the pH controlled buffer. For example, using heterogeneous hierarchical template synthesis derived silica golf balls, one or more colloidal GNPs were simultaneously captured with the silica golf balls dispersed in a pH controlled buffer with the predetermined solution's ionic strength. Example acquired scanning electron microscope (SEM) images are presented to locate the GNPS on the silica golf balls. This exemplary biocompatible capturer platform template of the disclosed technology entails a larger functionalized silica core with 100 nm diameter polystyrene particles physically adsorbed to the silica core surface. In one example, a biocompatible capturer platform with 100 nm pits was fabricated by selectively coating silica on the functionalized silica core, followed by dissolution of the polystyrene particles with organic solvent. For example, the capturer platform can be quite useful for recycling medical GNPs, providing a valuable tool for eco-friendly sustainable application of GNPs in human healthcare. The capturer platform can also potentially find the application in non-invasively mining GNPs from plant tissues or cells favoring gold accumulation, providing a valuable tool for mining GNPs as natural products.

'Greener', more sustainable GNP synthesis and sorting procedures can be achieved by relying more on biosynthetic methods followed by non-invasive GNP capture with silica golf balls, and less on toxic chemical synthesis methods. Using an exemplary modified hierarchical template strategy with different core (e.g., silica) and satellite (e.g., polystyrene) materials, the results of these exemplary implementations show that the goal of selective surface functionalization of silica nanoparticles can be achieved by heterogeneous hierarchical template strategy. Also shown is that the heterogeneous hierarchical template strategy can be equally size scalable as its homogeneous counterpart. For example, the silica golf balls are shown to be capable of capturing colloidal gold nanoparticles inside the pH controlled buffer.

Figure 40:
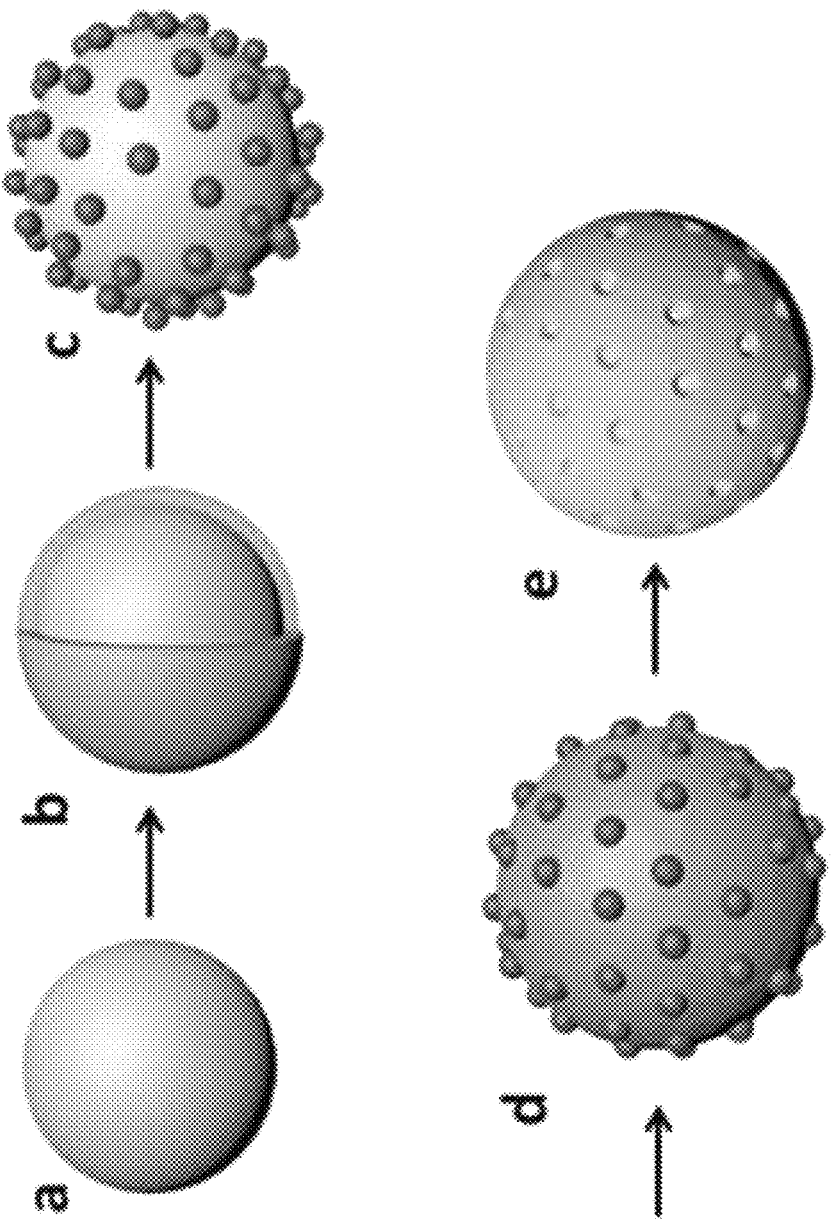
FIG. 40 shows an illustrative diagram of an exemplary synthesis method.

The synthesis of functionalized NP and the preparation of silica golf balls used the following three processes, for example: (1) PS attached template synthesis; (2) TEOS plating on the template; and (3) PS etching. The exemplary results of the amine and quaternary ammonium functionalized NP fabrication, and the silica golf ball preparation were morphologically evaluated by scanning electron microscopy (SEM) via an FEI XL30 SFEG UHR SEM. For example, the silica golf balls were synthesized by TEOS self-assembly on pre-fabricated template particles. This reaction was catalyzed by concentrated ammonium. The template particles were prepared by physically adsorbing smaller 100 nm PS particles on the amine functionalized 1000 nm silica particles and on the quaternary ammonium functionalized 1000 nm silica particles, respectively. Later, for example, the 100 nm PS particles were etched out from the silica golf ball surface by dissolving the particles in DMF heating to 60° C. in the water bath. FIG. 40 shows an illustrative diagram of an exemplary synthesis method. FIG. 40 shows an exemplary heterogeneous hierarchical template process applied in the synthesis of silica golf balls. Panel (a) shows exemplary silica core (e.g., gray); panel (b) shows the exemplary silica core functionalized with a shell (e.g., green) of (3-aminopropyl)-trimethoxysilane (APTMS) or N-trimethyoxysilyl-propyl-N,N,N-trimethylammonium chloride with smaller polystyrene (PS) satellite spheres (e.g., blue) electrostatically attached, as shown in panel (c). Panel (d) shows an exemplary TEOS shell that grows into an interconnected silica shell outside the functionalized shell. Panel (e) shows the dissolution of the polystyrene satellites completes the synthesis of the silica golf ball particles.

Figure 41:
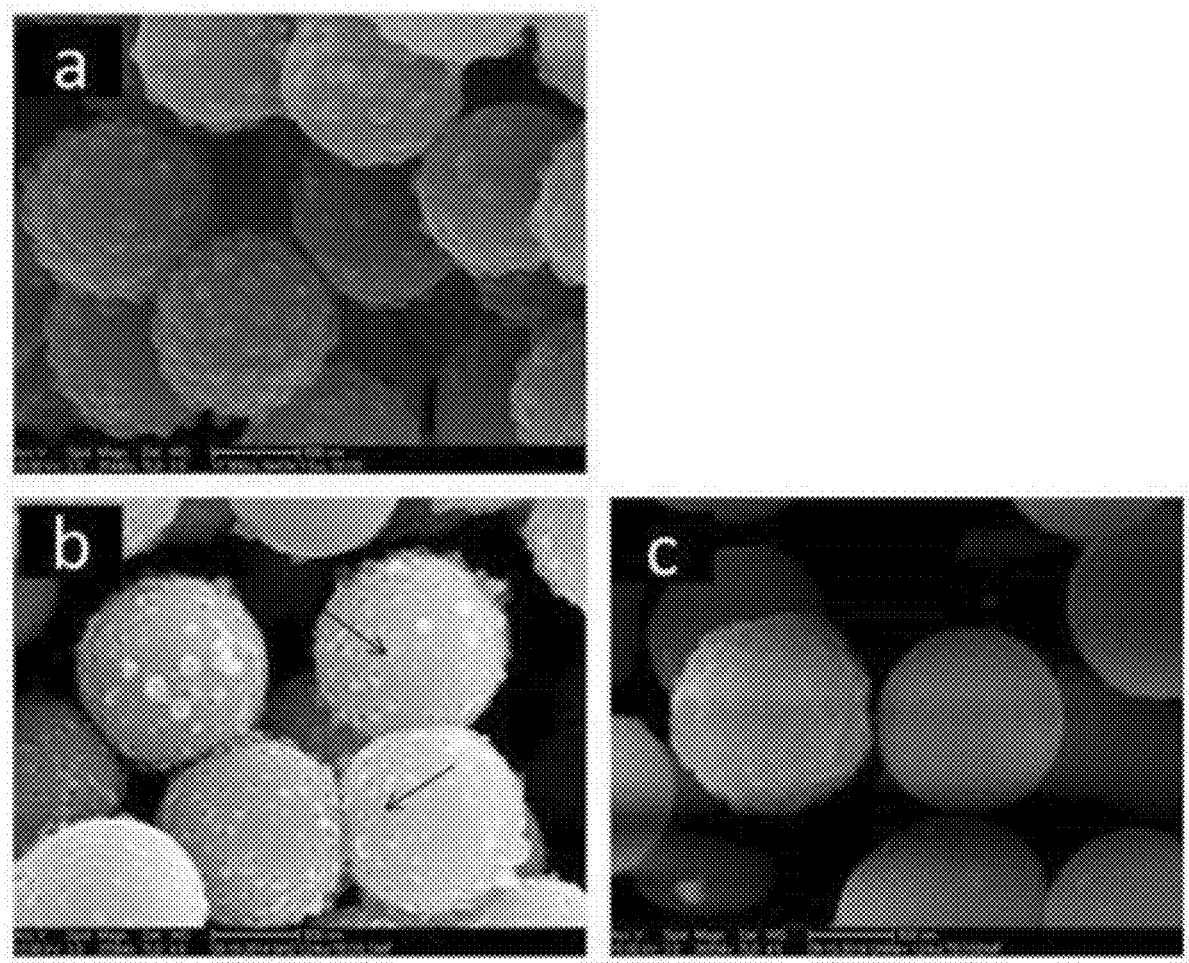
FIG. 41 shows SEM images of the exemplary functionalized particles.

FIG. 41 shows SEM images of the exemplary functionalized particles, e.g., from stages of the silica golf ball synthesis process using 1000 nm silica cores. For example, panel (a) shows a pollen resembling structure created by the self-assembly of 100 nm carboxylate-modified polystyrene on the surface of amine or quaternary ammonium functionalized 1000 nm silica balls. Panel (b) shows, after TEOS growth on the amine functionalized shell, removal of the polystyrene renders porous golf ball resembling structures (arrows indicate the pores). Panel (c) shows, after TEOS growth on the quaternary functionalized shell, removal of the polystyrene renders porous golf ball resembling structures.

The APTMS amount and the N-trimethyoxysilylpropyl-N,N,N-trimethylammonium chloride amount were varied during the synthesis process, and finally, the amount of both compounds were tuned to saturation. The concentration of silica NPs and carboxylated PS NPs, and the amount of surface functionalization chemicals all count for the density of PS NPs on the surface of the core particle.

In the PS etching process, for example, chloroform, toluene and dimethylformamide (DMF) were evaluated the capacity to etch the PS away. The desired solvent dissolves the PS and prevents the PS sticky to the silica golf ball, instead of only softening the PS. In these exemplary implementations, for example, DMF worked the best. In these exemplary implementations, for example, the density of chloroform was high so that the particles were hard to be centrifuged out the solution. Moreover, the chloroform only etched out a large part of PS from the particle surface, and the left over PS was sticky that the golf ball pits could be covered by the PS. In these exemplary implementations, for example, toluene did not perform well for removing PS particles, either. Thus, DMF was used to remove the PS, e.g., three times with DMF while the temperature was kept at 60° C. in the water bath.

Figure 42:
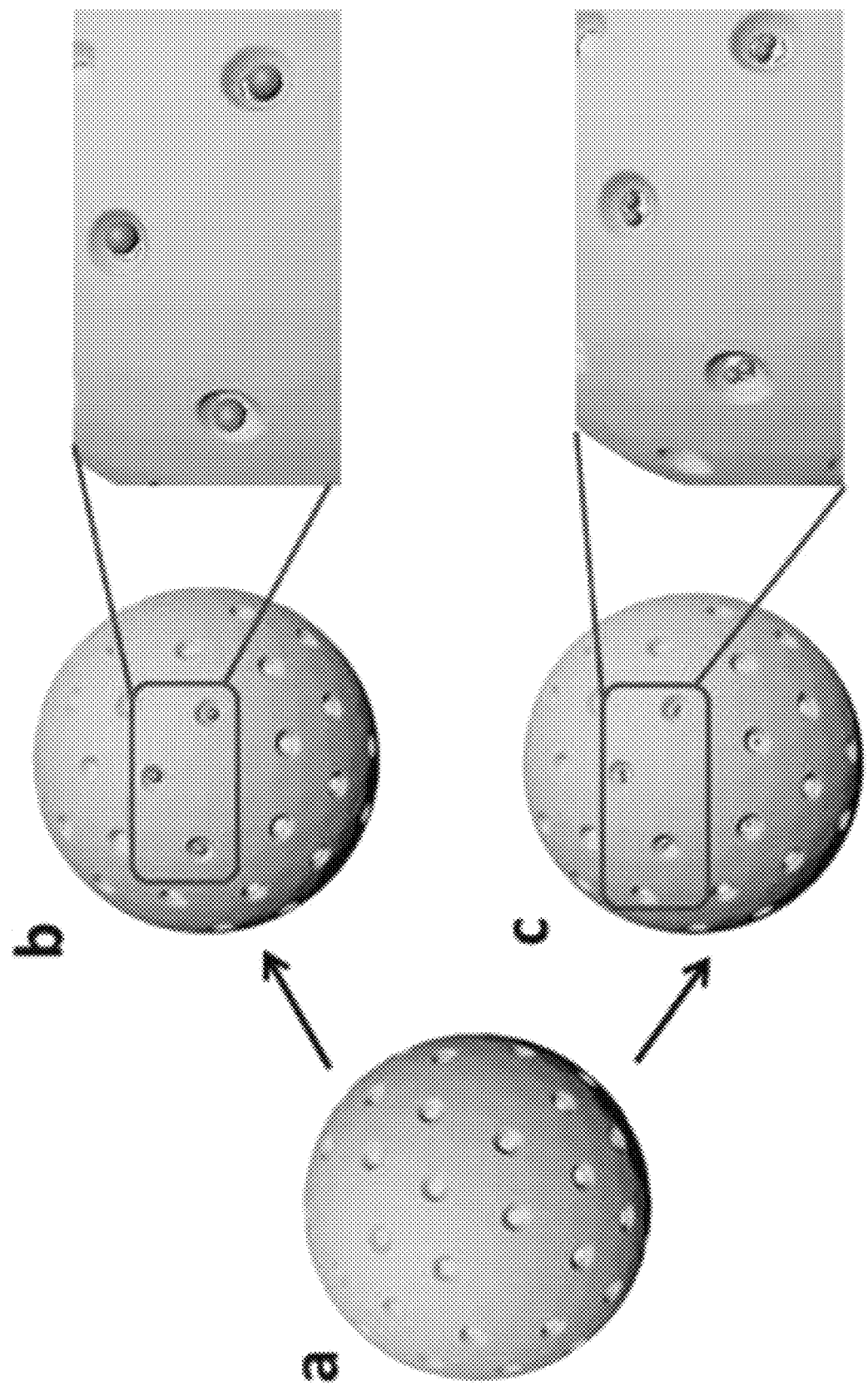
FIG. 42 shows an illustrative diagram of exemplary silica golf balls capturing the gold colloidal particles.
Figure 43:
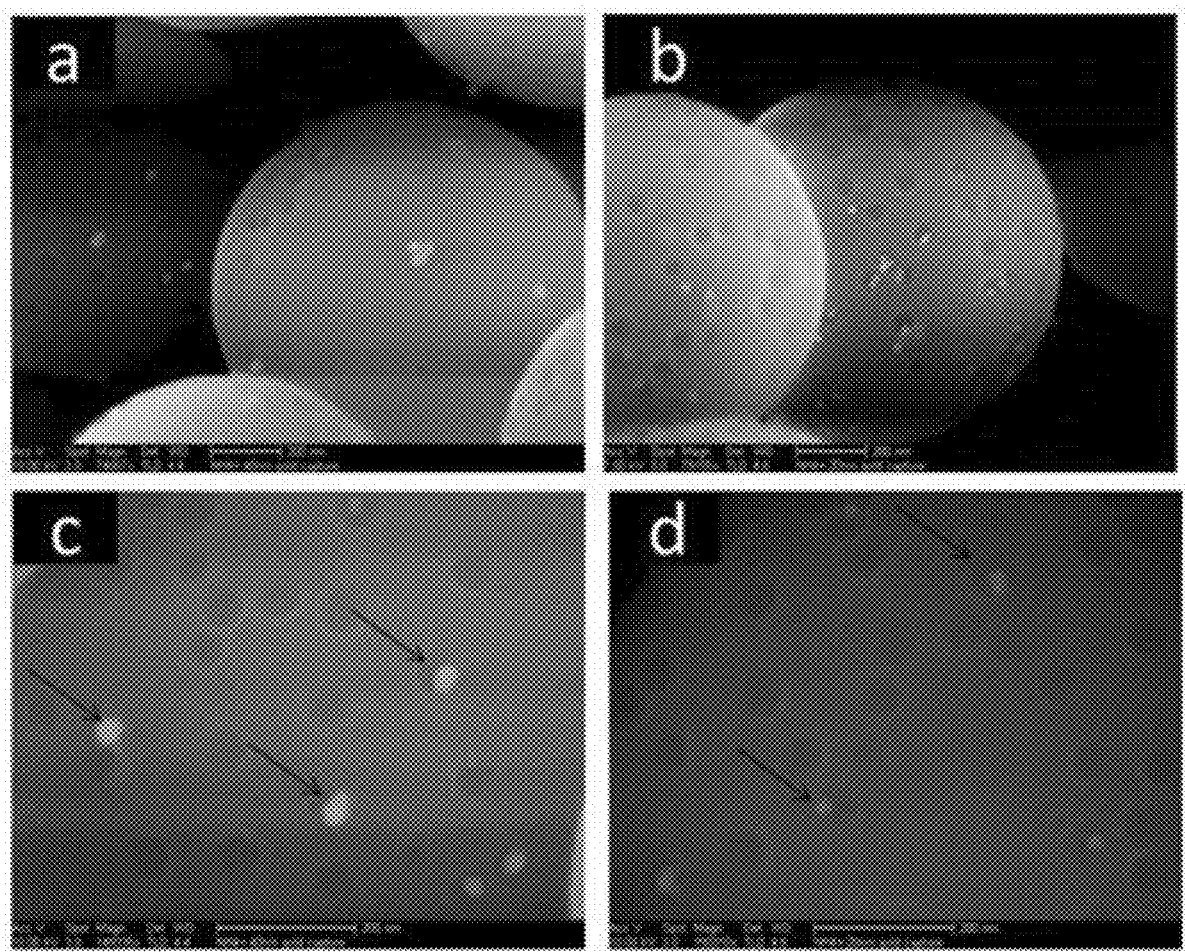
FIG. 43 shows SEM images of the synthesized silica golf balls with quaternary ammonium functionalized pits capturing gold nanoparticles.

In these exemplary implementations, for example, the capture of the GNPs by the quaternary ammonium functionalized silica golf balls was achieved only in the pH controlled buffer. Adsorption of GNPs by silica golf balls was not observed by capture reaction in water or water-ethanol mixture. The capture reaction was performed in five different kinds of media, e.g., water, 80% ethanol water solution, 20% ethanol water solution, 20% ethanol in potassium biphthalate buffer and potassium biphthalate buffer. The 40 nm and 20 nm GNPs were tested via the capture reaction in potassium biphthalate buffer. The rate of centrifuging workup was carefully kept at 500 rcp to make sure that GNP capture was not due to mechanical force, but electrical adsorption in the buffer. In these exemplary implementations, for example, both the 40 nm and 20 nm GNPs were captured by the silica golf balls, as shown in FIGS. 42 and 43. GNPs were observed inside the pits of the silica golf balls. For 40 nm GNPs, for example, single GNP capture was achieved in the pits. For 20 nm GNPs, for example, two to three GNPs can preferably be captured by one pit.

FIG. 42 shows an illustrative diagram of exemplary silica golf balls capturing the gold colloidal particles. Panel (a) shows the exemplary silica golf ball particle with quaternary ammonium functionalized inside the pits (e.g., green). Panel (b) shows the exemplary silica golf ball particle captures the 40 nm GNPs with single GNP in each pit. Panel (c) shows the exemplary silica golf ball particle captures 20 nm GNPs, with multiple GNPs in each pit.

FIG. 43 shows SEM images of the synthesized silica golf balls with quaternary ammonium functionalized pits capturing GNPs. Images (a) and (c) show the exemplary silica golf ball particles capture the 40 nm GNPs with single GNP in each pit (arrows indicate GNPs captured by the pores). Images (b) and (d) show the exemplary silica golf ball particles capture 20 nm GNPs, e.g., with multiple GNPs in each pit (arrows indicate GNPs captured by the pores).

Applying a heterogeneous synthetic template made of two different materials, two kinds of silica golf balls were fabricated with potentially phytomining or medical applications. The pits of the silica golf ball have amine or quaternary ammonium functionalized bottom and may facilitate them to be further selectively functionalized. The quaternary ammonium functionalized silica golf balls preferentially captured <50 nm colloidal gold particles in pH=4 buffer. Single capture and multiple captures were dependent on the size of target gold colloidal particles.

The exemplary implementations include the formation of a model of the electrophoretic mobility and the zeta potential measurements. For example, an estimation of the attractive electric field strength of the pit is described as follows.

When colloidal silica is immersed into an aqueous solution, it becomes electrically charged from protonation/deprotonation at the particles surface. The local electrostatic surface charge density σ is dependent on the size of the particle. For example, the value of a is 4 times larger for silica particles with a 2 nm diameter than with a 500 nm diameter. As the diameter of a colloidal silica particle increases, the surface charge density of on the particle decreases. With increasing size the surface charge density of the particle approaches that of a flat sheet.

The electrical charge and potential distribution in the vicinity of a flat plate is governed by the Poisson-Boltzmann equation, $$\Delta^2 \phi = -\frac{F}{\varepsilon_0 \varepsilon_f r^2} \sum z_i C_{i0} \exp\left(-\frac{z_i F}{RT}\right),$$

where $\phi$ is the electric potential within the fluid; F is the Faraday constant; $C_{i0}$ and $z_i$ are the bulk molar concentration and valence of the ith ionic species. The surface charge density of a silica nanoparticle ($\sigma_{SiO_2}$) can be modelled by the full multi-ion charge regulation model, and shown to be given by $$\sigma_{SiO_2} = -FN_{total}\frac{K_A - K_B[H^+]_s^2}{K_A + [H^+]_s + K_B[H^+]_s^2},$$

where $K_A$ and $K_B$ are the equilibrium constants of two assumed protonation reactions. is the, $[H^+]_s$, and $N_{total}$ is the total number site density of silanol functional groups on the solid/liquid interface of the nanoparticle. The value of $N_{total}$ is given by: $N_{total}=N_{SiOH}+N_{SiO^-}+N_{SiOH^+}$. In the exemplary model, estimated is the electrostatic field strength of an individual pit on the surface of the sphere using idealized conditions, and approximated is the surface of the sphere is as an infinite sheet with a negative charge and we approximate the pit as a positive point charge.

The electrostatic field strength is represented by:

$$E_p = \frac{Q_p}{4\pi\varepsilon R^2} \text{ and } E_s = \frac{\sigma_{SiO_2}}{2\varepsilon}$$

$$E_T = E_s - E_p = 0$$

$$R_0 = \sqrt{\frac{Q_p}{2\pi\sigma}},$$

where $R_0$ is the distance from the surface where the net electrostatic field $E_T$=0. Also, $$\mu_e = \frac{v}{E} = \frac{\varepsilon\zeta}{\eta},$$

while α is the radius of the colloidal particle and is the 1/κ is the Debye length. When α·k>>1, the total charge on the surface of the particle is proportional to the zeta potential (i.e. $Q_T \propto \zeta$).

EXAMPLES

The following examples are illustrative of several embodiments of the present technology. Other exemplary embodiments of the present technology may be presented prior to the following listed examples, or after the following listed examples.

In one example of the present technology (example 1), a method to produce a nanostructure for delivering a payload includes forming a shell structure on a core particle to create a template, in which the core particle is partially encased by the shell structure; attaching nanoparticles to the exterior surface of the shell structure; forming a coating on the exterior surface of the shell structure that covers at least some of the attached nanoparticles; removing the core particle from the template, in which the removed core particle forms an internal cavity of the shell structure having an opening from the external surface; and loading the internal cavity of the shell structure with a molecular payload.

Example 2 includes the method as in example 1, in which the shell structure includes silica.

Example 3 includes the method as in example 1, in which the shell structure is formed in an asymmetric shape on the core particle.

Example 4 includes the method as in example 1, in which the shell structure includes a size of substantially 500 nm or less.

Example 5 includes the method as in example 1, in which the core particle includes polystyrene.

Example 6 includes the method as in example 5, in which the polystyrene core particle is functionalized with a carboxylate-terminus coating.

Example 7 includes the method as in example 5, in which the polystyrene core particle includes a size of substantially 150 nm or less.

Example 8 includes the method as in example 1, further including, prior to the attaching the nanoparticles, chemically modifying the external surface of the shell structure.

Example 9 includes the method as in example 1, in which the nanoparticles include one or both of iron oxide nanoparticles and gold nanoparticles.

Example 10 includes the method as in example 9, in which the iron oxide nanoparticles include a size in a range of 5 to 15 nm.

Example 11 includes the method as in example 9, in which the forming the coating includes producing a filling material between at least some of the nanoparticles on the external surface of the shell structure.

Example 12 includes the method as in example 11, in which the producing the filling material includes placing the template in an ionic gold solution, and adding a reducing agent of gold, thereby forming a gold material between the gold nanoparticles attached to the exterior surface and to coat the iron oxide nanoparticles.

Example 13 includes the method as in example 1, in which the attaching the nanoparticles electrostatic interaction of the nanoparticles to the exterior surface of the shell structure.

Example 14 includes the method as in example 1, further including, prior to the loading, etching at least a portion of the shell structure within the internal cavity to remove material from the shell structure.

Example 15 includes the method as in example 1, in which the loading includes functionalizing at least one of the external surface of the shell structure or internal surface of the internal cavity of the shell structure with attachment molecules capable of linking the molecular payload to the shell structure.

Example 16 includes the method as in example 15, further including releasing the molecular payload by applying a stimuli to the shell structure to cause the chemical detachment of the molecular payload from the attachment molecules.

Example 17 includes the method as in example 16, in which the applying the stimuli includes at least one of a presenting a chemical substance, emitting light, changing a pH environment, or changing temperature.

Example 18 includes the method as in example 1, further including attaching a capping particle to the shell structure to cover the opening and contain the molecular payload within the internal cavity, in which the capping particle is attached to allow controllable movement to expose the opening based on an external stimuli.

Example 19 includes the method as in example 18, in which the capping particle is attached to the shell structure by molecular self-assembly of a self-assembled monolayer (SAM) formed on the surface of the capping particle.

Example 20 includes the method as in example 18, in which the capping particle is attached to the shell structure by a nucleic acid having a two strands of a complementary sequence of nucleotides, a first strand attached to the capping particle and a complimentary second strand attached to the interior cavity of the shell structure.

Example 21 includes the method as in example 18, further including releasing the molecular payload by applying an external stimuli to the shell structure to cause the controllable movement of the capping particle to expose the opening of the shell structure.

Example 22 includes the method as in example 21, in which the applying the external stimuli includes applying heat.

Example 23 includes the method as in example 1, in which the molecular payload includes at least one of a drug, image contrast agent, enzyme, protein, hormone, glycoprotein, glycolipid, nucleic acid, aptamer, lipid, or metallic, polymeric, or ceramic nanoparticle.

In one example of the present technology (example 24), a device for delivering a payload includes a shell structure structured to include an opening to an internal cavity of the shell structure; a coating at least partially formed on an exterior surface of the shell structure and including a plurality of magnetic nanoparticles within the coating; and a functionalization layer on a surface of the internal cavity capable of chemically attaching a molecular payload to the shell structure.

Example 25 includes the device as in example 24, in which the shell structure includes silica.

Example 26 includes the device as in example 24, in which the shell structure includes a size of substantially 200 nm or less.

Example 27 includes the device as in example 24, in which the magnetic nanoparticles include iron oxide nanoparticles.

Example 28 includes the device as in example 24, in which the magnetic nanoparticles include a size in a range of 5 to 15 nm.

Example 29 includes the device as in example 24, in which the magnetic nanoparticles are capable of interaction with an external magnetic field to magnetically steer the nanostructure.

Example 30 includes the device as in example 24, in which the coating includes gold.

Example 31 includes the device as in example 24, further including targeting ligand molecules conjugated to the shell structure, the ligand molecules having an affinity to a receptor molecule found on a target structure to attract and bind the shell structure to the target structure.

Example 32 includes the device as in example 24, in which the device is operable to controllably release the molecular payload by applying a stimuli to the shell structure to cause the chemical detachment of the molecular payload from the functionalization layer.

Example 33 includes the device as in example 32, in which the stimuli includes at least one of a chemical substance, light, pH environment, or temperature.

Example 34 includes the device as in example 24, in which the molecular payload includes at least one of a drug, image contrast agent, enzyme, protein, hormone, glycoprotein, glycolipid, nucleic acid, aptamer, lipid, or metallic, polymeric, or ceramic nanoparticle.

In one example of the present technology (example 35), a device for delivering a payload includes a shell structure structured to include an opening to an internal cavity of the shell structure; a coating at least partially formed on an exterior surface of the shell structure and including a plurality of magnetic nanoparticles within the coating; and a capping particle attached to the shell structure to cover the opening and contain a molecular payload within the internal cavity, in which attachment of the capping particle to the shell structure allows controllable movement of the capping particle to expose the opening based on an external stimuli.

Example 36 includes the device as in example 35, in which the capping particle is attached to the shell structure by molecular self-assembly of a self-assembled monolayer (SAM) formed on the surface of the capping particle.

Example 37 includes the device as in example 35, in which the capping particle is attached to the shell structure by a nucleic acid having a two strands of a complementary sequence of nucleotides, a first strand attached to the capping particle and a complimentary second strand attached to the interior cavity of the shell structure.

Example 38 includes the device as in example 35, in which the device is operable to controllably release the molecular payload by applying heat to the shell structure to cause the controllable movement of the capping particle to expose the opening of the shell structure.

Example 39 includes the device as in example 21, in which the applied the heat includes radio frequency (RF) heating or near infrared (NIR) heating.

Example 40 includes the device as in example 35, in which the shell structure includes silica.

Example 41 includes the device as in example 35, in which the shell structure includes a size of substantially 200 nm or less.

Example 42 includes the device as in example 35, in which the magnetic nanoparticles include iron oxide nanoparticles.

Example 43 includes the device as in example 35, in which the magnetic nanoparticles include a size in a range of 5 to 15 nm.

Example 44 includes the device as in example 35, in which the magnetic nanoparticles are capable of interaction with an external magnetic field to magnetically steer the nanostructure.

Example 45 includes the device as in example 35, in which the coating includes gold.

Example 46 includes the device as in example 35, further including targeting ligand molecules conjugated to the shell structure, the ligand molecules having an affinity to a receptor molecule found on a target structure to attract and bind the shell structure to the target structure.

Example 47 includes the device as in example 35, in which the molecular payload includes at least one of a drug, image contrast agent, enzyme, protein, hormone, glycoprotein, glycolipid, nucleic acid, aptamer, lipid, or metallic, polymeric, or ceramic nanoparticle.

In one example of the present technology (example 48), a method to produce a material structure includes forming a template by attaching a plurality of mask particles on a core particle, the mask particles forming masked regions on the exterior surface of the core particle where they attach; attaching nanoparticles to unmasked surface of the template, in which the mask particles prevent the nanoparticles to attach to the masked regions of the exterior surface; forming a coating over the unmasked surface by material growth of the attached nanoparticles to form a shell structure over the unmasked surface of the template; and removing the masking particles from the template, in which the removed masking particles forms openings extending between an interior region and an external surface of the shell structure encasing the core particle, thereby producing a porous carrier structure.

Example 49 includes the method of example 48, in which the mask particles attach to the core particle by electrostatic interaction.

Example 50 includes the method of example 49, in which the core particle includes cationic silica and the mask particles include polystyrene.

Example 51 includes the method of example 48, in which the nanoparticles include gold nanoparticles.

Example 52 includes the method of example 51, in which the gold nanoparticles include a size of 5 nm or less.

Example 53 includes the method of example 48, in which the forming the coating includes immersing the template particle in a solution containing an outer material of the nanoparticles to cause nucleation and growth around the template particle.

Example 54 includes the method of example 53, in which the nanoparticles include gold nanoparticles and the solution includes gold hydroxide, the forming including producing gold seeds that nucleate into a gold shell structure.

Example 55 includes the method of example 54, in which the porous carrier structure includes an outer gold porous shell formed over a silica core particle.

Example 56 includes the method of example 48, in which the removing includes dissolving the masking particles in a solution.

Example 57 includes the method of example 48, further including removing at least a portion of the core particle from the template to produce a hollow, porous carrier structure.

Example 58 includes the method of example 48, further including forming an outer layer around the porous carrier structure prior to the removing the masking particles from the template, in which the porous carrier structure includes the outer layer having the coating embedded on an inner surface of the outer layer; and removing at least a portion of the core particle from the template to produce a hollow, porous carrier structure.

Example 59 includes the method of example 58, in which the outer layer includes silica, and the coating includes gold.

Example 60 includes the method of example 48, in which the forming the coating over the unmasked surface by material growth of the attached nanoparticles forms discontiguous island structures of the coating over the unmasked surface of the template; and further including forming an outer layer around the shell structure prior to the removing the masking particles from the template, in which the porous carrier structure includes the outer layer having the island structures embedded on an inner surface of the outer layer; and removing at least a portion of the core particle from the template to produce a hollow, porous carrier structure having the island structures embedded on an inner surface of the outer layer.

Example 61 includes the method of example 60, in which the outer layer includes silica, and the island structures includes gold.

Example 62 includes the method of example 58, further including adding magnetic nanoparticles to an interior surface of the produce a hollow, porous carrier structure; and/or adding magnetic nanoparticles to an outside surface of the produce a hollow, porous carrier structure.

Example 63 includes the method of example 62, in which the magnetic nanoparticles include iron oxide nanoparticles.

Example 64 includes the method of example 48, further including loading the porous carrier structure with a molecular payload, in which the loading includes functionalizing the coating with attachment molecules capable of linking the molecular payload.

Example 65 includes the method of examples 58, 60, or 62, further including loading the hollow, porous carrier structure with a molecular payload, in which the loading includes functionalizing at least one of the interior surface or the outside surface with attachment molecules capable of linking the molecular payload.

Example 66 includes the method of examples 64 or 65, further including releasing the molecular payload by applying a stimuli to the carrier structure to cause the chemical detachment of the molecular payload from the attachment molecules.

Example 67 includes the method of example 66, in which the applying the stimuli includes at least one of a presenting a chemical substance, emitting light, changing a pH environment, or changing temperature.

In one example of the present technology (example 68), a particle device includes a shell structure structured to include one or more openings extending between an interior region and an exterior surface of the shell structure; magnetic nanoparticles attached to one or both of the interior region or the exterior region of the shell structure; and a molecular payload attached to the shell structure by attachment molecules capable of linking the molecular payload to a surface of the shell structure.

Example 69 includes the device of example 68, in which the magnetic nanoparticles include iron oxide nanoparticles.

Example 70 includes the device of example 68, in which the shell structure includes an outer layer formed around an interior layer.

Example 71 includes the device of example 70, in which the outer layer includes silica, and the interior layer includes gold.

Example 72 includes the device of example 70, in which the interior layer comprises discontiguous island structures.

Example 73 includes the device of example 72, in which the outer layer includes silica, and the island structures includes gold.

Example 74 includes the device of example 68, in which the molecular payload includes at least one of a drug, image contrast agent, enzyme, protein, hormone, glycoprotein, glycolipid, nucleic acid, aptamer, lipid, and/or metallic, polymeric, or ceramic nanoparticle.

While this patent document contains many specifics, these should not be construed as limitations on the scope of any invention or of what may be claimed, but rather as descriptions of features that may be specific to particular embodiments of particular inventions. Certain features that are described in this patent document in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this patent document should not be understood as requiring such separation in all embodiments.

Only a few implementations and examples are described and other implementations, enhancements and variations can be made based on what is described and illustrated in this patent document.

What is claimed is:

1. A method to fabricate a carrier structure, comprising:
    forming a template by attaching a plurality of mask particles on a core particle, the mask particles forming masked regions on the exterior surface of the core particle where they attach;
    attaching nanoparticles to unmasked surface of the template, wherein the mask particles prevent the nanoparticles to attach to the masked regions of the exterior surface;
    producing a shell structure over the unmasked surface of the template by forming a coating over the unmasked surface by material growth of the attached nanoparticles;
    prior to removing the masking particles from the template, forming an outer layer around the shell structure to produce a bi-layered shell structure; and
    producing a porous carrier structure by removing the mask particles from the template, wherein the removed mask particles form openings extending between an external surface of the bi-layered shell structure and the exterior surface of the core particle.

2. The method of claim 1, wherein the mask particles attach to the core particle by electrostatic interaction.

3. The method of claim 2, wherein the core particle includes cationic silica and the mask particles include polystyrene.

4. The method of claim 2, wherein the core particle includes a size of 1 µm or less, and the mask particles include a size of 100 nm or less.

5. The method of claim 2, wherein the mask particles include polystyrene particles with an outer functionalized coating having a carboxylated terminus.

6. The method of claim 1, wherein the nanoparticles include gold nanoparticles.

7. The method of claim 6, wherein the gold nanoparticles include a size of 5 nm or less.

8. The method of claim 1, wherein the forming the coating includes immersing the template in a solution containing the material of the nanoparticles to cause nucleation and growth on the unmasked surface of the template.

9. The method of claim 8, wherein the nanoparticles include gold nanoparticles and the solution includes gold hydroxide, the forming including producing gold seeds that nucleate into a gold shell structure.

10. The method of claim 1, wherein the porous carrier structure includes an outer gold porous shell formed over a silica core particle.

11. The method of claim 1, wherein the removing the mask particles from the template includes dissolving the mask particles in an organic solvent.

12. The method of claim 1, further comprising:
attaching magnetic nanoparticles to an outside surface of the porous carrier structure.

13. The method of claim 1, further comprising:
loading the porous carrier structure with a molecular payload, wherein the loading includes functionalizing a surface of the bi-layered shell structure or the core particle exposed through the openings, or both, with attachment molecules capable of linking the molecular payload.

14. The method of claim 1, further comprising:
removing at least a portion of the core particle from the template to produce a hollow, porous carrier structure.

15. The method of claim 14, further comprising:
attaching magnetic nanoparticles to a surface of the hollow porous carrier structure.

16. The method of claim 14, further comprising:
loading the hollow porous carrier structure with a molecular payload, wherein the loading includes functionalizing an interior surface or an outside surface of the hollow porous carrier structure with attachment molecules capable of linking the molecular payload.

17. The method of claim 1, wherein the outer layer includes silica, and the shell structure includes gold.

18. The method of claim 13, wherein the molecular payload is capable of being controllably released based on a stimulus including at least one of a chemical substance, an emission of light, a change in pH environment, or a change in temperature to cause detachment of the molecular payload from the carrier structure.

19. The method of claim 16, wherein the molecular payload is capable of being controllably released based on a stimulus including at least one of a chemical substance, an emission of light, a change in pH environment, or a change in temperature to cause detachment of the molecular payload from the carrier structure.

* * * * *

UNITED STATES PATENT AND TRADEMARK OFFICE
CERTIFICATE OF CORRECTION

PATENT NO. : 10,864,270 B2  Page 1 of 1
APPLICATION NO. : 16/111090
DATED : December 15, 2020
INVENTOR(S) : Ratneshwar Lal et al.

It is certified that error appears in the above-identified patent and that said Letters Patent is hereby corrected as shown below:

In the Specification

STATEMENT REGARDING FEDERALLY SPONSORED RESEARCH OR DEVELOPMENT section, Column 1, Lines 30-32, delete:
"This invention was made with government support under DA024871 and DA025296 awarded by the National Institute on Health. The government has certain rights in the invention."

And insert:
--This invention was made with government support under DA024871 and DA025296 awarded by the National Institutes of Health. The government has certain rights in the invention.--

Signed and Sealed this
Second Day of December, 2025

John A. Squires
*Director of the United States Patent and Trademark Office*